(12) United States Patent
Kester et al.

(10) Patent No.: US 9,562,849 B2
(45) Date of Patent: Feb. 7, 2017

(54) DIVIDED-APERTURE INFRA-RED SPECTRAL IMAGING SYSTEM

(71) Applicant: REBELLION PHOTONICS, INC., Houston, TX (US)

(72) Inventors: Robert Timothy Kester, Houston, TX (US); Nathan Adrian Hagen, Houston, TX (US)

(73) Assignee: Rebellion Photonics, Inc., Houston, TX (US)

( * ) Notice: Subject to any disclaimer, the term of this patent is extended or adjusted under 35 U.S.C. 154(b) by 0 days.

(21) Appl. No.: 14/538,827

(22) Filed: Nov. 12, 2014

(65) Prior Publication Data
US 2015/0136982 A1 May 21, 2015

Related U.S. Application Data

(60) Provisional application No. 61/903,075, filed on Nov. 12, 2013.

(51) Int. Cl.
*H01L 25/00* (2006.01)
*G01N 21/3504* (2014.01)
(Continued)

(52) U.S. Cl.
CPC ......... *G01N 21/3504* (2013.01); *G01J 3/0208* (2013.01); *G01J 3/0232* (2013.01);
(Continued)

(58) Field of Classification Search
CPC .......... H04N 5/33; H04N 3/09; H04N 5/3655; H04N 5/3651
See application file for complete search history.

(56) References Cited

U.S. PATENT DOCUMENTS

| 4,134,683 A | 1/1979 | Goetz et al. |
| 4,963,963 A * | 10/1990 | Dorman ................ 348/164 |

(Continued)

FOREIGN PATENT DOCUMENTS

| CA | 2 365 866 | 9/2000 |
| CA | 2 870 419 | 5/2015 |

(Continued)

OTHER PUBLICATIONS

Allen et al., "Measurements of Methane Emissions at Natural Gas Production Sites in the United States", PNAS, Oct. 29, 2013, vol. 110, No. 44, pp. 7.

(Continued)

*Primary Examiner* — Kiho Kim
(74) *Attorney, Agent, or Firm* — Knobbe Martens Olson & Bear LLP

(57) ABSTRACT

Various embodiments disclosed herein describe a divided-aperture infrared spectral imaging (DAISI) system that is adapted to acquire multiple IR images of a scene with a single-shot (also referred to as a snapshot). The plurality of acquired images having different wavelength compositions that are obtained generally simultaneously. The system includes at least two optical channels that are spatially and spectrally different from one another. Each of the at least two optical channels are configured to transfer IR radiation incident on the optical system towards an optical FPA unit comprising at least two detector arrays disposed in the focal plane of two corresponding focusing lenses. The system further comprises at least one temperature reference source or surface that is used to dynamically calibrate the two detector arrays and compensate for a temperature difference between the two detector arrays.

66 Claims, 15 Drawing Sheets

(51) Int. Cl.

| | | |
|---|---|---|
| H04N 5/33 | (2006.01) | |
| H04N 3/09 | (2006.01) | |
| H04N 5/365 | (2011.01) | |
| G01J 3/02 | (2006.01) | |
| G01J 3/36 | (2006.01) | |
| G01J 5/52 | (2006.01) | |
| G01J 3/28 | (2006.01) | |
| G01J 5/00 | (2006.01) | |
| G01J 5/08 | (2006.01) | |
| G01J 3/26 | (2006.01) | |
| G01J 5/20 | (2006.01) | |
| G01N 21/17 | (2006.01) | |

(52) U.S. Cl.
CPC ........... *G01J 3/0256* (2013.01); *G01J 3/0297* (2013.01); *G01J 3/26* (2013.01); *G01J 3/28* (2013.01); *G01J 3/2823* (2013.01); *G01J 3/36* (2013.01); *G01J 5/0014* (2013.01); *G01J 5/0806* (2013.01); *G01J 5/0834* (2013.01); *G01J 5/0862* (2013.01); *G01J 5/20* (2013.01); *G01J 5/522* (2013.01); *H04N 3/09* (2013.01); *H04N 5/33* (2013.01); *H04N 5/365* (2013.01); *H04N 5/3651* (2013.01); *H04N 5/3655* (2013.01); *G01J 2003/2826* (2013.01); *G01J 2005/0077* (2013.01); *G01N 2021/1793* (2013.01); *G01N 2021/3531* (2013.01); *G01N 2201/068* (2013.01); *G01N 2201/06106* (2013.01)

(56) References Cited

U.S. PATENT DOCUMENTS

| | | | |
|---|---|---|---|
| 5,127,742 | A | 7/1992 | Fraden |
| 5,877,500 | A | 3/1999 | Braig et al. |
| 5,920,066 | A * | 7/1999 | DiRenzo et al. .......... 250/252.1 |
| 5,926,283 | A | 7/1999 | Hopkins |
| 6,023,061 | A | 2/2000 | Bodkin |
| 6,268,883 | B1 | 7/2001 | Zehnder et al. |
| 6,456,261 | B1 | 9/2002 | Zhang |
| 6,680,778 | B2 | 1/2004 | Hinnrichs et al. |
| 7,242,478 | B1 | 7/2007 | Dombrowski et al. |
| 7,315,377 | B2 | 1/2008 | Holland et al. |
| 7,750,802 | B1 | 7/2010 | Parish et al. |
| 7,835,002 | B2 | 11/2010 | Muhammed et al. |
| 7,888,624 | B1 | 2/2011 | Murguia et al. |
| 8,159,568 | B2 * | 4/2012 | Ahdoot ........................ 348/241 |
| 8,653,461 | B1 | 2/2014 | Benson et al. |
| 8,654,328 | B2 | 2/2014 | Tkaczyk et al. |
| 2002/0015151 | A1 | 2/2002 | Gorin |
| 2002/0121370 | A1 | 9/2002 | Kurkjian et al. |
| 2002/0159101 | A1 * | 10/2002 | Alderson et al. ............. 358/504 |
| 2003/0134426 | A1 | 7/2003 | Jiang et al. |
| 2005/0103989 | A1 * | 5/2005 | Watson et al. ............. 250/252.1 |
| 2006/0044562 | A1 | 3/2006 | Hagene et al. |
| 2008/0204744 | A1 | 8/2008 | Mir et al. |
| 2008/0231719 | A1 | 9/2008 | Benson et al. |
| 2008/0251724 | A1 | 10/2008 | Baliga et al. |
| 2010/0211333 | A1 | 8/2010 | Pruet et al. |
| 2011/0261321 | A1 | 10/2011 | Ramella-Roman et al. |
| 2012/0273680 | A1 | 11/2012 | Furry |
| 2013/0181836 | A1 | 7/2013 | Cardoso et al. |
| 2013/0321806 | A1 | 12/2013 | Kester et al. |
| 2013/0341509 | A1 | 12/2013 | Nelson et al. |
| 2015/0069239 | A1 | 3/2015 | Kester et al. |
| 2015/0136981 | A1 | 5/2015 | Kester et al. |
| 2015/0316473 | A1 | 11/2015 | Kester et al. |
| 2016/0097713 | A1 | 4/2016 | Kester et al. |
| 2016/0349228 | A1 | 12/2016 | Kester et al. |

FOREIGN PATENT DOCUMENTS

| | | | |
|---|---|---|---|
| EP | 0 837 600 | 4/1998 | |
| EP | 2 871 452 | 5/2015 | |
| EP | 2 942 615 | 11/2015 | |
| EP | 2 955 496 | 12/2015 | |
| GB | 1014769 A | * 12/1965 | .............. G01J 5/505 |
| WO | WO 2004/097389 | 11/2004 | |
| WO | WO 2007/008826 | 1/2007 | |
| WO | WO 2008/109183 | 9/2008 | |
| WO | WO 2009/094782 | 8/2009 | |
| WO | WO 2010/053979 | 5/2010 | |
| WO | WO 2012/078417 | 6/2012 | |
| WO | WO 2012/082366 | 6/2012 | |
| WO | WO 2013/173541 | 11/2013 | |
| WO | WO 2016/196224 | 12/2016 | |

OTHER PUBLICATIONS

Alvarez et al., "Greater Focus Needed on Methane Leakage from Natural Gas Infrastructure", PNAS, Apr. 24, 2012, vol. 109, No. 17, pp. 12.

Bedard et al., "Image Mapping Spectrometry: Calibration and Characterization", Optical Engineering, Nov. 2012, vol. 51, No. 11, pp. 111711-1-111711-13.

Ben-David et al., "Probability Theory for 3-Layer Remote Sensing Radiative Transfer Model: Univariate Case," Optics Express, Apr. 2012, vol. 20, No. 9, pp. 10004-10033.

Ben-David et al., "Probability Theory for 3-Layer Remote Sensing Radiative Transfer Model: Errata," Optics Express, May 20, 2013, vol. 21, No. 10, pp. 11852.

Brady et al., "Multiscale Lens Design", Optics Express, Jun. 22, 2009, vol. 17, No. 13, pp. 10659-10674.

Caulton et al., "Toward a Better Understanding and Quantification of Methane Emissions from Shale Gas Development", PNAS, Apr. 29, 2014, vol. 111, No. 17, pp. 7.

Chen et al., "Quantitative Sectioning and Noise Analysis for Structured Illumination Microscopy: Erratum", Optics Express, Oct. 19, 2015, vol. 23, No. 21, pp. 27633-27634.

Chidley et al., "Flow-Induced Birefringence: The Hidden PSF Killer in High Performance Injection-Molded Plastic Optics", Endoscopic Microscopy, Proceedings of SPIE vol. 6082, 2006, pp. 11.

Chu et al., "The NIST Quantitiative Infrared Database", Journal of Research of the National Institute of Standards and Technology, Jan.-Feb. 1999, vol. 104, No. 1, pp. 59-81.

DiPietro et al., "Hyperspectral Matched Filter with False-Alarm Mitigation", Optical Engineering, Jan. 2012, vol. 51, No. 1, pp. 016202-1-016202-7.

Eriksson et al., "Radiative Cooling Computed for Model Atmospheres", Applied Optics, Dec. 1, 1982, vol. 21, No. 23, pp. 4381-4388.

Flanigan, "Detection of Organic Vapors with Active and Passive Sensors: A Comparison," Applied Optics, 1986, vol. 25, No. 23, pp. 4253-4260.

Gallagher et al., "Error Analysis for Estimation of Trace Vapor Concentration Pathlength in Stack Plumes", Applied Spectroscopy, 2003, vol. 57, No. 6, pp. 614-621.

Gallagher et al., "Estimation of Trace Vapor Concentration-Pathlength in Plumes for Remote Sensing Applications from Hyperspectral Images", Analytica Chimica Acta, 2003, vol. 490, pp. 139-152.

Gao et al., "Compact Image Slicing Spectrometer (ISS) for Hyperspectral Fluorescence Microscopy", Optics Express, Jul. 20, 2009, vol. 17, No. 15, pp. 12293-12308.

Gao et al., "Depth-Resolved Image Mapping Spectrometer (IMS) with Structured Illumination", Optics Express, Aug. 29, 2011, vol. 19, No. 18, pp. 17439-17452.

Gao et al., "Optical Design of a Snapshot High-Sampling Image Mapping Spectrometer (IMS) for Hyperspectral Microscopy", Three-Dimensional and Multidimensional Microscopy:Image Acquisition and Processing XVII, Proceedings of SPIE vol. 7570, 2010, pp. 1-7.

(56) References Cited

OTHER PUBLICATIONS

Gao et al., "Quantitative Comparison Between Full-Spectrum and Filter-Based Imaging in Hyperspectral Fluorescence Microscopy", Journal of Microscopy, 2012, vol. 246, No. 2, pp. 113-123.

Gao et al., "Snapshot Image-Mapping Spectrometer for Hyperspectral Fluorescence Microscopy", Optics and Photonics News, Nov. 2010, vol. 21, No. 12, p. 50.

Gao et al., "Snapshot Image Mapping Spectrometer (IMS) with High Sampling Density for Hyperspectral Microscopy", Optics Express, Jul. 5, 2010, vol. 18, No. 4, pp. 14330-14344.

Gerhart et al., "Detection and Tracking of Gas Plumes in LWIR Hyperspectral Video Sequence Data," Algorithms and Technologies for Multispectral, Hyperspectral, and Ultraspectral Imagery XIX, 2013, SPIE Proceedings vol. 8743, pp. 1-14.

Gittins, Christopher M., "Detection and Characterization of Chemical Vapor Fugitive Emissions by Nonlinear Optimal Estimation: Theory and Simulation", Applied Optics, Aug. 10, 2009, vol. 48, No. 23, pp. 4545-4561.

Goldberg et al., "Dual Band MWIR/LWIR Focal Plane Array Test Results," Army Research Lab, Adelphi, MD, Aug. 1999, pp. 18.

Golowich et al., "Performance Limits of LWIR Gaseous Plume Quantification", Algorithms and Technologies for Multispectral, Hyperspectral, and Ultraspectral Imagery XVII, 2011, Proceedings of SPIE vol. 8048, pp. 1-12.

Griffin et al., "The Herschel—SPIRE Instrument and its In-Flight Performance," Astronomy and Astrophysics, Jul. 1, 2010, vol. 518, 7 pages.

Gross et al., "Remote Identification and Quantification of Industrial Smokestack Effluents via Imaging Fourier-Transform Spectroscopy", Environmental Science & Technology, 2010, vol. 44, No. 24, pp. 9390-9397.

Gupta et al., "Miniature Snapshot Multispectral Imager," Optical Engineering, 2011, vol. 50, pp. 033203-1-033203-9.

Hagen et al., "Analysis of Computed Tomographic Imaging Spectrometers. I. Spatial and Spectral Resolution", Applied Optics, Oct. 1, 2008, vol. 47, No. 28, pp. F85-F95.

Hagen et al., "Coded Aperture DUV Spectrometer for Standoff Raman Spectoscopy", Next-Generation Spectroscopic Technologies II, Proceedings of SPIE vol. 7319, 2009, pp. 1-10.

Hagen et al., "Compound Prism Design Principles, I", Applied Optics, Sep. 1, 2011, vol. 50, No. 25, pp. 4998-5011.

Hagen et al., "Compound Prism Design Principles, II: Triplet and Janssen Prisms", Applied Optics, Sep. 1, 2011, vol. 50, No. 25, pp. 5012-5022.

Hagen et al., "Compound Prism Design Principles, III: Linear-in-Wavenumber and Optical Coherence Tomography Prisms", Applied Optics, Sep. 1, 2011, vol. 50, No. 25, pp. 5023-5030.

Hagen et al., "Fourier Methods of Improving Reconstruction Speed for CTIS Imaging Spectrometers", Imagin Spectrometry XII, Proceedings of SPIE vol. 6661, 2007, pp. 11.

Hagen et al., "Foveated Endoscopic Lens", Journal of Biomedical Optics, Feb. 2012, vol. 17, No. 2, pp. 021104-1-021104-6.

Hagen et al., "Gaussian Profile Estimation in One Dimension", Applied Optics, Aug. 1, 2007, vol. 46, No. 22, pp. 5374-5383.

Hagen et al., "Gaussian Profile Estimation in Two Dimension", Applied Optics, Dec. 20, 2008, vol. 47, No. 36, pp. 6842-6851.

Hagen et al., "Quantitative Sectioning and Noise Analysis for Structured Illumination Microscopy", Optics Express, Jan. 2, 2012, vol. 20, No. 1, pp. 403-413.

Hagen et al., "Quantitative Sectioning and Noise Analysis for Structured Illumination Microscopy: Errata", Optics Express, Feb. 27, 2012, vol. 20, No. 5, 5343.

Hagen et al., "Real-Time Quantitative Hydrocarbon Gas Imaging with the Gas Cloud Imager (GCI)", Proceedings of SPIE, vol. 8358, Chemical, Biological, Radiological, Nuclear, and Explosives (CBRNE) Sensing XIII, May 1, 2012, 7 pages.

Hagen et al., "Review of Snapshot Spectral Imaging Technologies", Optical Engineering, Sep. 2013, vol. 52, No. 9, pp. 090901-1-090901-23.

Hagen et al., "Snapshot Advantage: A Review of the Light Collection Improvement for Parallel High-Dimensional Measurement Systems," Optical Engineering, Jun. 13, 2012, vol. 51, No. 11, p. 111702-1-111702-7.

Hagen et al., "Snapshot Mueller Matrix Spectropolarimeter" Optics Letters, Aug. 1, 2007, vol. 32, No. 15, pp. 2100-2102.

Hagen et al., "Spectrally-Resolved Imaging of Dynamic Turbid Media", Multimodal Biomedical Imaging VI, Proceedings of SPIE vol. 7892, 2011, pp. 1-7.

Hagen et al., "Video-Rate Spectral Imaging of Gas Leaks in the Longwave Infrared," Chemical, Biological, Radiological, Nuclear, and Explosives (CBRNE) Sensing XIV, May 29, 2013, SPIE Proceedings vol. 8710, pp. 7.

Harley et al., "Remote Quantification of Smokestack Effluent Mass Flow Rates Using Imaging Fourier Transform Spectrometry," Chemical, Biological, Radiological, Nuclear, and Explosives (CBRNE) Sensing XII, Apr. 25-29, 2011, SPIE Proceedings vol. 8018, pp. 1-13.

Hayden et al., "Determination of Trace-Gas Amounts in Plumes by the Use of Orthogonal Digital Filtering of Thermal-Emission Spectra", Applied Optics, Jun. 1, 1996, vol. 35, No. 16, pp. 2802-2809.

Hirsch et al., "Detection of Gaseous Plumes in IR Hyperspectral Images Using Hierarchical Clustering", Applied Optics, Sep. 1, 2007, vol. 46, No. 25, pp. 6368-6374.

Johnston et al., "A Real-Time FPGA Implementation of a Barrel Distortion Correction Aglorithm", Projects, 2003, vol. 10, pp. 91-96.

Karion et al., "Methane Emissions Estimate from Airborne Measurements Over a Western United States Natural Gas Field", Geophysical Research Letters, 2013, vol. 40, pp. 4393-4397.

Keshava et al., "A Survey of Spectral Unmixing Algorithms", Lincoln Laboratory Journal, 2003, vol. 14, No. 1, pp. 55-78.

Kester et al., "A Real-Time Gas Cloud Imaging Camera for Fugitive Emission Detection and Monitoring", Imaging and Applied Optics Technical Digest, 2012, pp. 3.

Kester et al., "Development of Image Mappers for Hyperspectral Biomedical Imaging Applications", Applied Optics, Apr. 1, 2010, vol. 49, No. 10, pp. 1886-1899.

Kester et al., "High Numerical Aperture Microendoscope Objective for a Fiber Confocal Reflectance Microscope", Optics Express, Mar. 5, 2007, vol. 15. No. 5, pp. 2409-2420.

Kester et al., "Low Cost, High Performance, Self-Aligning Miniature Optical Systems", Applied Optics, Jun. 20, 2009, vol. 48, No. 18, pp. 3375-3384.

Kester et al., "Real-Time Snapshot Hyperspectral Imaging Endoscope", Journal of Biomedical Optics, May 2011, vol. 16, No. 5, pp. 056005-1-056005-12.

Kudenov et al., "Fourier Transform Channeled Spectropolarimetry in the MWIR", Optics Express, Oct. 1, 2007, vol. 15, No. 20, pp. 12792-12805.

Kudenov et al., "Snapshot Imaging Mueller Matrix Polarimeter Using Polarization Gratings", Optics Letters, Apr. 15, 2012, vol. 37, No. 8, pp. 1367-1369.

Landau et al., "Design and Evaluation of an Ultra-Slim Objective for in-vivo Deep Optical Biopsy", Optics Express, Mar. 1, 2010, vol. 18, No. 5, pp. 4758-4775.

Levi, Michael A., "Comment on 'Hydrocarbon Emissions Characterization in the Colorado Front Range: A Pilot Study' by Gabrielle Pétron et al.", Journal of Geophysical Research, 2012, vol. 117, No. D21203, pp. 1-5.

Levi, Michael A., "Reply to "'Reply to Comment on 'Hydrocarbon Emissions Characterization in the Colorado Front Range—A Pilot Study' by Michael A. Levi'" by Gabrielle Pétron et al.", Journal of Geophysical Research: Atmospheres, 2013, vol. 118, pp. 3044-3046.

Low et al., "Remote Sensing and Characterization of Stack Gases by Infrared Spectroscopy. An Approach by Using Multiple-Scan Interferometry", Environmental Science & Technology, Jan. 1967, vol. 1, No. 1, pp. 73-74.

Luo et al., "Fast Processing of Imaging Spectrometer Data Cube Based on FPGA Design", MIPPR 2007: Multispectral Image Processing, Proceedings of SPIE vol. 6787, pp. 7.

(56) References Cited

OTHER PUBLICATIONS

Manolakis et al., "Long-Wave Infrared Hyperspectral Remote Sensing of Chemical Clouds", IEEE Signal Processing Magazine, Jul. 2014, vol. 31, No. 4, pp. 120-141.
Mathews, "Design and Fabrication of a Low-Cost, Multispectral Imaging System," Applied Optics, 2008, pp. F71-F76, vol. 47.
Naranjo et al., "IR Gas Imaging in an Industrial Setting," Thermosense XXXII, Published in SPIE Proceedings vol. 7661, May 4, 2010, pp. 1-8.
Nguyen et al., "Snapshot 3D Optical Coherence Tomography System using Image Mapping Spectrometer", Biomedical Optics and 3D Imaging OSA, 2012, pp. 3.
Niu et al., "New Approach to Remote Gas-Phase Chemical Quantification: Selected-Band Algorithm", Optical Engineering, Feb. 2014, vol. 53, No. 2, pp. 021111-1-021111-10.
"Oil and Natural Gas Sector Leaks", U.S. EPA Office of Air Quality Planning and Standards (OAQPS), Review Panel, Apr. 2014, pp. 63.
Pétron et al., "Hydrocarbon Emissions Characterization in the Colorado Front Range: A Pilot Study", Journal of Geophysical Research, 2012, vol. 117, No. D04304, pp. 1-19.
Pétron et al., "Reply to Comment on 'Hydrocarbon Emissions Characterization in the Colorado Front Range—A Pilot Study' by Michael A. Levi", Journal of Geophysical Research: Atmospheres, 2013, vol. 118, pp. 236-242.
Pisano et al., "Thermal Illuminators for Far-Infrared and Submillimeter Astronomical Instruments," Applied Optics, Jun. 1, 2005, vol. 44, No. 16, pp. 3208-3217.
Polak et al., "Passive Fourier-Transform Infrared Spectroscopy of Chemical Plumes: An Algorithm for Quantitiative Interpretation and Real-Time Background Removal", Applied Optics, Aug. 20, 1995, vol. 34, No. 24, pp. 5406-5412.
Sandsten et al., "Volume Flow Calculations on Gas Leaks Imaged with Infrared Gas-Correlation," Optics Express, 2012, vol. 20, No. 18, pp. 20318-20329.
Shogenji et al., "Multispectral Imaging Using Compact Compound Optics," Optics Express, Apr. 19, 2004, vol. 12, No. 8, pp. 1643-1655.
Walter Jr., et al., "Detection of Atmospheric Pollutants: a Correlation Technique", Applied Optics, Jun. 1975, vol. 14, No. 6, pp. 1423-1428.
Williams et al., "Dual-Band MWIR/LWIR Radiometer for Absolute Temperature Measurements," SPIE Thermosense Conference XXVIII—Manuscript 6205-23, Apr. 18, 2006, 13 pages.
Young et al., "An In-Scene Method for Atmospheric Compensation of Thermal Hyperspectral Data", Journal of Geophysical Research, 2002, vol. 107, No. D24, pp. 14-1-14-20.
Zheng et al., "A Static Multiplex Fabry-Perot Spectrometer", Sensors, Cameras, and Systems for Industrial/Scientific Applications X, Proceedings of SPIE-IS&T Electronic Imaging, SPIE vol. 7249, 2009, pp. 8.
Zheng et al., "Analytic-Domain Lens Design with Proximate Ray Tracing", Journal of the Optical Society of America A, Aug. 2010, vol. 27, No. 8, pp. 1791-1802.
Office Action received in U.S. Appl. No. 14/543,692 dated Nov. 3, 2015 in 7 pages.
Office Action received in U.S. Appl. No. 14/539,899 dated Mar. 26, 2015 in 6 pages.
Office Action received in U.S. Appl. No. 14/539,899 dated Dec. 11, 2015 in 9 pages.
Amendment and Office Action Response submitted in U.S. Appl. No. 14/539,899 dated Aug. 26, 2015 in 8 pages.
Extended European Search Report received in European Application No. 14192862.2 dated Mar. 30, 2015 in 10 pages.
International Search Report in PCT Application No. PCT/US2013/041278 dated Aug. 27, 2013 in 4 pages.
International Preliminary Report on Patentability in PCT Application No. PCT/US2013/041278 dated Nov. 27, 2014 in 10 pages.
Extended European Search Report received in European Application No. 15165877.0 dated Aug. 10, 2015 in 12 pages.
Interview Summary received in U.S. Appl. No. 14/543,692 dated Feb. 17, 2016 in 5 pages.
Extended European Search Report received in European Application No. EP 15165880.4 dated Nov. 24, 2015 in 8 pages.
Preliminary Amendment as filed in U.S. Patent Application No. 14/700,567 dated Jul. 10, 2015 in 6 pages.
Preliminary Amendment as filed in U.S. Appl. No. 14/700,791 dated Jul. 13, 2015 in 8 pages.
Preliminary Amendment as filed in U.S. Appl. No. 14/792,477 dated Dec. 21, 2015 in 7 pages.
Gålfalk et al., "Making Methane Visable", Nature Climate Change, Apr. 2016, vol. 6, pp. 426-430.
Gålfalk et al., "Making Methane Visable", *Supplementary Information*, Nature Climate Change, 2015, pp. 1-14.
Hadlington, Simon, "New Camera Makes Methane Visible", Chemistry World, http://web.archive.org/web/20160305234907/http://www.rsc.org/chemistryworld/2015/12/methane-camera-infrared-greenhouse-gas, Dec. 14, 2015, pp.
TELOPS, "Hyper-Cam", http://web.archive.org/web/20160608180941/http://www.telops.com/en/hyperspectral-cameras/hyper-cam as archived Jun. 8, 2016 in 2 pages.
TELOPS, "Innovative Infrared Imaging", http://web.archive.org/web/20160603212729/http://www.telops.com/en/ as archived Jun. 3, 2016 in 2 pages.
Response to Office Action as filed in U.S. Appl. No. 14/543,692 dated May 2, 2016 in 9 pages.
Office Action received in U.S. Appl. No. 14/543,692 dated Jun. 1, 2016 in 18 pages.
Miscellaneous Communication dated Aug. 24, 2016 filed in U.S. Appl. No. 14/700,567.
Office Action received in E.P. Application No. 14192862.2 dated Apr. 19, 2016 in 6 pages.
Rebellion Photonics, "Gas Cloud Imaging Camera: A Breakthrough in Leak Monitoring for the Rig & Refinery Safety Market", Presentation at SPIE Defense Security and Sensing, 28 pages, Apr. 29-May 3, 2013.
Brochure provided by Lofty Designs to Rebellion Photonics on Oct. 31, 2012 as noted from the email. Subsequent to that date brochure was used in connection with potential customers.
"Directed Inspection and Maintenance at Gas Processing Plants and Booster Stations," United States Environmental Protection Agency Air and Radiation (6202J), EPA430-B-03-018, Oct. 2003 available at https://www3.epa.gov/gasstar/documents/ll_dimgasproc.pdf.
Adams, et al., "Advances in Detectors: Hot IR sensors improve IR camera size, weight, and power", Laser Focus World, vol. 50, Issue 01, Jan. 17, 2014, 6 pages. Also available at http://www.ircameras.com/articles/advances-detectors-hot-ir-sensors-improve-ir-camera-size-weight-power.
Amendment as filed in U.S. Appl. No. 14/539,899 dated Jun. 9, 2016 in 6 pages.
Notice of Allowance received in U.S. Appl. No. 14/539,899 dated Jun. 21, 2016 in 17 pages.
Notice of Allowance received in U.S. Appl. No. 14/700,791 dated Jun. 9, 2016 in 11 pages.
Preliminary Amendment as filed in U.S. Appl. No. 15/166,092 dated Aug. 15, 2016 in 7 pages.
Response to Final Action as filed in U.S. Appl. No. 14/543,692 dated Nov. 30, 2016 in 12 pages.
International Search Report in PCT Application No. PCT/US2016/034455 dated Oct. 24, 2016 in 12 pages.
Notice of Allowance received in U.S. Appl. No. 14/539,899 dated Oct. 31, 2016 in 10 pages.
Notice of Allowance received in U.S. Appl. No. 14/543,692 dated Dec. 9, 2016 in 12 pages.
Notice of Allowance received in U.S. Appl. No. 14/700,791 dated Sep. 30, 2016 in 19 pages.

* cited by examiner

DIVIDED-APERTURE INFRA-RED SPECTRAL IMAGING SYSTEM

CROSS-REFERENCE TO RELATED APPLICATIONS

The present application claims benefit under 35 U.S.C. §119(e) of U.S. Provisional Application No. 61/903,075, filed on Nov. 12, 2013 and titled "DIVIDED-APERTURE INFRA-RED SPECTRAL IMAGING SYSTEM". The disclosure of the above identified provisional patent application is incorporated by reference herein in its entirety.

TECHNICAL FIELD

The present invention generally relates to a system and method for gas cloud detection and, in particular, to a system and method of detecting spectral signatures of chemical compositions in a mid- and long-wave infrared spectral region.

DESCRIPTION OF THE RELATED TECHNOLOGY

Spectral imaging systems and methods have applications in a variety of fields. Spectral imaging systems and methods obtain a spectral image of a scene in one or more regions of the electromagnetic spectrum to detect phenomena, identify material compositions or characterize processes. The spectral image of the scene can be represented as a three-dimensional data cube where two axes of the cube represent two spatial dimensions of the scene and a third axes of the data cube represents spectral information of the scene in different wavelength regions. The data cube can be processed using mathematical methods to obtain information about the scene. Some of the existing spectral imaging systems generate the data cube by scanning the scene in the spatial domain (e.g., by moving a slit across the horizontal dimensions of the scene) and/or spectral domain (e.g., by scanning a wavelength dispersive element to obtain images of the scene in different spectral regions). Such scanning approaches acquire only a portion of the full data cube at a time. These portions of the full data cube are stored and then later processed to generate a full data cube.

SUMMARY

The systems, methods and devices of this disclosure each have several innovative aspects, no single one of which is solely responsible for the desirable attributes disclosed herein.

Various embodiments of the systems described herein provide an infrared (IR) imaging system for determining a concentration of a target chemical species in an object (e.g., a gas plume). The imaging system includes (i) an optical system, having an optical focal plane array (FPA) unit configured to receive IR radiation from the object along at least two or more optical channels defined by components of the optical system, the at least two or more optical channels being spatially and spectrally different from one another; and (ii) a processor or processing electronics configured to acquire multispectral optical data representing said target chemical species from the received IR radiation in a single occurrence of data acquisition (or snapshot). The optical FPA unit includes an array of photo-sensitive devices that are disposed at the focus of one or more lenses. In various embodiments, the array of photo-sensitive devices can include a two-dimensional imaging sensor that is sensitive to radiation having wavelengths between 1 µm and 20 µm (for example, in mid infra-red wavelength range, long infra-red wavelength range, visible wavelength range, etc.). In various embodiments, the array of photo-sensitive devices can include CCD or CMOS sensors, bolometers or other detectors that are sensitive to infra-red radiation. The optical system may include an optical aperture (a boundary of which is defined to circumscribe or encompass the at least two or more spatially distinct optical channels) and one or more optical filters. In various implementations, the one or more optical filters can comprise at least two spectrally-multiplexed filters. Each of these optical filters can be associated with one of the at least two or more optical channels and configured to transmit a portion of the IR radiation received in the associated optical channel. In various embodiments, the one or more optical filters can be spectrally multiplexed and may include, for example, at least one of a longpass optical filter and a shortpass optical filter, or a band pass filter (with or without a combination with another filter such as a notch filter, for example). The optical system may further include at least two reimaging lenses. The at least two reimaging lenses, for example each of the reimaging lens, may be disposed to transmit IR radiation (for example, between about 1 micron and about 20 microns), that has been transmitted through a corresponding optical filter towards the optical FPA unit. In one embodiment, the optical FPA unit is positioned to receive IR radiation from the object through the at least two reimaging lenses to form respectively-corresponding two or more sets of imaging data representing the object. The processor or processing electronics is configured to acquire this optical data from the two or more sets of imaging data. In various embodiments of the imaging systems, the FPA unit may be devoid of cooling systems. In various embodiments, two or more of the array of photo-sensitive devices may be uncooled. In some embodiments, the system further comprises two or more temperature-controlled shutters removably positioned to block IR radiation incident onto the optical system from the object.

Also disclosed herein is an implementation of a method of operating an infrared (IR) imaging system. The method includes receiving IR radiation from an object through at least two optical channels defined by components of an optical system of the IR imaging system, which at least two optical channels are spatially and spectrally different from one another. The method further includes transmitting the received IR radiation towards an optical focal plane array (FPA) unit that is not being cooled in the course of normal operation. For example, in various embodiments of the imaging systems, the FPA unit may be devoid of cooling systems. In various embodiments, two or more of the array of photo-sensitive devices may be uncooled. Some embodiments further comprise removably positioning at least one of at least two temperature-controlled shutters in front of the optical system to block IR radiation incident onto the optical system from the object.

Various innovative aspects of the subject matter described in this disclosure can be implemented in the following embodiments:

Embodiment 1

An infrared (IR) imaging system, the imaging system comprising:
- a plurality of cameras;
- at least one thermal reference source having a known temperature placed in front of the plurality of cameras and configured to be imaged by the plurality of cameras; and
- a data-processing unit comprising a processor, the imaging system configured to:
- acquire with the plurality of cameras a plurality of frames having regions that correspond to the image of the reference source; and
- apply a dynamic calibration correction to the plurality of cameras to allow every camera in the plurality of cameras to be calibrated to agree with every other camera in the plurality imaging the reference source.

Embodiment 2

The system of Embodiment 1, wherein the plurality of cameras comprises a FPA unit and a plurality of lenses.

Embodiment 3

The system of any of Embodiments 1-2, wherein the FPA unit comprises one FPA or a plurality of FPAs.

Embodiment 4

The system of any of Embodiments 1-3, wherein the at least one thermal reference source has a known spectrum.

Embodiment 5

The system of any of Embodiments 1-4, further comprising an additional thermal reference source imaged by the plurality of cameras.

Embodiment 6

The system of any of Embodiments 1-5, wherein the additional reference source has a temperature and a spectrum different from the known temperature and the known spectrum of the at least one reference source.

Embodiment 7

The system of any of Embodiments 1-6, wherein the temperature of the additional thermal reference source is less than the known temperature.

Embodiment 8

The system of any of Embodiments 1-7, wherein the temperature of the additional thermal reference source is greater than the known temperature.

Embodiment 9

The system of any of Embodiments 1-8, wherein the at least one reference source is displaced away from a conjugate image plane of the plurality of cameras such that the image of the at least one reference source captured by the plurality of cameras is blurred.

Embodiment 10

The system of any of Embodiments 1-9, wherein the at least one reference source is positioned at a conjugate image plane of the plurality of cameras.

Embodiment 11

The system of any of Embodiments 1-10, further comprising a plurality of mirrors configured to image the at least one reference source onto the plurality of cameras.

Embodiment 12

The system of any of Embodiments 1-11, wherein the plurality of mirrors are disposed outside a central field of view of the plurality of cameras.

Embodiment 13

The system of any of Embodiments 1-12, further comprising a first and a second temperature-controlled shutter removably positioned to block IR radiation incident on the system from reaching the plurality of cameras.

Embodiment 14

The system of any of Embodiments 1-13, wherein the system includes at least two spatially and spectrally different optical channels.

Embodiment 15

The system of any of Embodiments 1-14, wherein the system includes at least three optical channels.

Embodiment 16

The system of any of Embodiments 1-15, wherein the system includes at least four optical channels.

Embodiment 17

The system of any of Embodiments 1-16, wherein the system includes at least five optical channels.

Embodiment 18

The system of any of Embodiments 1-17, wherein the system includes at least six optical channels.

Embodiment 19

The system of any of Embodiments 1-18, wherein the system includes at least seven optical channels.

Embodiment 20

The system of any of Embodiments 1-19, wherein the system includes at least eight optical channels.

Embodiment 21

The system of any of Embodiments 1-20, wherein the system includes at least nine optical channels.

Embodiment 22

The system of any of Embodiments 1-21, wherein the system includes at least ten optical channels.

Embodiment 23

The system of any of Embodiments 1-22, wherein the system includes at least twelve optical channels.

Embodiment 24

The system of any of Embodiments 1-23, further comprising one or more sensors configured to measure a temperature of the at least one reference source.

Embodiment 25

The system of any of Embodiments 1-24, wherein the plurality of cameras is configured to image the same portion of the at least one reference source.

Embodiment 26

An infrared (IR) imaging system, the imaging system comprising:
  a plurality of cameras;
  a first temperature-controlled reference source imaged by the plurality of cameras;
  a second temperature-controlled reference source imaged by the plurality of cameras; and
  a data-processing unit comprising a processor, said data-processing unit configured to:
  acquire with the plurality of cameras a plurality of frames having regions that correspond to the image of the reference source; and
  dynamically calibrate the plurality of cameras so that various cameras imaging a scene are forced to agree on a temperature estimate of the first and second reference sources.

Embodiment 27

The imaging system of any of Embodiment 26, wherein the data-processing unit is configured to calculate a dynamic calibration correction and apply the correction to the plurality of cameras for each of the plurality of frames.

Embodiment 28

The system of any of Embodiments 26-27, wherein the first reference source is maintained at a first temperature.

Embodiment 29

The system of any of Embodiments 26-28, wherein the second reference source is maintained at a second temperature.

Embodiment 30

The system of any of Embodiments 26-29, wherein the first temperature is greater than the second temperature.

Embodiment 31

The system of any of Embodiments 26-30, wherein the first temperature is less than the second temperature.

Embodiment 32

The system of any of Embodiments 26-31, wherein the first and the second reference sources are displaced away from a conjugate image plane of the plurality of cameras such that the image of the first and the second reference sources captured by the plurality of cameras is blurred.

Embodiment 33

The system of any of Embodiments 26-32, wherein the first and the second reference sources are positioned at a conjugate image plane of the plurality of cameras.

Embodiment 34

The system of any of Embodiments 26-33, further comprising:
  a first mirror configured to image the first reference onto the plurality of cameras; and
  a second mirror configured to image the second reference source onto the plurality of cameras.

Embodiment 35

The system of any of Embodiments 26-34, further comprising a first and a second temperature-controlled shutter removably positioned to block IR radiation incident on the system from reaching the plurality of cameras.

Embodiment 36

The system of any of Embodiments 26-35, wherein the system includes at least two spatially and spectrally different optical channels.

Embodiment 37

The system of any of Embodiments 26-36, wherein the system includes at least four optical channels.

Embodiment 38

The system of any of Embodiments 26-37, wherein the system includes at least six optical channels.

Embodiment 39

The system of any of Embodiments 26-38, wherein the system includes at least eight optical channels.

Embodiment 40

The system of any of Embodiments 26-39, wherein the system includes at least ten optical channels.

Embodiment 41

The system of any of Embodiments 26-40, wherein the system includes at least twelve optical channels.

Embodiment 42

The system of any of Embodiments 26-41, further comprising one or more sensors configured to measure a temperature of the first or the second reference source.

Embodiment 43

The system of any of Embodiments 26-42, wherein the plurality of cameras is configured to image the same portion of the first reference source and wherein plurality of cameras is configured to image the same portion of the second reference source.

Embodiment 44

An infrared (IR) imaging system, the imaging system comprising:
- a plurality of cameras;
- a reference having an unknown temperature configured to be imaged by the plurality of cameras; and
- a data-processing unit comprising a processor, the imaging system configured to:
- acquire with the plurality of cameras a plurality of frames having regions that correspond to the image of the reference;
- calculate a dynamic calibration correction using a temperature measured by one of the cameras in the plurality of cameras as a reference temperature; and
- apply the calibration correction to the other cameras in the plurality of cameras to match the temperature estimate of the other cameras in the plurality of cameras with the reference temperature.

Embodiment 45

The system of any of Embodiment 44, wherein the reference is displaced away from a conjugate image plane of the plurality of cameras such that the image of the reference source captured by the plurality of cameras is blurred.

Embodiment 46

The system of any of Embodiments 44-45, wherein the reference is positioned at a conjugate image plane of the plurality of cameras.

Embodiment 47

The system of any of Embodiments 44-46, further comprising a plurality of mirrors configured to image the reference onto the plurality of cameras.

Embodiment 48

The system of any of Embodiments 44-47, further comprising a first and a second temperature-controlled shutter removably positioned to block IR radiation incident on the system from reaching the plurality of cameras.

Embodiment 49

The system of any of Embodiments 44-48, wherein the system includes at least two spatially and spectrally different optical channels.

Embodiment 50

The system of any of Embodiments 44-49, wherein the system includes at least three optical channels.

Embodiment 51

The system of any of Embodiments 44-50, wherein the system includes at least four optical channels.

Embodiment 52

The system of any of Embodiments 44-51, wherein the system includes at least five optical channels.

Embodiment 53

The system of any of Embodiments 44-52, wherein the system includes at least six optical channels.

Embodiment 54

The system of any of Embodiments 44-52, wherein the system includes at least seven optical channels.

Embodiment 55

The system of any of Embodiments 44-53, wherein the system includes at least eight optical channels.

Embodiment 56

The system of any of Embodiments 44-54, wherein the system includes at least nine optical channels.

Embodiment 57

The system of any of Embodiments 44-55, wherein the system includes at least ten optical channels.

Embodiment 58

The system of any of Embodiments 44-56, wherein the system includes at least twelve optical channels.

Embodiment 59

The system of any of Embodiments 44-57, wherein the plurality of cameras is configured to image the same portion of the reference.

Embodiment 60

An infrared (IR) imaging system, the imaging system comprising:
- an optical system including an optical focal plane array (FPA) unit, the optical system includes components associated with at least two optical channels, said at least two optical channels being spatially and spectrally different from one another, each of the at least two optical channels positioned to transfer IR radiation incident on the optical system towards the optical FPA unit, the optical FPA unit comprising at least two detector arrays disposed at a distance from two corresponding focusing lenses;
- at least one thermal reference having a known temperature, wherein radiation emitted from the at least one reference is directed towards the optical FPA unit and imaged by the at least two detector arrays; and a data-processing unit, said data-processing unit configured to:

acquire a plurality of frames with the at least two detector arrays having regions in the plurality of image frames that correspond to the image of the reference; and dynamically calibrate the at least two detector arrays to address a difference in the temperature estimate of the reference between the two detector arrays.

Embodiment 61

The system of any of Embodiment 60, wherein the at least one thermal reference has a known spectrum.

Embodiment 62

The system of any of Embodiments 60-61, further comprising an additional thermal reference, wherein radiation from the additional reference is directed towards the optical FPA unit and imaged by the at least two detector arrays.

Embodiment 63

The system of any of Embodiments 60-62, wherein the additional reference has a temperature and a spectrum different from the known temperature and the known spectrum of the at least one reference source.

Embodiment 64

The system of any of Embodiments 60-63, wherein the temperature of the additional thermal reference is less than the known temperature.

Embodiment 65

The system of any of Embodiments 60-64, wherein the temperature of the additional thermal reference is greater than the known temperature.

Embodiment 66

The system of any of Embodiments 60-65, wherein the at least one reference is displaced away from a conjugate image plane of the at least two detector arrays such that the image of the at least one reference captured by the at least two detector arrays is defocused.

Embodiment 67

The system of any of Embodiments 60-66, wherein the at least one reference is positioned at a conjugate image plane of the at least two detector arrays such that the image of the at least one reference captured by the at least two detector arrays is focused.

Embodiment 68

The system of any of Embodiments 60-67, further comprising at least two reflecting elements configured to direct radiation from the at least one reference source toward the at least two detector arrays.

Embodiment 69

The system of any of Embodiments 60-68, wherein the at least two reflecting elements are disposed outside a central field of view of the at least two detector arrays.

Embodiment 70

The system of any of Embodiments 60-69, further comprising a third detector array disposed between the at least two detector arrays.

Embodiment 71

The system of any of Embodiments 60-70, wherein the data-processing unit is configured to:

acquire a plurality of frames using the third detector array; and dynamically calibrate the third detector array to match a temperature estimate of the third detector array with the temperature estimates of the at least two detector arrays.

Embodiment 72

The system of any of Embodiments 60-71, wherein radiation emitted from the at least one reference source is not imaged by the third detector array.

Embodiment 73

The system of any of Embodiments 60-72, wherein the third detector array has a field of view greater than a field of view of the at least two detector arrays.

Embodiment 74

The system of any of Embodiments 60-73, wherein the at least one reference is imaged by the third detector array.

Embodiment 75

The system of any of Embodiments 60-74, further comprising a third reflecting element disposed outside the field of view of the at least two detector arrays and configured to image the at least one reference onto the third detector array.

Embodiment 76

The system of any of Embodiments 60-75, further comprising a first and a second temperature-controlled element removably positioned to block IR radiation incident on the optical system from reaching the optical FPA unit.

Embodiment 77

The system of any of Embodiments 60-76, wherein the optical system includes components associated with three optical channels.

Embodiment 78

The system of any of Embodiments 60-77 wherein the optical system includes components associated with four optical channels.

Embodiment 79

The system of any of Embodiments 60-78, wherein the optical system includes components associated with six optical channels.

Embodiment 80

The system of any of Embodiments 60-79, wherein the optical system includes components associated with eight optical channels.

Embodiment 81

The system of any of Embodiments 60-80, wherein the optical system includes components associated with ten optical channels.

Embodiment 82

The system of any of Embodiments 60-81, wherein the optical system includes components associated with twelve optical channels.

Embodiment 83

The system of any of Embodiments 60-82, wherein the optical system includes components associated with sixteen optical channels.

Embodiment 84

The system of any of Embodiments 60-83, wherein the optical system includes components associated with twenty four optical channels.

Embodiment 85

The system of any of Embodiments 60-84, wherein each of the at least two detector arrays is configured to image the same portion of the at least one reference so as to consistently provide a common reference temperature.

Embodiment 86

The system of any of Embodiments 60-85, wherein the data-processing unit comprises processing electronics.

Embodiment 87

The system of any of Embodiments 60-86, wherein the data-processing unit comprises a processor.

Embodiment 88

The system of any of Embodiments 60-87, wherein the data-processing unit comprises one or more processors.

Embodiment 89

An infrared (IR) imaging system, the imaging system comprising: an optical system including an optical focal plane array (FPA) unit, the
  optical system including at least two optical channels, said at least two optical channels being spatially and spectrally different from one another, each of the at least two optical channels positioned to transfer IR radiation incident on the optical system towards the optical FPA unit, the optical FPA unit comprising at least two detector arrays disposed at a distance from two corresponding focusing lenses;
  a first temperature-controlled reference imaged by the at least two detector arrays;
  a second temperature-controlled reference imaged by the at least two detector arrays; and
  a data-processing unit configured to:
  acquire a plurality of frames with the at least two detector arrays having regions in the plurality of image frames that correspond to the image of the first and second references; and
  dynamically calibrate the at least two detector arrays to address a difference in a temperature estimate of the first and second references between the two detector arrays.

Embodiment 90

The system of Embodiment 89, wherein the first reference is maintained at a first temperature.

Embodiment 91

The system of any of Embodiments 89-90, wherein the second reference is maintained at a second temperature.

Embodiment 92

The system of any of Embodiments 89-91, wherein the first temperature is greater than the second temperature.

Embodiment 93

The system of any of Embodiments 89-92, wherein the first temperature is less than the second temperature.

Embodiment 94

The system of any of Embodiments 89-93, wherein the first and the second references are displaced away from a conjugate image plane of the at least two detector arrays such that the image of the first and the second references captured by the at least two detector arrays is defocused.

Embodiment 95

The system of any of Embodiments 89-94, wherein the first and the second references are positioned at a conjugate image plane of the at least two detector arrays such that the image of the first and the second references captured by the at least two detector arrays is focused.

Embodiment 96

The system of any of Embodiments 89-95, further comprising:
  a first reflecting element configured to direct radiation from the first reference toward the at least two detector arrays; and a second reflecting element configured to direct radiation from the second reference toward the at least two detector arrays.

Embodiment 97

The system of any of Embodiments 89-96, wherein the first reflecting element is disposed outside a field of view of the at least two detector arrays.

Embodiment 98

The system of any of Embodiments 89-97, wherein the second reflecting element is disposed outside a field of view of the at least two detector arrays.

Embodiment 99

The system of any of Embodiments 89-98, further comprising a third detector array disposed between the at least two detector arrays.

Embodiment 100

The system of any of Embodiments 89-99, wherein the data-processing unit is configured to:
acquire a plurality of frames using the third detector array; and
dynamically calibrate the third detector array to address a difference in the temperature estimate of the first and second references between the third detector array and the two detector arrays.

Embodiment 101

The system of any of Embodiments 89-100, wherein the first and second references are not imaged by the third detector array.

Embodiment 102

The system of any of Embodiments 89-101, wherein the third detector array has a field of view greater than a field of view of the at least two detector arrays.

Embodiment 103

The system of any of Embodiments 89-102, wherein r first and second references are imaged by the third detector array.

Embodiment 104

The system of any of Embodiments 89-103, further comprising a third reflecting element disposed outside the field of view of the at least two detector arrays and configured to image the first and second references onto the third detector array.

Embodiment 105

The system of any of Embodiments 89-104, further comprising a first and a second temperature-controlled element removably positioned to block IR radiation incident on the optical system from reaching the optical FPA unit.

Embodiment 106

The system of any of Embodiments 89-105, wherein the optical system includes components associated with three optical channels.

Embodiment 107

The system of any of Embodiments 89-106, wherein the optical system includes components associated with four optical channels.

Embodiment 108

The system of any of Embodiments 89-107, wherein the optical system includes components associated with five optical channels.

Embodiment 109

The system of any of Embodiments 89-108, wherein the optical system includes components associated with six optical channels.

Embodiment 110

The system of any of Embodiments 89-109, wherein the optical system includes components associated with seven optical channels.

Embodiment 111

The system of any of Embodiments 89-110, wherein the optical system includes components associated with eight optical channels.

Embodiment 112

The system of any of Embodiments 89-111, wherein the optical system includes components associated with ten optical channels.

Embodiment 113

The system of any of Embodiments 89-112, wherein the optical system includes components associated with twelve optical channels.

Embodiment 114

The system of any of Embodiments 89-113, wherein each of the at least two detector arrays is configured to image the same portion of the first reference source so as to consistently provide a common first reference temperature and wherein each of the at least two detector arrays is configured to image the same portion of the second reference source so as to consistently provide a common second reference temperature.

Embodiment 115

The system of any of Embodiments 89-114, further comprising a temperature controller configured to control the temperature of the first or second reference.

Embodiment 116

The system of any of Embodiments 89-115, further comprising one or more sensors configured to measure a temperature of the first or the second reference.

Embodiment 117

The system of any of Embodiments 89-116, wherein the one or more sensors are configured to communicate the measured temperature of the first or the second reference to a temperature controller.

Embodiment 118

The system of any of Embodiments 89-117, wherein the one or more sensors are configured to communicate the measured temperature of the first or the second reference to the data-processing unit.

Embodiment 119

The system of any of Embodiments 89-118, wherein the first or the second reference is associated with a heater.

Embodiment 120

The system of any of Embodiments 89-119, wherein the first or the second reference is associated with a cooler.

Embodiment 121

The system of any of Embodiments 89-120, wherein the data-processing unit comprises processing electronics.

Embodiment 122

The system of any of Embodiments 89-121, wherein the data-processing unit comprises a processor.

Embodiment 123

The system of any of Embodiments 89-122, wherein the data-processing unit comprises one or more processors.

Embodiment 124

An infrared (IR) imaging system, the imaging system comprising:
- an optical system including components associated with at least two optical channels, said at least two optical channels being spectrally different from one another, each of the at least two optical channels positioned to transfer IR radiation incident on the optical system towards a plurality of cameras;
- at least one calibration surface with unknown temperature and imaged by each of the at least two detectors; and
- a data-processing unit configured to:
- acquire a plurality of image frames with the plurality of cameras including the imaged surface; and
- adjust one or more parameters of the cameras in the plurality of cameras such that a temperature estimate of the calibration surface of the cameras in the plurality of cameras agree with each other.

Embodiment 125

The system of Embodiment 124, wherein the one or more parameters is associated with a gain of the cameras in the plurality of cameras.

Embodiment 126

The system of any of Embodiments 124-125, wherein the one or more parameters is associated with a gain offset of the cameras in the plurality of cameras.

Embodiment 127

The system of any of Embodiments 124-126, wherein the calibration surface is displaced away from a conjugate image plane of the plurality of cameras such that an image of the surface is defocused.

Embodiment 128

The system of any of Embodiments 124-127, wherein the calibration surface is positioned at a conjugate image plane of the plurality of cameras such that an image of the surface is focused.

Embodiment 129

The system of any of Embodiments 124-128, further comprising at least one reflecting element configured to image the surface onto the plurality of cameras.

Embodiment 130

The system of any of Embodiments 124-129, further comprising a first and a second temperature-controlled element removably positioned to block IR radiation incident on the optical system from reaching the plurality of cameras.

Embodiment 131

The system of any of Embodiments 124-130, wherein the optical system includes components associated with three optical channels.

Embodiment 132

The system of any of Embodiments 124-131, wherein the optical system includes components associated with four optical channels.

Embodiment 133

The system of any of Embodiments 124-132, wherein the optical system includes components associated with six optical channels.

Embodiment 134

The system of any of Embodiments 124-133, wherein the optical system includes components associated with eight optical channels.

Embodiment 135

The system of any of Embodiments 124-134, wherein the optical system includes components associated with ten optical channels.

Embodiment 136

The system of any of Embodiments 124-135, wherein the optical system includes components associated with twelve optical channels.

Embodiment 137

The system of any of Embodiments 124-136, wherein the data-processing unit comprises processing electronics.

Embodiment 138

The system of any of Embodiments 124-137, wherein the data-processing unit comprises a processor.

Embodiment 139

The system of any of Embodiments 124-138, wherein the data-processing unit comprises one or more processors.

Embodiment 140

The system of any of Embodiments 124-139, wherein the calibration surface comprises a sidewall of a housing of the system.

Embodiment 141

An infrared (IR) imaging system, the imaging system comprising:
- at least four spatially and spectrally different optical channels configured to receive IR radiation from a common object, each of the at least four spatially and spectrally different optical channels comprising at least one imaging lens configured to image the object on a Focal Plane Array (FPA) unit; and
- processing electronics in communication with the FPA unit, wherein said infrared system is configured to:
- acquire multispectral optical data from the at least four different optical channels; and
- process the multispectral optical data to detect one or more target species present in the object.

Embodiment 142

The system of Embodiment 141, further comprising twelve optical channels.

Embodiment 143

The system of any of Embodiments 141-142, configured to simultaneously acquire multispectral optical data from the at least four different optical channels.

Embodiment 144

The system of any of Embodiments 141-143, further comprising a plurality of optical filters associated with the optical channels.

Embodiment 145

The system of any of Embodiments 141-144, wherein a number of optical filters is two.

Embodiment 146

The system of any of Embodiments 141-145, wherein a number of optical filters is three.

Embodiment 147

The system of any of Embodiments 141-146, wherein a number of optical filters is four.

Embodiment 148

The system of any of Embodiments 141-147, wherein the plurality of optical filters comprise at least one long pass (LP) filter.

Embodiment 149

The system of any of Embodiments 141-148, wherein the plurality of optical filters comprise multiple long pass (LP) filters.

Embodiment 150

The system of any of Embodiments 141-149, wherein the plurality of optical filters comprise at least one short pass (SP) filter.

Embodiment 151

The system of any of Embodiments 141-150, wherein the plurality of optical filters comprise multiple short pass (SP) filters.

Embodiment 152

The system of any of Embodiments 141-151, wherein the plurality of optical filters comprise at least one band pass (BP) filter.

Embodiment 153

The system of any of Embodiments 141-152, wherein the plurality of optical filters comprise at one short pass (SP) filter and one long pass (LP) filter.

Embodiment 154

The system of any of Embodiments 141-153, wherein the FPA unit comprises a plurality of FPAs.

Embodiment 155

The system of any of Embodiments 141-154, further comprising first and second temperature-controlled elements removably positioned to block IR radiation incident on the imaging system from reaching the FPA unit.

Embodiment 156

The system of any of Embodiments 141-155, further comprising a field reference configured for dynamically calibrating a plurality of the FPAs in the FPA unit.

Embodiment 157

The system of any of Embodiments 141-156, wherein the field reference is configured to obscure a peripheral region of an image generated by a plurality of the FPAs in the FPA unit.

Embodiment 158

The system of any of Embodiments 141-157, configured to compare spectral data in at least one of the four optical channels acquired at a first instant of time with spectral data in the at least one of the four optical channels acquired at a second instant of time to generate a temporal difference image.

Embodiment 159

The system of any of Embodiments 141-158, configured to use a difference between the multispectral optical data acquired by the two optical channels to correct parallax-induced imaging errors.

Embodiment 160

The system of any of Embodiments 141-159, configured to use a difference between the multispectral optical data acquired by the two optical channels to estimate a distance between the system and the object.

Embodiment 161

The system of any of Embodiments 141-160, configured to estimate a size of the object based on the estimated distance and an optical magnification factor of the two optical channels.

Embodiment 162

The system of any of Embodiments 141-161, configured to compare spectral data in one of the at least four optical channels with spectral data in another one of the at least four optical channels to generate a spectral difference image.

Embodiment 163

The system of any of Embodiments 141-162, further comprising a visible light imaging sensor.

Embodiment 164

The system of any of Embodiments 141-163, configured to use the visible light imaging sensor to compensate for motion-induced imaging errors.

Embodiment 165

The system of any of Embodiments 141-164, configured to process the multispectral optical data by cross-correlating multispectral optical data from at least one of the optical channels with a reference spectrum.

Embodiment 166

The system of any of Embodiments 141-165, configured to process the multispectral optical data using spectral unmixing.

Embodiment 167

The system of any of Embodiments 141-166, further comprising five optical channels.

Embodiment 168

The system of any of Embodiments 141-167, further comprising six optical channels.

Embodiment 169

The system of any of Embodiments 141-168, further comprising seven optical channels.

Embodiment 170

The system of any of Embodiments 141-169, further comprising eight optical channels.

Embodiment 171

The system of any of Embodiments 141-170, further comprising nine optical channels.

Embodiment 172

The system of any of Embodiments 141-171, further comprising ten optical channels.

Embodiment 173

The system of any of Embodiments 141-172, further comprising eleven optical channels.

Embodiment 174

The system of any of Embodiments 141-173, wherein a number of optical filters is five.

Embodiment 175

The system of any of Embodiments 141-174, wherein a number of optical filters is six.

Embodiment 176

The system of any of Embodiments 141-175, wherein a number of optical filters is seven.

Embodiment 177

The system of any of Embodiments 141-176, wherein a number of optical filters is eight.

Embodiment 178

The system of any of Embodiments 141-177, wherein a number of optical filters is nine.

Embodiment 179

The system of any of Embodiments 141-178, wherein a number of optical filters is ten.

Embodiment 180

The system of any of Embodiments 141-179, wherein a number of optical filters is eleven.

Embodiment 181

The system of any of Embodiments 141-180, wherein a number of optical filters is twelve.

Embodiment 182

The system of any of Embodiments 141-181, wherein the processing electronics comprises one or more processors.

Embodiment 183

The system of any of Embodiments 141-182, further comprising a thermal reference configured to be imaged onto the FPA unit such that a plurality of frames of the acquired multispectral optical data has an image of the thermal reference source.

Embodiment 184

The system of any of Embodiments 141-183, wherein the thermal reference has a known temperature.

Embodiment 185

The system of any of Embodiments 141-184, wherein the thermal reference is a temperature-controlled reference source.

Embodiment 186

The system of any of Embodiments 141-185, wherein the temperature-controlled reference source includes a heater.

Embodiment 187

The system of any of Embodiments 141-186, wherein the temperature-controlled reference source includes a cooler.

Embodiment 188

The system of any of Embodiments 141-187, further comprising a mirror configured to image the thermal reference onto the FPA unit.

Embodiment 189

The system of any of Embodiments 141-188, wherein a temperature of the thermal reference is unknown.

Embodiment 190

The system of any of Embodiments 141-189, wherein the thermal reference is a surface.

Embodiment 191

The system of any of Embodiments 141-190, wherein the surface comprises a wall of a housing of the system.

Embodiment 192

The system of any of Embodiments 141-191, wherein different optical channels receive IR radiation from the same portion of the thermal reference so as to consistently provide a common reference temperature.

Embodiment 193

The system of any of Embodiments 141-192, wherein a temperature of the same portion of the thermal reference is unknown.

Embodiment 194

The system of any of Embodiments 141-193, configured to acquire the multispectral optical data at a frame rate between about 5 Hz to about 200 Hz.

Embodiment 195

The system of any of Embodiments 141-194, wherein one or more of the at least four optical channels is configured to collect IR radiation to provide spectral data corresponding to a discrete spectral band located in the wavelength range between about 7.9 µm and about 8.4 µm.

Embodiment 196

The system of any of Embodiments 141-195, wherein each optical channel is configured to transfer spectrally distinct, two-dimensional image data of the common object to one or more imaging sensors.

Embodiment 196

The system of any of Embodiments 1-24, wherein the one or more sensors are configured to communicate the measured temperature of the at least one reference source to a temperature controller.

Embodiment 197

The system of any of Embodiments 1-24, wherein the one or more sensors are configured to communicate the measured temperature of the at least one reference source to the data-processing unit.

Embodiment 198

The system of any of Embodiments 26-42, wherein the one or more sensors are configured to communicate measured temperature of the first or the second reference to a temperature controller.

Embodiment 199

The system of any of Embodiments 26-42, wherein the one or more sensors are configured communicate the measured temperature of the first or the second reference to the data-processing unit.

Embodiment 200

An infrared (IR) imaging system for imaging a target species in an object, the imaging system comprising:
an optical system comprising an optical focal plane array (FPA) unit and defining a plurality of spatially and spectrally different optical channels to transfer IR radiation towards the optical FPA unit, each optical channel positioned to transfer a portion of the IR radiation incident on the optical system from the object towards the optical FPA unit; and a programmable processor configured to execute instructions stored in a tangible, non-transitory computer-readable storage medium, to acquire, in a single occurrence of data acquisition, multispectral optical data representing in spatial (x, y) and spectral ($\lambda$) coordinates said object and said target species from the IR radiation received at the optical FPA unit.

Embodiment 201

The system of Embodiment 200, wherein the multispectral data comprises a number of spectrally different images of the object obtained from IR image data transferred to the optical FPA unit by a corresponding optical channel.

Embodiment 202

The system of any of Embodiments 200-201, further comprising an optical filter corresponding to a particular optical channel and configured to transmit the portion of IR radiation towards the optical FPA unit.

Embodiment 203

The system of any of Embodiments 200-202, wherein the optical filter includes one of a longpass optical filter and a shortpass optical filter.

Embodiment 204

The system of any of Embodiments 200-203, further comprising one or more front objective lenses.

Embodiment 205

The system of any of Embodiments 200-204, wherein the optical system comprises a plurality of lenses, each lens corresponding to an optical channel.

Embodiment 206

The system of any of Embodiments 200-205, wherein each optical channel is defined at least in part by a corresponding filter and a corresponding lens.

Embodiment 207

The system of any of Embodiments 200-206, wherein the plurality of lenses comprises a lens array.

Embodiment 208

The system of any of Embodiments 200-207, further comprising a plurality of relay lenses configured to relay the IR radiation along the optical channels.

Embodiment 209

The system of any of Embodiments 200-208, further comprising a plurality of moveable temperature-controlled reference source removably positioned to block IR radiation incident onto the optical system from reaching the optical FPA unit.

Embodiment 210

The system of any of Embodiments 200-209, wherein the multispectral optical data from the plurality of optical channels is captured substantially simultaneously by the optical FPA unit.

Embodiment 211

The system of any of Embodiments 200-210, wherein the multispectral optical data from the plurality of optical channels is captured during one image frame acquisition by the optical FPA unit.

Embodiment 212

The system of any of Embodiments 200-211, further comprising first and second temperature-controlled moveable shutters removably positioned to block IR radiation incident onto the optical system from reaching the optical FPA unit.

Embodiment 213

The system of any of Embodiments 200-212, wherein the optical FPA unit is devoid of a cooling device.

Embodiment 214

The system of any of Embodiments 200-213, further comprising a filter array.

Embodiment 215

The system of any of Embodiments 200-214, wherein the processor is configured to execute instructions stored in a tangible, non-transitory computer-readable storage medium to acquire said optical data from the two or more sets of imaging data.

Embodiment 216

The system of any of Embodiments 200-215, wherein the processor is configured to execute instructions stored in a tangible, non-transitory computer-readable storage medium to process the acquired optical data to compensate for at least one of (i) parallax-induced differences between the two or more sets of imaging data and (ii) difference between the two or more sets of imaging data induced by changes in the object that are not associated with the target species.

Embodiment 217

The system of any of Embodiments 200-216, wherein the processor is configured to execute instructions stored in a tangible, non-transitory computer-readable storage medium to process the acquired optical data to generate a temporal reference image.

Embodiment 218

The system of any of Embodiments 200-217, wherein the processor is configured to execute instructions stored in a tangible, non-transitory computer-readable storage medium to use the temporal reference image to generate a temporal difference image.

Embodiment 219

The system of any of Embodiments 200-218, wherein the processor is configured to execute instructions stored in a tangible, non-transitory computer-readable storage medium to process the acquired optical data to estimate a volume of a gas cloud.

Embodiment 220

The system of any of Embodiments 200-219, wherein IR radiation measured at a pixel comprises a spectrum comprising a sum of component spectra, and wherein the processor is configured to execute instructions stored in a tangible, non-transitory computer-readable storage medium to unmix the spectrum.

Embodiment 221

The system of any of Embodiments 200-220, wherein the optical FPA unit includes a bolometer configured to operate without being cooled.

Embodiment 222

The system of any of Embodiments 200-221, further comprising a field reference for dynamically adjusting data output from the optical FPA unit.

Embodiment 223

The system of any of Embodiments 200-222, wherein the field reference comprises an array of field stops.

Embodiment 224

The system of any of Embodiments 200-223, wherein the field reference comprises a uniform temperature across its surface.

Embodiment 225

The system of any of Embodiments 200-224, wherein the field reference is adapted to obscure or block a peripheral portion of the IR radiation propagating from the object towards the optical FPA unit.

Embodiment 226

The system of any of Embodiments 200-225, further comprising a visible light imaging sensor.

Embodiment 227

The system of any of Embodiments 200-226, wherein the processor is configured to execute instructions stored in a tangible, non-transitory computer-readable storage medium to process data received from an imaging sensor to compensate for motion-induced imaging errors.

Embodiment 228

The system of any of Embodiments 200-227, wherein the processor is configured to execute instructions stored in a tangible, non-transitory computer-readable storage medium to process data received from the visible light imaging sensor to compensate for motion-induced imaging errors.

Embodiment 229

The system of any of Embodiments 200-228, wherein the processor is configured to execute instructions stored in a tangible, non-transitory computer-readable storage medium to construct, in the single occurrence of data acquisition, a multispectral data cube of the object, the multispectral data cube comprising a number of spectrally different images of the object, each spectrally different image comprising IR image data transferred to the optical FPA unit by a corresponding optical channel.

Embodiment 230

The system of any of Embodiments 200-229, wherein the portion of the IR radiation corresponds to a region of wavelengths of the spectrum of wavelengths, the region of wavelengths at least partially overlapping another region of wavelengths transferred by another optical channel.

Embodiment 231

An infrared (IR) imaging system, the imaging system comprising:
  a plurality of spatially and spectrally different optical channels, at least some of the plurality of optical channels configured to receive IR radiation from a common object, each of the plurality of spatially and spectrally different optical channels comprising at least one imaging lens configured to image the object on a Focal Plane Array (FPA) unit; and
  processing electronics in communication with the FPA unit,
  wherein said infrared system is configured to:
  acquire multispectral optical data from the plurality of different optical channels; and
  process the multispectral optical data to detect one or more target species present in the object, and
  wherein the system is further configured to compare spectral data in at least one of the plurality of optical channels acquired at a first instant of time with spectral data in at least one of the plurality of optical channels acquired at a second instant of time to generate a temporal difference image.

Embodiment 232

An infrared (IR) imaging system, the imaging system comprising:
  a plurality of spatially and spectrally different optical channels, at least some of the plurality of optical channels configured to receive IR radiation from a common object, each of the plurality of spatially and spectrally different optical channels comprising at least one imaging lens configured to image the object on a Focal Plane Array (FPA) unit; and
  processing electronics in communication with the FPA unit,
  wherein said infrared system is configured to:
  acquire multispectral optical data from the plurality of different optical channels; and
  process the multispectral optical data to detect one or more target species present in the object, and wherein the system is configured to use a difference between the multispectral optical data acquired by two optical channels to correct parallax-induced imaging errors.

Embodiment 232

The system of Embodiment 231, wherein spectral characteristics of the two optical channels are identical.

Embodiment 233

An infrared (IR) imaging system, the imaging system comprising:
a plurality of spatially and spectrally different optical channels, at least some of the plurality of optical channels configured to receive IR radiation from a common object, each of the plurality of spatially and spectrally different optical channels comprising at least one imaging lens configured to image the object on a Focal Plane Array (FPA) unit; and
processing electronics in communication with the FPA unit,
wherein said infrared system is configured to:
acquire multispectral optical data from the plurality of different optical channels; and
process the multispectral optical data to detect one or more target species present in the object, and
wherein the system is configured to use a difference between the multispectral optical data acquired by two optical channels to estimate a distance between the system and the object.

Embodiment 234

The system of Embodiment 233, wherein spectral characteristics of the two optical channels are identical.

Embodiment 235

An infrared (IR) imaging system, the imaging system comprising:
a plurality of spatially and spectrally different optical, at least some of the plurality of optical channels configured to receive IR radiation from a common object, each of the plurality of spatially and spectrally different optical channels comprising at least one imaging lens configured to image the object on a Focal Plane Array (FPA) unit;
a visible light imaging sensor; and
processing electronics in communication with the FPA unit,
wherein said infrared system is configured to:
acquire multispectral optical data from the plurality of different optical channels; and
process the multispectral optical data to detect one or more target species present in the object.

Embodiment 236

An infrared (IR) imaging system, the imaging system comprising:
a plurality of spatially and spectrally different optical, at least some of the plurality of optical channels configured to receive IR radiation from a common object, each of the plurality of spatially and spectrally different optical channels comprising at least one imaging lens configured to image the object on a Focal Plane Array (FPA) unit; and
processing electronics in communication with the FPA unit,
wherein said infrared system is configured to:
acquire multispectral optical data from the plurality of different optical channels; and
process the multispectral optical data to detect one or more target species present in the object, and
wherein the system is configured to compensate for motion-induced imaging errors.

Embodiment 237

An infrared (IR) imaging system, the imaging system comprising:
a plurality of spatially and spectrally different, at least some of the plurality of optical channels configured to receive IR radiation from a common object, each of the plurality of spatially and spectrally different optical channels comprising at least one imaging lens configured to image the object on a Focal Plane Array (FPA) unit; and
processing electronics in communication with the FPA unit,
wherein said infrared system is configured to:
acquire multispectral optical data from the plurality of different optical channels; and
process the multispectral optical data to detect one or more target species present in the object by cross-correlating multispectral optical data from at least one of the optical channels with a reference spectrum.

Embodiment 238

An infrared (IR) imaging system, the imaging system comprising:
a plurality of spatially and spectrally different optical, at least some of the plurality of optical channels configured to receive IR radiation from a common object, each of the plurality of spatially and spectrally different optical channels comprising at least one imaging lens configured to image the object on a Focal Plane Array (FPA) unit; and
processing electronics in communication with the FPA unit,
wherein said infrared system is configured to:
acquire multispectral optical data from the plurality of different optical channels; and
process the multispectral optical data to detect one or more target species present in the object by using spectral unmixing.

Embodiment 239

An infrared (IR) imaging system, the imaging system comprising:
an optical system including an optical focal plane array (FPA) unit, the optical system includes components associated with at least two optical channels, said at least two optical channels being spatially and spectrally different from one another, each of the at least two optical channels positioned to transfer IR radiation incident on the optical system towards the optical FPA unit, the optical FPA unit comprising at least two detector arrays disposed at a distance from two corresponding focusing lenses;

at least one thermal reference having a known temperature, wherein one of the at least two detector arrays is configured to image the at least one reference; and a data-processing unit, said data-processing unit configured to:

acquire a plurality of frames with one of the at least two detector arrays having regions in the plurality of image frames that correspond to the image of the reference; and dynamically calibrate another of the at least two detector array to match a temperature estimate of another of the at least two detector array with the temperature estimate of one of the at least two detector array.

Embodiment 240

The system of any of Embodiments 1-59, wherein the plurality of cameras are configured to acquire multispectral image data from an object continuously for a duration of time.

Embodiment 241

The system of any of Embodiments 1-59, comprising at least two spectrally and spatially distinct optical channels configured to transfer two-dimensional image data of an object to the plurality of cameras.

Details of one or more implementations of the subject matter described in this disclosure are set forth in the accompanying drawings and the description below. Other features, aspects, and advantages will become apparent from the description, the drawings and the claims. Note that the relative dimensions of the following figures may not be drawn to scale.

BRIEF DESCRIPTION OF THE DRAWINGS

Like reference numbers and designations in the various drawings indicate like elements.

DETAILED DESCRIPTION

Figure 1:
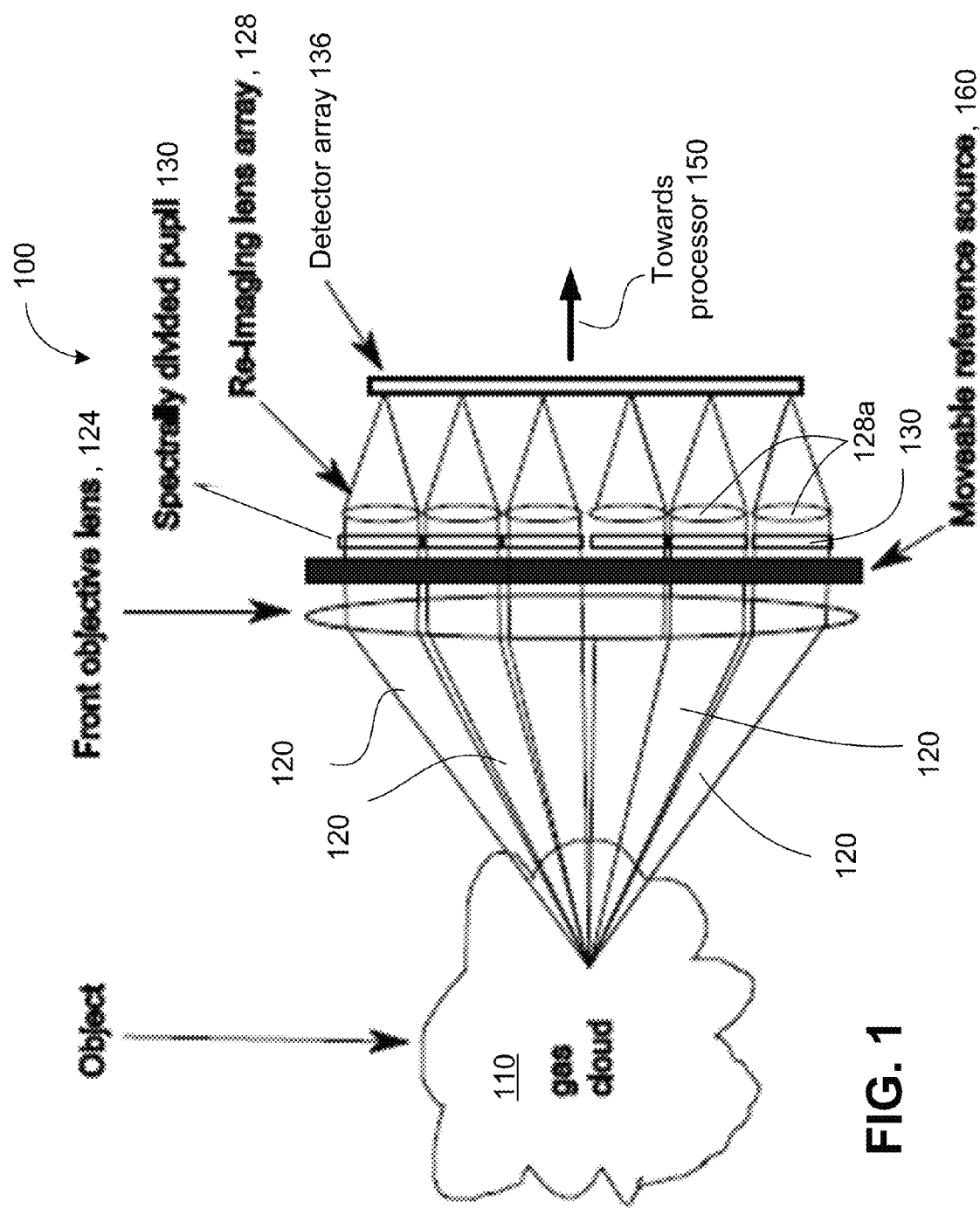
FIG. 1 shows an embodiment of an imaging system including a common front objective lens that has a pupil divided spectrally and re-imaged with a plurality of lenses onto an infrared FPA.

The following description is directed to certain implementations for the purposes of describing the innovative aspects of this disclosure. However, a person having ordinary skill in the art will readily recognize that the teachings herein can be applied in a multitude of different ways. The described implementations may be implemented in any device, apparatus, or system that can be configured to operate as an imaging system such as in an infra-red imaging system. The methods and systems described herein can be included in or associated with a variety of devices such as, but not limited to devices used for visible and infrared spectroscopy, multispectral and hyperspectral imaging devices used in oil and gas exploration, refining, and transportation, agriculture, remote sensing, defense and homeland security, surveillance, astronomy, environmental monitoring, etc. The methods and systems described herein have applications in a variety of fields including but not limited to agriculture, biology, physics, chemistry, defense and homeland security, environment, oil and gas industry, etc. The teachings are not intended to be limited to the implementations depicted solely in the Figures, but instead have wide applicability as will be readily apparent to one having ordinary skill in the art.

Various embodiments disclosed herein describe a divided-aperture infrared spectral imaging (DAISI) system that is structured and adapted to provide identification of target chemical contents of the imaged scene. The system is based on spectrally-resolved imaging and can provide such identification with a single-shot (also referred to as a snapshot) comprising a plurality of images having different wavelength compositions that are obtained generally simultaneously. Without any loss of generality, snapshot refers to a system in which most of the data elements that are collected are continuously viewing the light emitted from the scene. In contrast in scanning systems, at any given time only a minority of data elements are continuously viewing a scene, followed by a different set of data elements, and so on, until the full dataset is collected. Relatively fast operation can be achieved in a snapshot system because it does not need to use spectral or spatial scanning for the acquisition of infrared (IR) spectral signatures of the target chemical contents. Instead, IR detectors (such as, for example, infrared focal plane arrays or FPAs) associated with a plurality of different optical channels having different wavelength profiles can be used to form a spectral cube of imaging data. Although spectral data can be obtained from a single snapshot comprising multiple simultaneously acquired images corresponding to different wavelength ranges, in various embodiments, multiple snap shots may be obtained. In various embodiments, these multiple snapshots can be averaged. Similarly, in certain embodiments multiple snap shots may be obtained and a portion of these can be selected and possibly averaged. Also, in contrast to commonly used IR spectral imaging systems, the DAISI system does not require cooling. Accordingly, it can advantageously use uncooled infrared detectors. For example, in various implementations, the imaging systems disclosed herein do not include detectors configured to be cooled to a temperature below 300 Kelvin. As another example, in various implementations, the imaging systems disclosed herein do not include detectors configured to be cooled to a temperature below 273 Kelvin. As yet another example, in various implementations, the imaging systems disclosed herein do not include detectors configured to be cooled to a temperature below 250 Kelvin. As another example, in various implementations, the imaging systems disclosed herein do not include detectors configured to be cooled to a temperature below 200 Kelvin.

Implementations disclosed herein provide several advantages over existing IR spectral imaging systems, most if not all of which may require FPAs that are highly sensitive and cooled in order to compensate, during the optical detection, for the reduction of the photon flux caused by spectrum-scanning operation. The highly sensitive and cooled FPA systems are expensive and require a great deal of maintenance. Since various embodiments disclosed herein are configured to operate in single-shot acquisition mode without spatial and/or spectral scanning, the instrument can receive photons from a plurality of points (e.g., every point) of the object substantially simultaneously, during the single reading. Accordingly, the embodiments of imaging system described herein can collect a substantially greater amount of optical power from the imaged scene (for example, an order of magnitude more photons) at any given moment in time especially in comparison with spatial and/or spectral scanning systems. Consequently, various embodiments of the imaging systems disclosed herein can be operated using uncooled detectors (for example, FPA unit including an array of microbolometers) that are less sensitive to photons in the IR but are well fit for continuous monitoring applications. For example, in various implementations, the imaging systems disclosed herein do not include detectors configured to be cooled to a temperature below 300 Kelvin. As another example, in various implementations, the imaging systems disclosed herein do not include detectors configured to be cooled to a temperature below 273 Kelvin. As yet another example, in various implementations, the imaging systems disclosed herein do not include detectors configured to be cooled to a temperature below 250 Kelvin. As another example, in various implementations, the imaging systems disclosed herein do not include detectors configured to be cooled to a temperature below 200 Kelvin. Imaging systems including uncooled detectors can be capable of operating in extreme weather conditions, require less power, are capable of operation during day and night, and are less expensive.

Some embodiments described herein can also be less susceptible to motion artifacts in comparison with spatially and/or spectrally scanning systems which can cause errors in either the spectral data, spatial data, or both.

FIG. 1 provides a diagram schematically illustrating spatial and spectral division of incoming light by an embodiment 100 of a divided aperture infrared spectral imager (DAISI) system that can image an object 110 possessing IR spectral signature(s). The system 100 includes a front objective lens 124, an array of optical filters 130, an array of reimaging lenses 128 and a detector array 136. In various embodiments, the detector array 136 can include a single FPA or an array of FPAs. Each detector in the detector array 136 can be disposed at the focus of each of the lenses in the array of reimaging lenses 128. In various embodiments, the detector array 136 can include a plurality of photo-sensitive devices. In some embodiments, the plurality of photo-sensitive devices may comprise a two-dimensional imaging sensor array that is sensitive to radiation having wavelengths between 1 µm and 20 µm (for example, in near infra-red wavelength range, mid infra-red wavelength range, or long infra-red wavelength range). In various embodiments, the plurality of photo-sensitive devices can include CCD or CMOS sensors, bolometers, microbolometers or other detectors that are sensitive to infra-red radiation.

An aperture of the system 100 associated with the front objective lens system 124 is spatially and spectrally divided by the combination of the array of optical filters 130 and the array of reimaging lenses 128. In various embodiments, the combination of the array of optical filters 130 and the array of reimaging lenses 128 can be considered to form a spectrally divided pupil that is disposed forward of the optical detector array 136. The spatial and spectral division of the aperture into distinct aperture portions forms a plurality of optical channels 120 along which light propagates. In various embodiments, the array 128 of re-imaging lenses 128a and the array of spectral filters 130 which respectively correspond to the distinct optical channels 120. The plurality of optical channels 120 can be spatially and/or spectrally distinct. The plurality of optical channels 120 can be formed in the object space and/or image space. In one implementation, the distinct channels 120 may include optical channels that are separated angularly in space. The array of spectral filters 130 may additionally include a filter-holding aperture mask (comprising, for example, IR light-blocking materials such as ceramic, metal, or plastic). Light from the object 110 (for example a cloud of gas), the optical properties of which in the IR are described by a unique absorption, reflection and/or emission spectrum, is received by the aperture of the system 100. This light propagates through each of the plurality of optical channels 120 and is further imaged onto the optical detector array 136. In various implementations, the detector array 136 can include at least one FPA. In various embodiments, each of the re-imaging lenses 128a can be spatially aligned with a respectively-corresponding spectral region. In the illustrated implementation, each filter element from the array of spectral filters 130 corresponds to a different spectral region. Each re-imaging lens 128a and the corresponding filter element of the array of spectral filter 130 can coincide with (or form) a portion of the divided aperture and therefore with respectively-corresponding spatial channel 120. Accordingly, in various embodiment an imaging lens 128a and a corresponding spectral filter can be disposed in the optical path of one of the plurality of optical channels 120. Radiation from the object 110 propagating through each of the plurality of optical channels 120 travels along the optical path of each re-imaging lens 128a and the corresponding filter element of the array of spectral filter 130 and is incident on the detector array (e.g., FPA component) 136 to form a single image (e.g., sub-image) of the object 110. The image formed by the detector array 136 generally includes a plurality of sub-images formed by each of the optical channels 120. Each of the plurality of sub-images can provide different spatial and spectral information of the object 110. The different spatial information results from some parallax because of the different spatial locations of the smaller apertures of the divided aperture. In various embodiments, adjacent sub-images can be characterized by close or substantially equal spectral signatures. The detector array (e.g., FPA component) 136 is further operably connected with a processor 150 (not shown). The processor 150 can be programmed to aggregate the data acquired with the system 100 into a spectral data cube. The data cube represents, in spatial (x, y) and spectral (λ) coordinates, an overall spectral image of the object 110 within the spectral region defined by the combination of the filter elements in the array of spectral filters 130. Additionally, in various embodiments, the processor or processing electronics 150 may be programmed to determine the unique absorption characteristic of the object 110. Also, the processor/processing electronics 150 can, alternatively or in addition, map the overall image data cube into a cube of data representing, for example, spatial distribution of concentrations, c, of targeted chemical components within the field of view associated with the object 110.

Various implementations of the embodiment 100 can include an optional moveable temperature-controlled reference source 160 including, for example, a shutter system comprising one or more reference shutters maintained at different temperatures. The reference source 160 can include a heater, a cooler or a temperature-controlled element configured to maintain the reference source 160 at a desired temperature. For example, in various implementations, the embodiment 100 can include two reference shutters maintained at different temperatures. The reference source 160 is removably and, in one implementation, periodically inserted into an optical path of light traversing the system 100 from the object 110 to the detector array (e.g., FPA component) 136 along at least one of the channels 120. The removable reference source 160 thus can block such optical path. Moreover, this reference source 160 can provide a reference IR spectrum to recalibrate various components including the detector array 136 of the system 100 in real time. The configuration of the moveable reference source 160 is further discussed below.

In the embodiment 100, the front objective lens system 124 is shown to include a single front objective lens positioned to establish a common field-of-view (FOV) for the reimaging lenses 128a and to define an aperture stop for the whole system. In this specific case, the aperture stop substantially spatially coincides with and/or is about the same size or slightly larger, as the plurality of smaller limiting apertures corresponding to different optical channels 120. As a result, the positions for spectral filters of the different optical channels 120 coincide with the position of the aperture stop of the whole system, which in this example is shown as a surface between the lens system 124 and the array 128 of the reimaging lenses 128a. In various implementations, the lens system 124 can be an objective lens 124. However, the objective lens 124 is optional and various embodiments of the system 100 need not include the objective lens 124. In various embodiments, the objective lens 124 can slightly shifts the images obtained by the different detectors in the array 136 spatially along a direction perpendicular to optical axis of the lens 124, thus the functionality of the system 100 is not necessarily compromised when the objective lens 124 is not included. Generally, however, the field apertures corresponding to different optical channels may be located in the same or different planes. These field apertures may be defined by the aperture of the reimaging lens 128a and/or filters in the divided aperture 130 in certain implementations. In one implementation, the field apertures corresponding to different optical channels can be located in different planes and the different planes can be optical conjugates of one another. Similarly, while all of the filter elements in the array of spectral filters 130 of the embodiment 100 are shown to lie in one plane, generally different filter elements of the array of spectral filter 130 can be disposed in different planes. For example, different filter elements of the array of spectral filters 130 can be disposed in different planes that are optically conjugate to one another. However, in other embodiments, the different filter elements can be disposed in non-conjugate planes.

Figure 2:
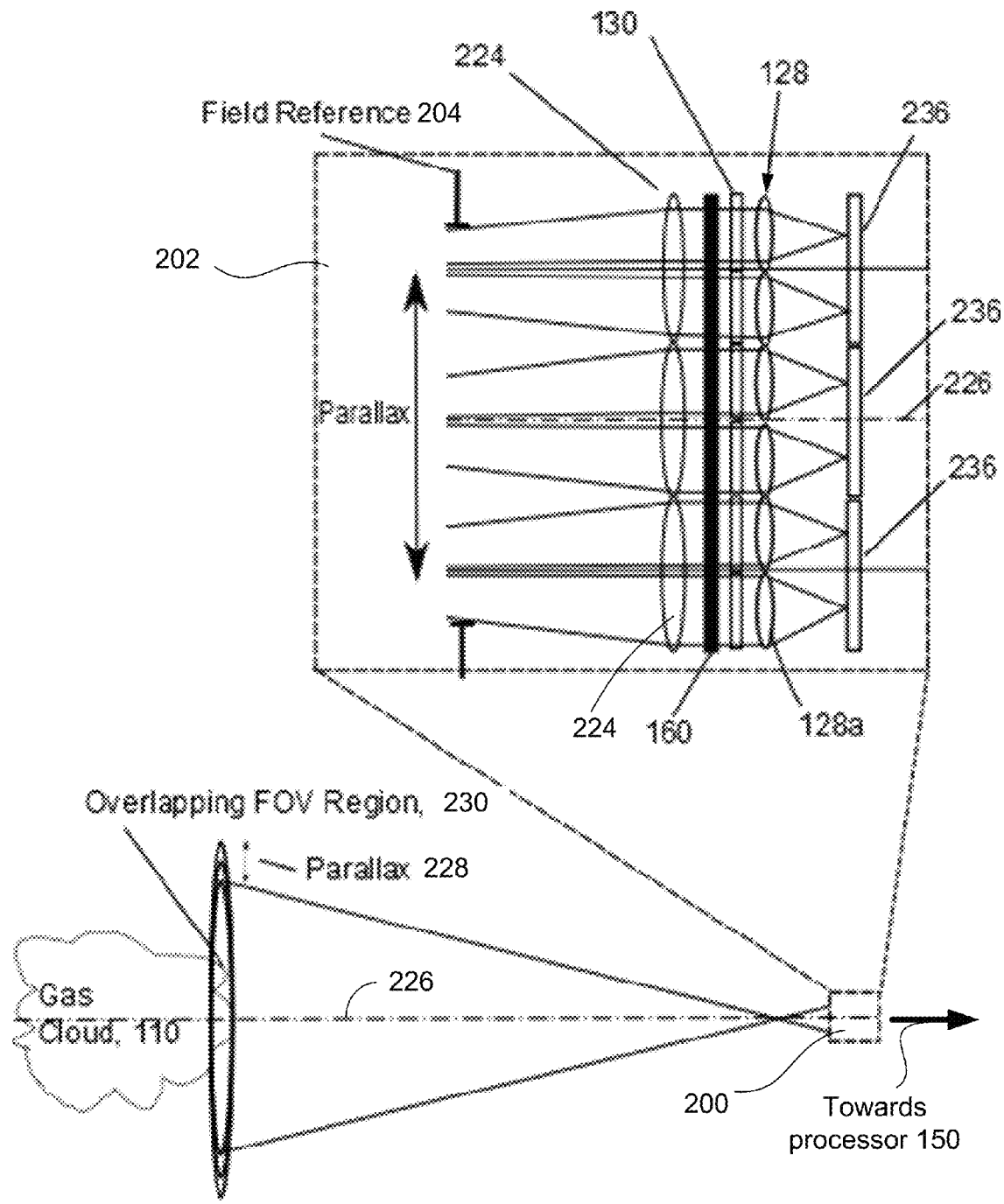
FIG. 2 shows an embodiment with a divided front objective lens and an array of infrared sensing FPAs.

In contrast to the embodiment 100, the front objective lens 124 need not be a single optical element, but instead can include a plurality of lenses 224 as shown in an embodiment 200 of the DAISI imaging system in FIG. 2. These lenses 224 are configured to divide an incoming optical wavefront from the object 110. For example, the array of front objective lenses 224 can be disposed so as to receive an IR wavefront emitted by the object that is directed toward the DAISI system. The plurality of front objective lenses 224 divide the wavefront spatially into non-overlapping sections. FIG. 2 shows three objective lenses 224 in a front optical portion of the optical system contributing to the spatial division of the aperture of the system in this example. The plurality of objective lenses 224, however, can be configured as a two-dimensional (2D) array of lenses. FIG. 2 presents a general view of the imaging system 200 and the resultant field of view of the imaging system 200. An exploded view 202 of the imaging system 200 is also depicted in greater detail in a figure inset of FIG. 2. As illustrated in the detailed view 202, the embodiment of the imaging system 200 includes a field reference 204 at the front end of the system. The field reference 204 can be used to truncate the field of view. The configuration illustrated in FIG. 2 has an operational advantage over embodiment 100 of FIG. 1 in that the overall size and/or weight and/or cost of manufacture of the embodiment 200 can be greatly reduced because the objective lens is smaller. Each pair of the lenses in the array 224 and the array 128 is associated with a field of view (FOV). Each pair of lenses in the array 224 and the array 128 receives light from the object from a different angle. Accordingly, the FOV of the different pairs of lenses in the array 224 and the array 128 do not completely overlap as a result of parallax. As the distance between the imaging system 200 (portion 202) and the object 110 increases, the overlapping region 230 between the FOVs of the individual lenses 224 increases while the amount of parallax 228 remains approximately the same, thereby reducing its effect on the system 200. When the ratio of the parallax-to-object-distance is substantially equal to the pixel-size-to-system-focal-length ratio then the parallax effect may be considered to be negligible and, for practical purposes, no longer distinguishable. While the lenses 224 are shown to be disposed substantially in the same plane, optionally different objective lenses in the array of front objective lenses 224 can be disposed in more than one plane. For example, some of the individual lenses 224 can be displaced with respect to some other individual lenses 224 along the axis 226 (not shown) and/or have different focal lengths as compared to some other lenses 224. As discussed below, the field reference 204 can be useful in calibrating the multiple detectors 236.

In one implementation, the front objective lens system such as the array of lenses 224 is configured as an array of lenses integrated or molded in association with a monolithic substrate. Such an arrangement can reduce the costs and complexity otherwise accompanying the optical adjustment of individual lenses within the system. An individual lens 224 can optionally include a lens with varying magnification. As one example, a pair of thin and large diameter Alvarez plates can be used in at least a portion of the front objective lens system. Without any loss of generality, the Alvarez plates can produce a change in focal length when translated orthogonally with respect to the optical beam.

In further reference to FIG. 1, the detector array 136 (e.g., FPA component) configured to receive the optical data representing spectral signature(s) of the imaged object 110 can be configured as a single imaging array (e.g., FPA) 136. This single array may be adapted to acquire more than one image (formed by more than one optical channel 120) simultaneously. Alternatively, the detector array 136 may include a FPA unit. In various implementations, the FPA unit can include a plurality of optical FPAs. At least one of these plurality of FPAs can be configured to acquire more than one spectrally distinct image of the imaged object. For example, as shown in the embodiment 200 of FIG. 2, in various embodiments, the number of FPAs included in the FPA unit may correspond to the number of the front objective lenses 224. In the embodiment 200 of FIG. 2, for example, three FPAs 236 are provided corresponding to the three objective lenses 224. In one implementation of the system, the FPA unit can include an array of microbolometers. The use of multiple microbolometers advantageously allows for an inexpensive way to increase the total number of detection elements (i.e. pixels) for recording of the three-dimensional data cube in a single acquisition event (i.e. one snapshot). In various embodiments, an array of microbolometers more efficiently utilizes the detector pixels of the array of FPAs (e.g., each FPA) as the number of unused pixels is reduced, minimized and/or eliminated between the images that may exist when using a single microbolometer.

Figure 3A:
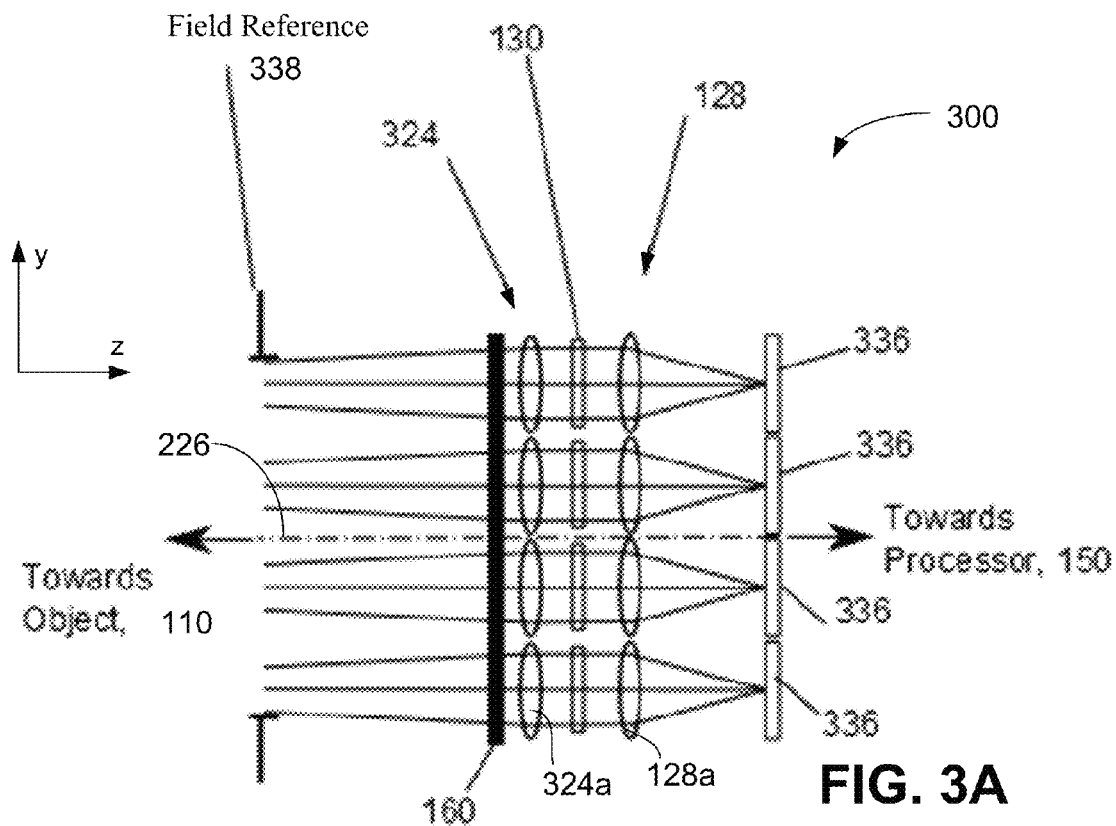
FIG. 3A represents an embodiment employing an array of front objective lenses operably matched with the re-imaging lens array.

FIG. 3A illustrates schematically an embodiment 300 of the imaging system in which the number of the front objective lenses 324a in the lens array 324, the number of re-imaging lenses 128a in the lens array 128, and the number of FPAs 336 are the same. So configured, each combination of respectively corresponding front objective lens 324, re-imaging lens 128a, and FPAs 336 constitutes an individual imaging channel. Such a channel is associated with acquisition of the IR light transmitted from the object 110 through an individual filter element of the array of optical filters 130. A field reference 338 of the system 300 is configured to have a uniform temperature across its surface and be characterized by a predetermined spectral curve of radiation emanating therefrom. In various implementations, the field reference 338 can be used as a calibration target to assist in calibrating or maintaining calibration of the FPA. Accordingly, in various implementations, the field reference 338 is used for dynamically adjusting the data output from each FPA 336 after acquisition of light from the object 110. This dynamic calibration process helps provide that output of the different (e.g., most, or each of the) FPA 336 represents correct acquired data, with respect to the other FPAs 336 for analysis, as discussed below in more detail.

Figure 3B:
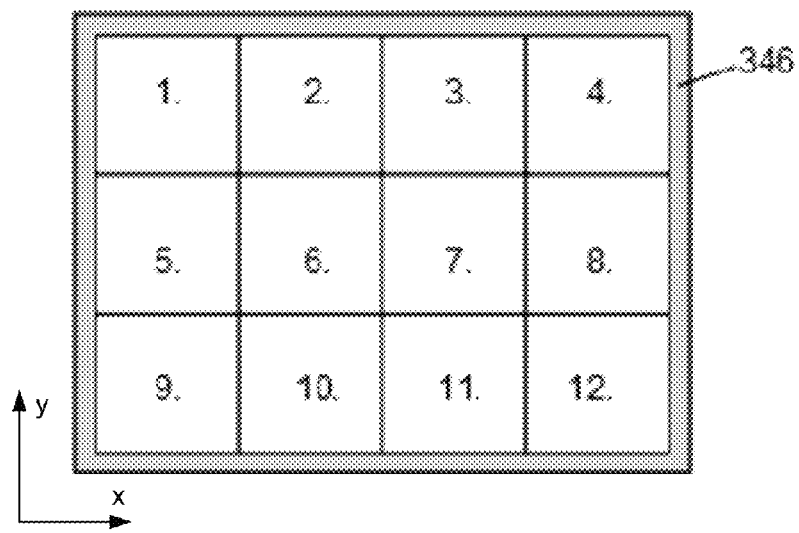
FIG. 3B illustrates a two-dimensional array of optical components corresponding to the embodiment of FIG. 3A.

FIG. 3B illustrates the plan view perpendicular to the axis 226 of an embodiment 300 of the imaging system illustrated in FIG. 3A. For the embodiment shown in FIG. 3B, the optical components (e.g., objective lenses 324a, filter elements of the array of spectral filters 130, re-imaging lenses 128a and FPA units 336) are arranged as a 4×3 array. In one implementation, the 4×3 array 340 of optical components (lenses 324a, 128a; detector elements 336) is used behind the temperature controlled reference target 160. The field reference aperture 338 can be adapted to obscure and/or block a peripheral portion of the bundle of light propagating from the object 110 towards the FPA units 336. As a result, the field reference 338 obscures and/or blocks the border or peripheral portion(s) of the images of the object 110 formed on the FPA elements located along the perimeter 346 of the detector system. Generally, two elements of the FPA unit will produce substantially equal values of digital counts when they are used to observe the same portion of the scene in the same spectral region using the same optical train. If any of these input parameters (for example, scene to be observed, spectral content of light from the scene, or optical elements delivering light from the scene to the two detector elements) differ, the counts associated with the elements of the FPA unit will differ as well. Accordingly, and as an example, in a case when the two FPAs of the FPA unit 336 (such as those denoted as #6 and #7 in FIG. 3B) remain substantially un-obscured by the field reference 338, the outputs from these FPAs can be dynamically adjusted to the output from one of the FPAs located along perimeter 346 (such as, for example, the FPA element #2 or FPA element #11) that processes light having similar spectral characteristics.

Figure 4:
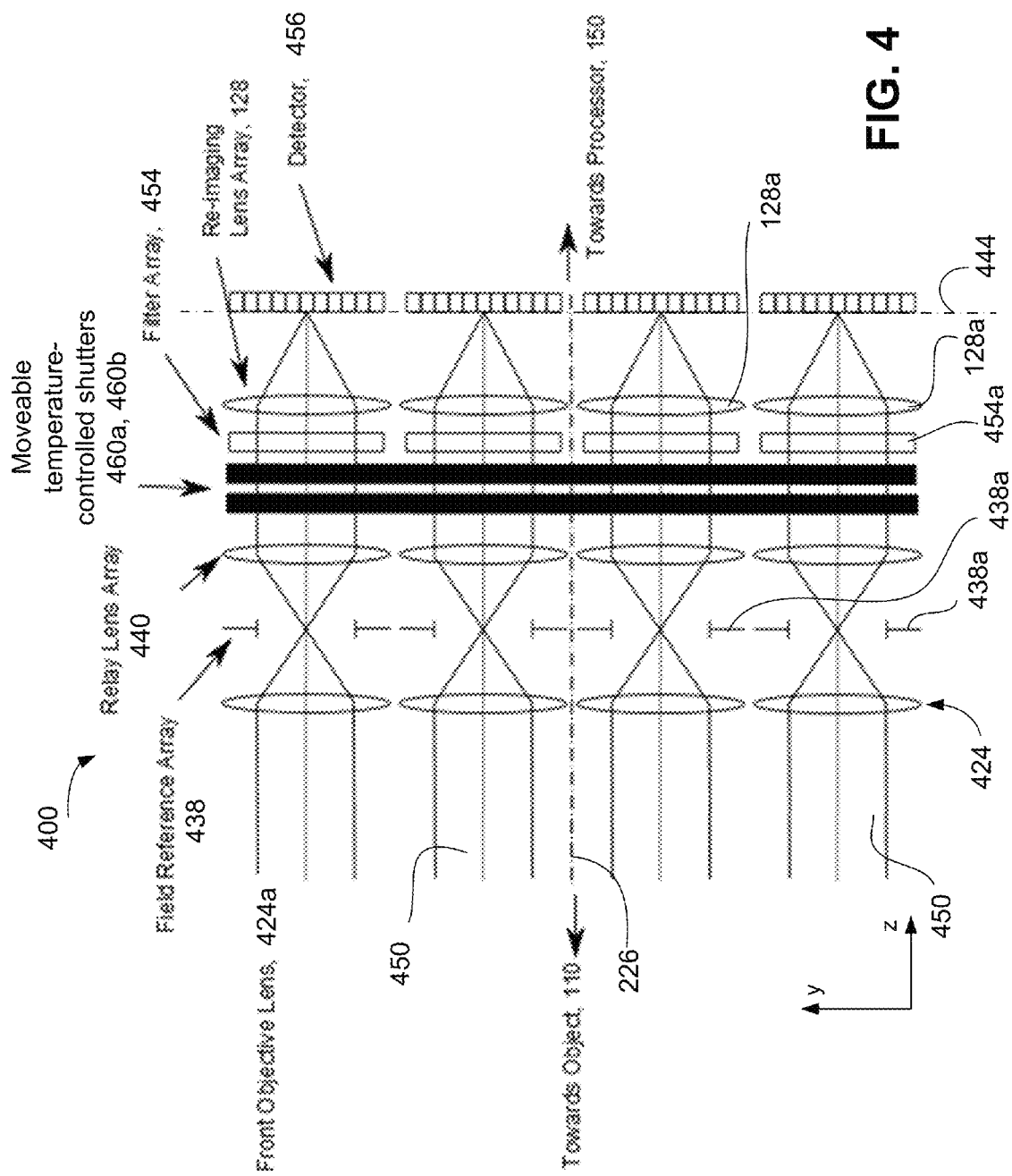
FIG. 4 is a diagram of the embodiment employing an array of field references (e.g., field stops that can be used as references for calibration) and an array of respectively corresponding relay lenses.

FIG. 4 illustrates schematically a portion of another embodiment of an imaging system 400 that contains an array 424 of front objective lenses 424a. The array 424 of lenses 424a adapted to receive light from the object 110 and relay the received light to the array 128 of re-imaging lenses 128a through an array 438 of field references (or field stops) 438a, and through an array 440 of the relay lenses. The spectral characteristics of the field references/field stops 438a can be known. The field references 438a are disposed at corresponding intermediate image planes defined, with respect to the object 110, by respectively corresponding front objective lenses 424a. When refractive characteristics of all of the front objective lenses 424a are substantially the same, all of the field references 438a are disposed in the same plane. A field reference 438a of the array 438 obscures (or casts a shadow on) a peripheral region of a corresponding image (e.g., sub-image) formed at the detector plane 444 through a respectively corresponding spatial imaging channel 450 of the system 400 prior to such image being spectrally processed by the processor 150. The array 440 of relay lenses then transmits light along each of the imaging channels 450 through different spectral filters 454a of the filter array 454, past the calibration apparatus that includes two temperature controlled shutters 460a, 460b, and then onto the detector module 456. In various embodiments, the detector module 456 can include a microbolometer array or some other IR FPA.

The embodiment 400 has several operational advantages. It is configured to provide a spectrally known object within every image (e.g., sub-image) and for every snapshot acquisition which can be calibrated against. Such spectral certainty can be advantageous when using an array of IR FPAs like microbolometers, the detection characteristics of which can change from one imaging frame to the next due to, in part, changes in the scene being imaged as well as the thermal effects caused by neighboring FPAs. In various embodiments, the field reference array 438 of the embodiment 400—can be disposed within the Rayleigh range (approximately corresponding to the depth of focus) associated with the front objective lenses 424, thereby removing unusable blurred pixels due to having the field reference outside of this range. Additionally, the embodiment 400 of FIG. 4 can be more compact than, for example, the configuration 300 of FIG. 3A. In the system shown in FIG. 3A, for example, the field reference 338 may be separated from the lens array 324 by a distance greater than several (for example, five) focal lengths to minimize/reduce blur contributed by the field reference to an image formed at a detector plane.

In various embodiments, the multi-optical FPA unit of the IR imaging system can additionally include an FPA configured to operate in a visible portion of the spectrum. In reference to FIG. 1, for example, an image of the scene of interest formed by such visible-light FPA may be used as a background to form a composite image by overlapping an IR image with the visible-light image. The IR image may be overlapped virtually, with the use of a processor and specifically-designed computer program product enabling such data processing, or actually, by a viewer. The IR image may be created based on the image data acquired by the individual FPAs 136. The so-formed composite image facilitates the identification of the precise spatial location of the target species, the spectral signatures of which the system is able to detect/recognize.

Optical Filters.

Figures 5A, 5B:
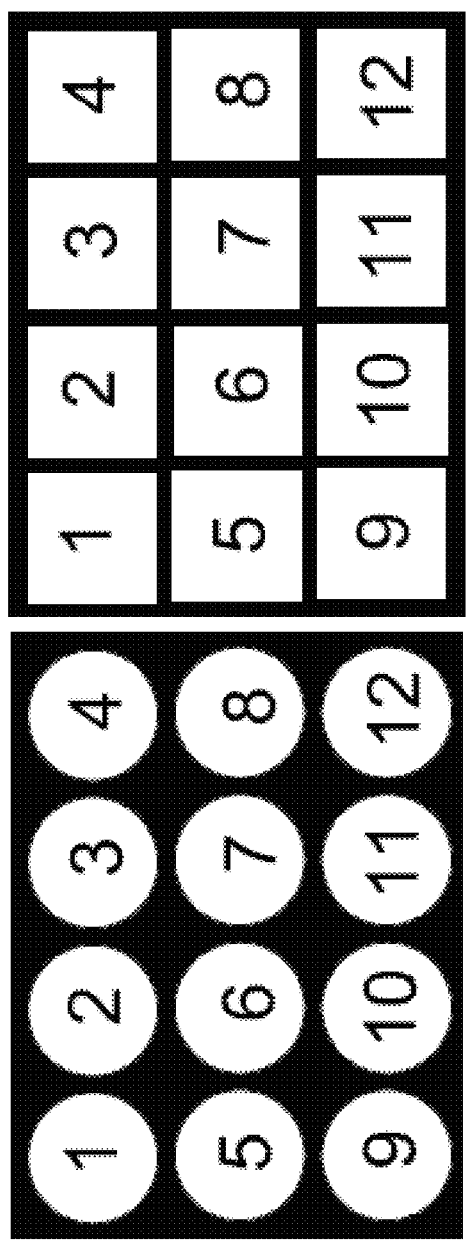
FIG. 5A is a diagram of a 4-by-3 pupil array comprising circular optical filters (and IR blocking material between the optical filters) used to spectrally divide an optical wavefront imaged with an embodiment of the system.
FIG. 5B is a diagram of a 4-by-3 pupil array comprising rectangular optical filters (and IR blocking material between the optical filters) used to spectrally divide an optical wavefront imaged with an embodiment of the system.

The optical filters, used with an embodiment of the system, that define spectrally-distinct IR image (e.g., sub-image) of the object can employ absorption filters, interference filters, and Fabry-Perot etalon based filters, to name just a few. When interference filters are used, the image acquisition through an individual imaging channel defined by an individual re-imaging lens (such as a lens 128a of FIGS. 1, 2, 3, and 4) may be carried out in a single spectral bandwidth or multiple spectral bandwidths. Referring again to the embodiments 100, 200, 300, 400 of FIGS. 1 through 4, and in further reference to FIG. 3B, examples of a 4-by-3 array of spectral filters 130 is shown in FIGS. 5A and 5B. Individual filters 1 through 12 are juxtaposed with a supporting opto-mechanical element (not shown) to define a filter-array plane that is oriented, in operation, substantially perpendicularly to the general optical axis 226 of the imaging system. In various implementations, the individual filters 1 through 12 need not be discrete optical components. Instead, the individual filters 1 through 12 can comprise one or more coatings that are applied to one or more surfaces of the reimaging lenses (such as a lens 128a of FIGS. 1, 2, 3, and 4) or the surfaces of one or more detectors.

Figure 6A:
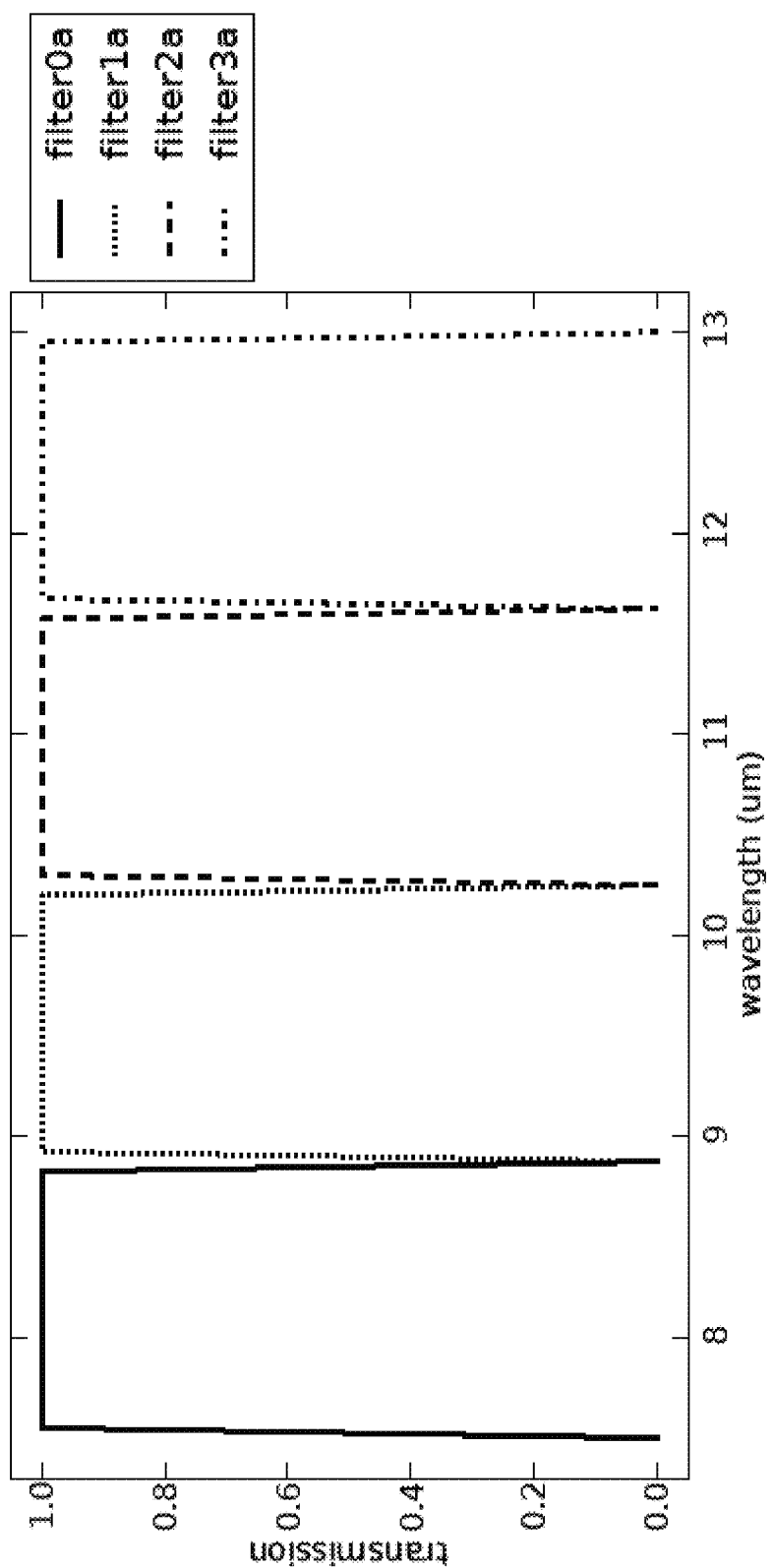
FIG. 6A depicts theoretical plots of transmission characteristics of a combination of band-pass filters used with an embodiment of the system.
Figure 6B:
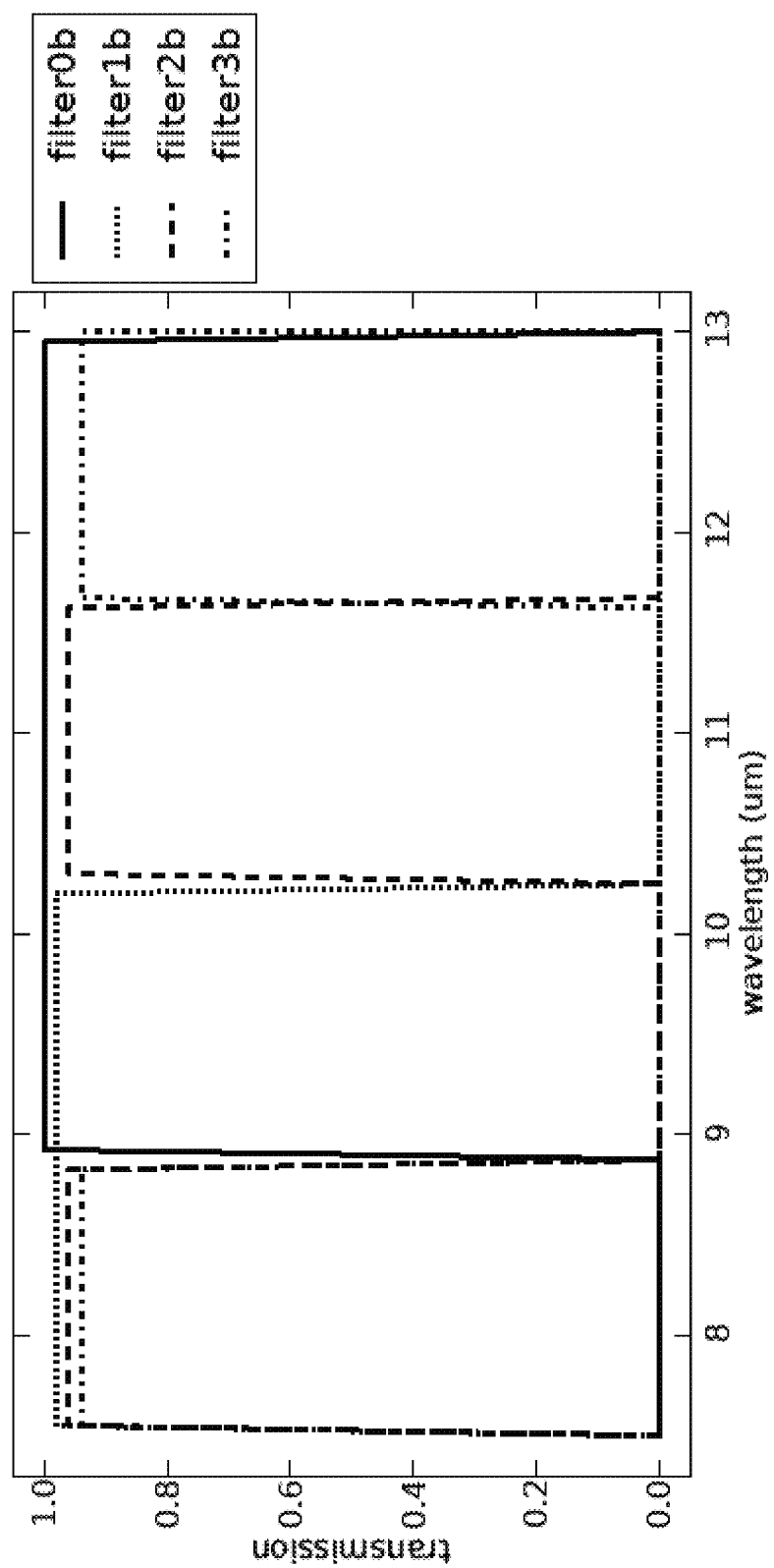
FIG. 6B depicts theoretical plots of transmission characteristics of a spectrally multiplexed notch-pass filter combination used in an embodiment of the system.

The optical filtering configuration of various embodiments disclosed herein may advantageously use a bandpass filter defining a specified spectral band. Any of the filters 0a through 3a the transmission curves of which are shown in FIG. 6A may, for example, be used. The filters may be placed in front of the optical FPA (or generally, between the optical FPA and the object). In particular, and in further reference to FIGS. 1, 2, 3, and 4, when optical detector arrays 136, 236, 336, 456 include microbolometers, the predominant contribution to noise associated with image acquisition is due to detector noise. To compensate and/or reduce the noise, various embodiments disclosed herein utilize spectrally-multiplexed filters. In various implementations, the spectrall-multiplexed filters can comprise a plurality of long pass filters, a plurality long pass filters, a plurality of band pass filters and any combinations thereof. An example of the spectral transmission characteristics of spectrally-multiplexed filters 0b through 3d for use with various embodiments of imaging systems disclosed herein is depicted in FIG. 6B. Filters of FIG. 6C can be referred to as long-wavelength pass, LP filters. An LP filter generally attenuates shorter wavelengths and transmits (passes) longer wavelengths (e.g., over the active range of the target IR portion of the spectrum). In various embodiments, short-wavelength-pass filters, SP, may also be used. An SP filter generally attenuates longer wavelengths and transmits (passes) shorter wavelengths (e.g., over the active range of the target IR portion of the spectrum). At least in part due to the snap-shot/non-scanning mode of operation, embodiments of the imaging system described herein can use less sensitive microbolometers without compromising the SNR. The use of microbolometers, as detector-noise-limited devices, in turn not only benefits from the use of spectrally multiplexed filters, but also does not require cooling of the imaging system during normal operation.

Referring again to FIGS. 6A, 6B, 6C, and 6D, each of the filters (0b . . . 3d) transmits light in a substantially wider region of the electromagnetic spectrum as compared to those of the filters (0a . . . 3a). Accordingly, when the spectrally-multiplexed set of filters (0b . . . 0d) is used with an embodiment of the imaging system, the overall amount of light received by the FPAs (for example, 236, 336) is larger than would be received when using the bandpass filters (0a . . . 4a). This "added" transmission of light defined by the use of the spectrally-multiplexed LP (or SP) filters facilitates an increase of the signal on the FPAs above the level of the detector noise. Additionally, by using, in an embodiment of the imaging system, filters having spectral bandwidths greater than those of band-pass filters, the uncooled FPAs of the embodiment of the imaging system experience less heating from radiation incident thereon from the imaged scene and from radiation emanating from the FPA in question itself. This reduced heating is due to a reduction in the back-reflected thermal emission(s) coming from the FPA and reflecting off of the filter from the non-band-pass regions. As the transmission region of the multiplexed LP (or SP) filters is wider, such parasitic effects are reduced thereby improving the overall performance of the FPA unit.

In one implementation, the LP and SP filters can be combined, in a spectrally-multiplexed fashion, in order to increase or maximize the spectral extent of the transmission region of the filter system of the embodiment.

The advantage of using spectrally multiplexed filters is appreciated based on the following derivation, in which a system of M filters is examined (although it is understood that in practice an embodiment of the invention can employ any number of filters). As an illustrative example, the case of M=7 is considered. Analysis presented below relates to one spatial location in each of the images (e.g., sub-images) formed by the differing imaging channels (e.g., different optical channels 120) in the system. A similar analysis can be performed for each point at an image (e.g., sub-image), and thus the analysis can be appropriately extended as required.

The unknown amount of light within each of the M spectral channels (corresponding to these M filters) is denoted with $f_1, f_2, f_3, \ldots f_M$, and readings from corresponding detector elements receiving light transmitted by each filter is denoted as $g_1, g_2, g_3 \ldots g_M$, while measurement errors are represented by $n_1, n_2, n_3, \ldots n_M$. Then, the readings at the seven FPA pixels each of which is optically filtered by a corresponding band-pass filter of FIG. 6A can be represented by:

$g_1 = f_1 + n^1,$ $g_2 = f_2 + n_2,$ $g_3 = f_3 + n_3,$ $g_4 = f_4 + n_4,$ $g_5 = f_5 + n_5,$ $g_6 = f_6 + n_6,$ $g_7 = f_7 + n_7,$

These readings (pixel measurements) $g_i$ are estimates of the spectral intensities $f_i$. The estimates $g_i$ are not equal to the corresponding $f_i$ values because of the measurement errors $n_i$. However, if the measurement noise distribution has zero mean, then the ensemble mean of each individual measurement can be considered to be equal to the true value, i.e. $\langle g_i \rangle = f_i$. Here, the angle brackets indicate the operation of calculating the ensemble mean of a stochastic variable. The variance of the measurement can, therefore, be represented as:

$$\langle (g_i - f_i)^2 \rangle = \langle n_i^2 \rangle = \sigma^2$$

In embodiments utilizing spectrally-multiplexed filters, in comparison with the embodiments utilizing band-pass filters, the amount of radiant energy transmitted by each of the spectrally-multiplexed LP or SP filters towards a given detector element can exceed that transmitted through a spectral band of a band-pass filter. In this case, the intensities of light corresponding to the independent spectral bands can be reconstructed by computational means. Such embodiments can be referred to as a "multiplex design".

One matrix of such "multiplexed filter" measurements includes a Hadamard matrix requiring "negative" filters that may not be necessarily appropriate for the optical embodiments disclosed herein. An S-matrix approach (which is restricted to having a number of filters equal to an integer that is multiple of four minus one) or a row-doubled Hadamard matrix (requiring a number of filters to be equal to an integer multiple of eight) can be used in various embodiments. Here, possible numbers of filters using an S-matrix setup are 3, 7, 11, etc and, if a row-doubled Hadamard matrix setup is used, then the possible number of filters is 8, 16, 24, etc. For example, the goal of the measurement may be to measure seven spectral band $f_i$ intensities using seven measurements $g_i$ as follows:

$g_1 = f_1 + 0 + f_3 + 0 + f_5 + 0 + f_7 + n_1$ $g_2 = 0 + f_2 + f_3 + 0 + 0 + f_6 + f_7 + n_2$ $g_3 = f_1 + f_2 + 0 + 0 + f_5 + 0 + f_7 + n_3$ $g_4 = 0 + 0 + 0 + f_4 + f_5 + f_7 + f_8 + n_4$ $g_5 = f_1 + 0 + f_3 + f_4 + 0 + f_6 + 0 + n_5$ $g_6 = 0 + f_2 + f_3 + f_4 + f_5 + 0 + 0 + n_6$ $g_7 = f_1 + f_2 + 0 + f_4 + 0 + 0 + f_7 + n_7$

Optical transmission characteristics of the filters described above are depicted in FIG. 6B. Here, a direct estimate of the $f_i$ is no longer provided through a relationship similar to $\langle g_i \rangle = f_i$. Instead, if a "hat" notation is used to denote an estimate of a given value, then a linear combination of the measurements can be used such as, for example, $\hat{f}_1 = \frac{1}{4}(+g_1 - g_2 + g_3 - g_4 + g_5 - g_6 + g_7),$ $\hat{f}_2 = \frac{1}{4}(-g_1 + g_2 + g_3 - g_4 - g_5 + g_6 + g_7),$ $\hat{f}_3 = \frac{1}{4}(+g_1 + g_2 - g_3 - g_4 + g_5 + g_6 - g_7),$ $\hat{f}_4 = \frac{1}{4}(-g_1 - g_2 - g_3 + g_4 + g_5 + g_6 + g_7),$ $\hat{f}_5 = \frac{1}{4}(+g_1 - g_2 + g_3 + g_4 - g_5 + g_6 - g_7),$ $\hat{f}_6 = \frac{1}{4}(-g_1 + g_2 + g_3 + g_4 + g_5 - g_6 - g_7),$ $\hat{f}_7 = \frac{1}{4}(+g_1 + g_2 - g_3 + g_4 - g_5 - g_6 + g_7),$ These $\hat{f}_i$ are unbiased estimates when the $n_i$ are zero mean stochastic variables, so that $\langle \hat{f}_i - f_i \rangle = 0$. The measurement variance corresponding to $i^{th}$ measurement is given by the equation below:

$$\langle (\hat{f}_i - f_i)^2 \rangle = \frac{7}{16} \sigma^2$$

From the above equation, it is observed that by employing spectrally-multiplexed system the signal-to-noise ratio (SNR) of a measurement is improved by a factor of $\sqrt{16/7} = 1.51$.

For N channels, the SNR improvement achieved with a spectrally-multiplexed system can be expressed as $(N+1)/(2\sqrt{N})$. For example, an embodiment employing 12 spectral channels (N=12) is characterized by a SNR improvement, over a non-spectrally-multiplexed system, comprising a factor of up to 1.88.

Figure 6C:
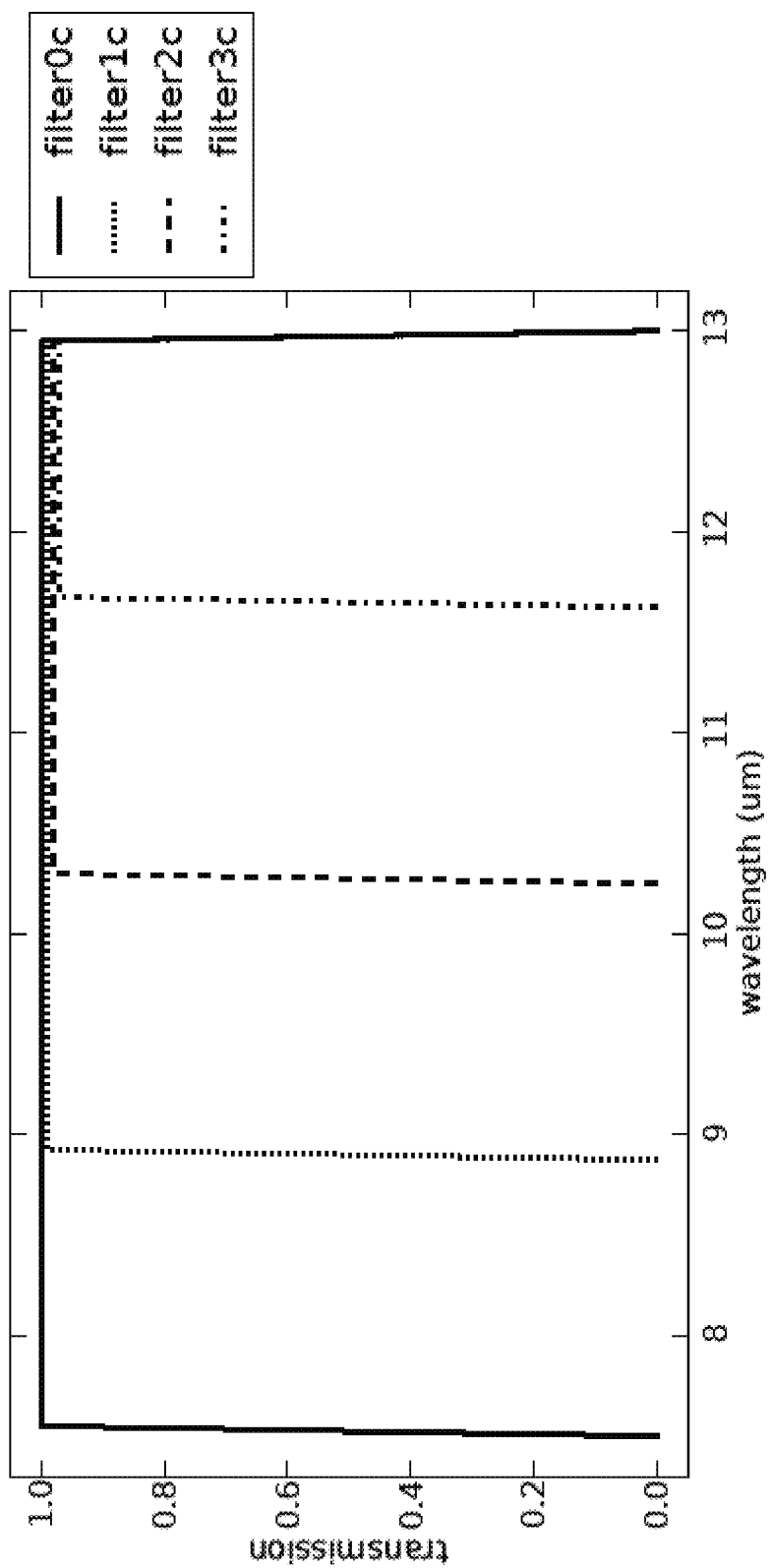
FIG. 6C shows theoretical plots of transmission characteristics of spectrally multiplexed long-pass filter combination used in an embodiment of the system.
Figure 6D:
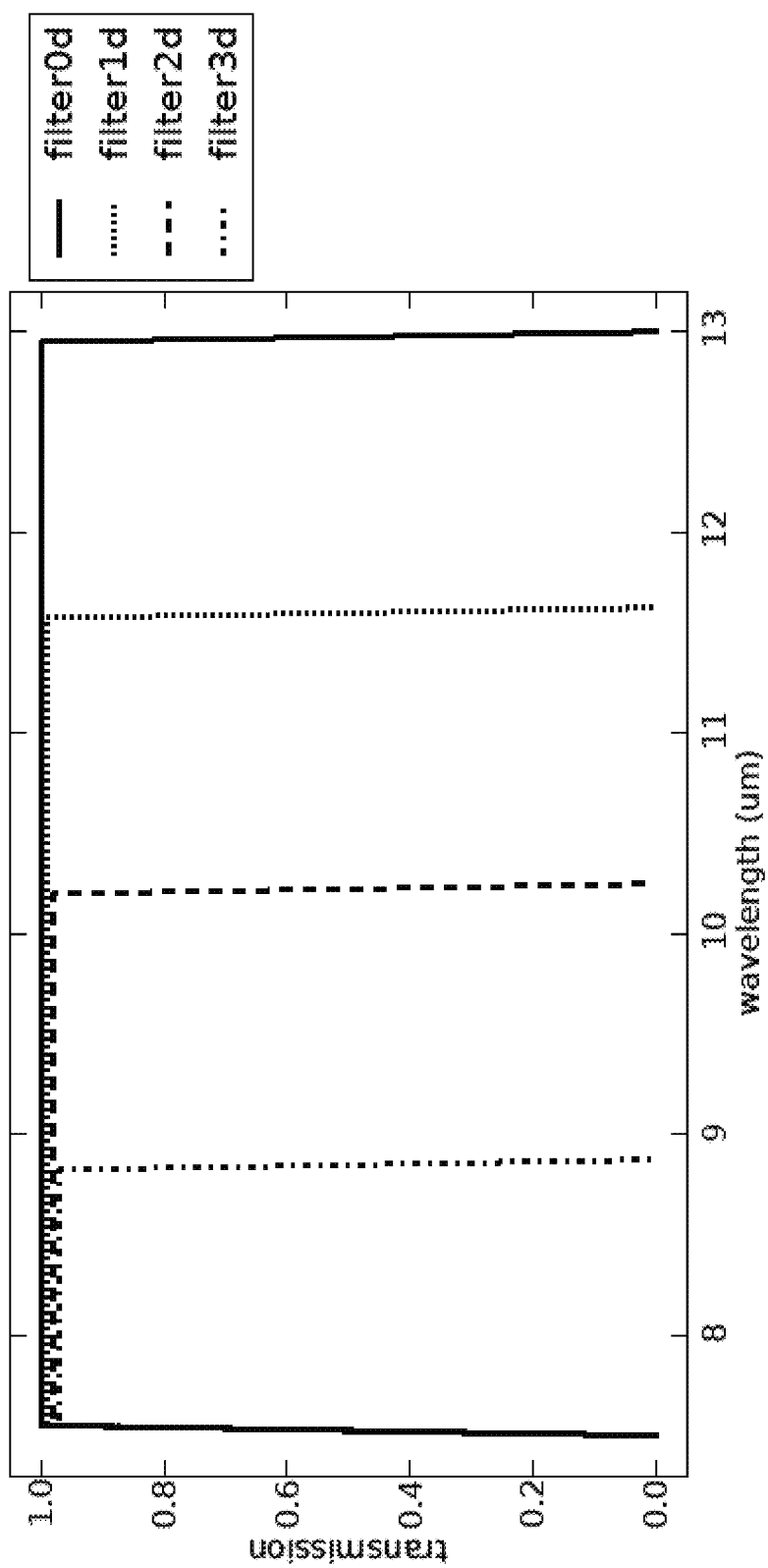
FIG. 6D shows theoretical plots of transmission characteristics of spectrally multiplexed short-pass filter combination used in an embodiment of the system.

Two additional examples of related spectrally-multiplexed filter arrangements 0c through 3c and 0d through 3d that can be used in various embodiments of the imaging systems described herein are shown in FIGS. 6C and 6D, respectively. The spectrally-multiplexed filters shown in FIGS. 6C and 6D can be used in embodiments of imaging systems employing uncooled FPAs (such as microbolometers). FIG. 6C illustrates a set of spectrally-multiplexed long-wavelength pass (LP) filters used in the system. An LP filter generally attenuates shorter wavelengths and transmits (passes) longer wavelengths (e.g., over the active range of the target IR portion of the spectrum). A single spectral channel having a transmission characteristic corresponding to the difference between the spectral transmission curves of at least two of these LP filters can be used to procure imaging data for the data cube using an embodiment of the system described herein. In various implementations, the spectral filters disposed with respect to the different FPAs can have different spectral characteristics. In various implementations, the spectral filters may be disposed in front of only some of the FPAs while the remaining FPAs may be configured to receive unfiltered light. For example, in some implementations, only 9 of the 12 detectors in the 4×3 array of detectors described above may be associated with a spectral filter while the other 3 detectors may be configured to received unfiltered light. Such a system may be configured to acquire spectral data in 10 different spectral channels in a single data acquisition event.

The use of microbolometers, as detector-noise-limited devices, in turn not only can benefit from the use of spectrally multiplexed filters, but also does not require cooling of the imaging system during normal operation. In contrast to imaging systems that include highly sensitive FPA units with reduced noise characteristics, the embodiments of imaging systems described herein can employ less sensitive microbolometers without compromising the SNR. This result is at least in part due to the snap-shot/non-scanning mode of operation.

As discussed above, an embodiment may optionally, and in addition to a temperature-controlled reference unit (for example temperature controlled shutters such as shutters 160; 160a, 160b, 460a, 460b), employ a field reference component (e.g., field reference aperture 338 in FIG. 3A), or an array of field reference components (e.g., filed reference apertures 438 in FIG. 4), to enable dynamic calibration. Such dynamic calibration can be used for spectral acquisition of one or more or every data cube. Such dynamic calibration can also be used for a spectrally-neutral camera-to-camera combination to enable dynamic compensation of parallax artifacts. The use of the temperature-controlled reference unit (for example, temperature-controlled shutter system 160) and field-reference component(s) facilitates maintenance of proper calibration of each of the FPAs individually and the entire FPA unit as a whole.

In particular, and in further reference to FIGS. 1, 2, 3, and 4, the temperature-controlled unit generally employs a system having first and second temperature zones maintained at first and second different temperatures. For example, shutter system of each of the embodiments 100, 200, 300 and 400 can employ not one but at least two temperature-controlled shutters that are substantially parallel to one another and transverse to the general optical axis 226 of the embodiment(s) 100, 200, 300, 400. Two shutters at two different temperatures may be employed to provide more information for calibration; for example, the absolute value of the difference between FPAs at one temperature as well as the change in that difference with temperature change can be recorded. Referring, for example, to FIG. 4, in which such multi-shutter structure is shown, the use of multiple shutters enables the user to create a known reference temperature difference perceived by the FPAs 456. This reference temperature difference is provided by the IR radiation emitted by the shutter(s) 160a, 160b when these shutters are positioned to block the radiation from the object 110. As a result, not only the offset values corresponding to each of the individual FPAs pixels can be adjusted but also the gain values of these FPAs. In an alternative embodiment, the system having first and second temperature zones may include a single or multi-portion piece. This single or multi-portion piece may comprise for example a plate. This piece may be mechanically-movable across the optical axis with the use of appropriate guides and having a first portion at a first temperature and a second portion at a second temperature.

Indeed, the process of calibration of an embodiment of the imaging system starts with estimating gain and offset by performing measurements of radiation emanating, independently, from at least two temperature-controlled shutters of known and different radiances. The gain and offset can vary from detector pixel to detector pixel. Specifically, first the response of the detector unit 456 to radiation emanating from one shutter is carried out. For example, the first shutter 160a blocks the FOV of the detectors 456 and the temperature $T_1$ is measured directly and independently with thermistors. Following such initial measurement, the first shutter 160a is removed from the optical path of light traversing the embodiment and another second shutter (for example, 160b) is inserted in its place across the optical axis 226 to prevent the propagation of light through the system. The temperature of the second shutter 160b can be different than the first shutter ($T_2 \neq T_1$). The temperature of the second shutter 160b is also independently measured with thermistors placed in contact with this shutter, and the detector response to radiation emanating from the shutter 160b is also recorded. Denoting operational response of FPA pixels (expressed in digital numbers, or "counts") as $g_i$ to a source of radiance $L_i$, the readings corresponding to the measurements of the two shutters can be expressed as:

$$g_1 = \gamma L_1(T_1) + g_{offset}$$

$$g_2 = \gamma L_2(T_2) + g_{offset}$$

Here, $g_{offset}$ is the pixel offset value (in units of counts), and $\gamma$ is the pixel gain value (in units of counts per radiance unit). The solutions of these two equations with respect to the two unknowns $g_{offset}$ and $\gamma$ can be obtained if the values of $g_1$ and $g_2$ and the radiance values $L_1$ and $L_2$ are available. These values can, for example, be either measured by a reference instrument or calculated from the known temperatures $T_1$ and $T_2$ together with the known spectral response of the optical system and FPA. For any subsequent measurement, one can then invert the equation(s) above in order to estimate the radiance value of the object from the detector measurement, and this can be done for each pixel in each FPA within the system.

As already discussed, and in reference to FIGS. 1 through 4, the field-reference apertures may be disposed in an object space or image space of the optical system, and dimensioned to block a particular portion of the IR radiation received from the object. In various implementations, the field-reference aperture, the opening of which can be substantially similar in shape to the boundary of the filter array (for example, and in reference to a filter array of FIGS. 3B, 5B—e.g., rectangular). The field-reference aperture can be placed in front of the objective lens (124, 224, 324, 424) at a distance that is at least several times (in one implementation—at least five times) larger than the focal length of the lens such that the field-reference aperture is placed closer to the object. Placing the field-reference aperture closer to the object can reduce the blurriness of the image. In the embodiment 400 of FIG. 4, the field-reference aperture can be placed within the depth of focus of an image conjugate plane formed by the front objective lens 424. The field reference, generally, can facilitate, effectuates and/or enable dynamic compensation in the system by providing a spectrally known and temporally-stable object within every scene to reference and stabilize the output from the different FPAs in the array.

Because each FPA's offset value is generally adjusted from each frame to the next frame by the hardware, comparing the outputs of one FPA with another can have an error that is not compensated for by the static calibration parameters $g_{offset}$ and $\gamma$ established, for example, by the movable shutters 160. In order to ensure that FPAs operate in radiometric agreement over time, it is advantageous for a portion of each detector array to view a reference source (such as the field reference 338 in FIG. 3A, for example) over a plurality of frames obtained over time. If the reference source spectrum is known a priori (such as a blackbody source at a known temperature), one can measure the response of each FPA to the reference source in order to estimate changes to the pixel offset value. However, the temperature of the reference source need not be known. In such implementations, dynamic calibration of the different detectors can be performed by monitoring the change in the gain and the offset for the various detectors from the time the movable shutters used for static calibration are removed. An example calculation of the dynamic offset proceeds as follows.

Among the FPA elements in an array of FPAs in an embodiment of the imaging system, one FPA can be selected to be the "reference FPA". The field reference temperature measured by all the other FPAs can be adjusted to agree with the field reference temperature measured by the reference as discussed below. The image obtained by each FPA includes a set of pixels obscured by the field reference 338. Using the previously obtained calibration parameters $g_{offset}$ and $\gamma$ (the pixel offset and gain), the effective blackbody temperature $T_i$ of the field reference as measured by each FPA is estimated using the equation below:

$$T_i = \text{mean}\{(g+\Delta g_i+g_{offset})/\gamma\} = \text{mean}\{(g-g_{offset})/\gamma\} + \Delta T_i$$

Using the equation above, the mean value over all pixels that are obscured by the field reference is obtained. In the above equation $\Delta g_i$ is the difference in offset value of the current frame from $\Delta g_{offset}$ obtained during the calibration step. For the reference FPA, $\Delta g_i$ can be simply set to zero. Then, using the temperature differences measured by each FPA, one obtains $$T_i - T_{ref} = \text{mean}\{(g+\Delta g_i+g_{offset})/\gamma\} + \Delta T_i - \text{mean}\{(g-g_{offset})/\gamma\} = \Delta T_i$$

Once $\Delta T_i$ for each FPA is measured, its value can be subtracted from each image in order to force operational agreement between such FPA and the reference FPA. While the calibration procedure has been discussed above in reference to calibration of temperature, a procedurally similar methodology of calibration with respect to radiance value can also be implemented.

Examples of Methodology of Measurements.

Prior to optical data acquisition using an embodiment of the IR imaging system as described herein, one or more, most, or potentially all the FPAs of the system can be calibrated. For example, greater than 50%, 60%, 70%, 80% or 90% or the FPAs 336 can be initially calibrated. As shown in FIG. 3, these FPAs 336 may form separate images of the object using light delivered in a corresponding optical channel that may include the combination of the corresponding front objective and re-imaging lenses 324, 128. The calibration procedure can allow formation of individual images in equivalent units (so that, for example, the reading from the FPA pixels can be re-calculated in units of temperature or radiance units, etc.). Moreover, the calibration process can also allow the FPAs (e.g., each of the FPAs) to be spatially co-registered with one another so that a given pixel of a particular FPA can be optically re-mapped through the optical system to the same location at the object as the corresponding pixel of another FPA.

To achieve at least some of these goals, a spectral differencing method may be employed. The method involves forming a difference image from various combinations of the images from different channels. In particular, the images used to form difference images can be registered by two or more different FPAs in spectrally distinct channels having different spectral filters with different spectral characteristics. Images from different channels having different spectral characteristics will provide different spectral information. Comparing (e.g., subtracting) these images, can therefore yield valuable spectral based information. For example, if the filter element of the array of spectral filters 130 corresponding to a particular FPA 336 transmits light from the object 110 including a cloud of gas, for example, with a certain spectrum that contains the gas absorption peak or a gas emission peak while another filter element of the array of spectral filters 130 corresponding to another FPA 336 does not transmit such spectrum, then the difference between the images formed by the two FPAs at issue will highlight the presence of gas in the difference image.

A shortcoming of the spectral differencing method is that contributions of some auxiliary features associated with imaging (not just the target species such as gas itself) can also be highlighted in and contribute to the difference image. Such contributing effects include, to name just a few, parallax-induced imaging of edges of the object, influence of magnification differences between the two or more optical channels, and differences in rotational positioning and orientation between the FPAs. While magnification-related errors and FPA-rotation-caused errors can be compensated for by increasing the accuracy of the instrument construction as well as by post-processing of the acquired imaging, parallax is scene-induced and is not so easily correctable. In addition, the spectral differencing method is vulnerable to radiance calibration errors. Specifically, if one FPA registers radiance of light from a given feature of the object as that having a temperature of 40° C., for example, while the data from another FPA represents the temperature of the same object feature as being 39° C., then such feature of the object will be enhanced or highlighted in the difference image (formed at least in part based on the images provided by these two FPAs) due to such radiance-calibration error.

One solution to some of such problems is to compare (e.g., subtract) images from the same FPA obtained at different instances in time. For example, images can be compared to or subtracted from a reference image obtained at another time. Such reference image, which is subtracted from other later obtained images, may be referred to as a temporal reference image. This solution can be applied to spectral difference images as well. For example, the image data resulting from spectral difference images can be normalized by the data corresponding to a temporal reference image. For instance, the temporal reference images can be subtracted from the spectral difference image to obtain the temporal difference image. This process is referred to, for the purposes of this disclosure, as a temporal differencing algorithm or method and the resultant image from subtracting the temporal reference image from another image (such as the spectral difference image) is referred to as the temporal difference image. In some embodiments where spectral differencing is employed, a temporal reference image may be formed, for example, by creating a spectral difference image from the two or more images registered by the two or more FPAs at a single instance in time. This spectral difference image is then used as a temporal reference image. The temporal reference image can then be subtracted from other later obtained images to provide normalization that can be useful in subtracting out or removing various errors or deleterious effects. For example, the result of the algorithm is not affected by a prior knowledge of whether the object or scene contains a target species (such as gas of interest), because the algorithm can highlight changes in the scene characteristics. Thus, a spectral difference image can be calculated from multiple spectral channels as discussed above based on a snap-shot image acquisition at any later time and can be subtracted from the temporal reference image to form a temporal difference image. This temporal difference image is thus a normalized difference image. The difference between the two images (the temporal difference image) can highlight the target species (gas) within the normalized difference image, since this species was not present in the temporal reference frame. In various embodiments, more than two FPAs can be used both for registering the temporal reference image and a later-acquired difference image to obtain a better SNR figure of merit. For example, if two FPAs are associated with spectral filters having the same spectral characteristic, then the images obtained by the two FPAs can be combined after they have been registered to get a better SNR figure.

While the temporal differencing method can be used to reduce or eliminate some of the shortcomings of the spectral differencing, it can introduce unwanted problems of its own. For example, temporal differencing of imaging data is less sensitive to calibration and parallax induced errors than the spectral differencing of imaging data. However, any change in the imaged scene that is not related to the target species of interest (such as particular gas, for example) is highlighted in a temporally-differenced image. Thus such change in the imaged scene may be erroneously perceived as a location of the target species triggering, therefore, an error in detection of target species. For example, if the temperature of the background against which the gas is being detected changes (due to natural cooling down as the day progresses, or increases due to a person or animal or another object passing through the FOV of the IR imaging system), then such temperature change produces a signal difference as compared to the measurement taken earlier in time. Accordingly, the cause of the scenic temperature change (the cooling object, the person walking, etc.) may appear as the detected target species (such as gas). It follows, therefore, that an attempt to compensate for operational differences among the individual FPAs of a multi-FPA IR imaging system with the use of methods that turn on spectral or temporal differencing can cause additional problems leading to false detection of target species. Among these problems are scene-motion-induced detection errors and parallax-caused errors that are not readily correctable and/or compensatable. Accordingly, there is a need to compensate for image data acquisition and processing errors caused by motion of elements within the scene being imaged. Various embodiments of data processing algorithms described herein address and fulfill the need to compensate for such motion-induced and parallax-induced image detection errors.

In particular, to reduce or minimize parallax-induced differences between the images produced with two or more predetermined FPAs, another difference image can be used that is formed from the images of at least two different FPAs to estimate parallax effects. Parallax error can be determined by comparing the images from two different FPAs where the position between the FPAs is known. The parallax can be calculated from the known relative position difference. Differences between the images from these two FPAs can be attributed to parallax, especially, if the FPA have the same spectral characteristics, for example have the same spectral filter or both have no spectral filters. Parallax error correction, however, can still be obtained from two FPAs that have different spectral characteristics or spectral filters, especially if the different spectral characteristics, e.g., the transmission spectra of the respective filters are known and/or negligible. Use of more than two FPAs or FPAs of different locations such as FPAs spaced farther apart can be useful. For example, when the spectral differencing of the image data is performed with the use of the difference between the images collected by the outermost two cameras in the array (such as, for example, the FPAs corresponding to filters 2 and 3 of the array of filters of FIG. 5A), a difference image referred to as a "difference image 2-3" is formed. In this case, the alternative "difference image 1-4" is additionally formed from the image data acquired by, for example, the alternative FPAs corresponding to filters 1 and 4 of FIG. 5A. Assuming or ensuring that both of these two alternative FPAs have approximately the same spectral sensitivity to the target species, the alternative "difference image 1-4" will highlight pixels corresponding to parallax-induced features in the image. Accordingly, based on positive determination that the same pixels are highlighted in the spectral "difference image 2-3" used for target species detection, a conclusion can be made that the image features corresponding to these pixels are likely to be induced by parallax and not the presence of target species in the imaged scene. It should be noted that compensation of parallax can also be performed using images created by individual re-imaging lenses, 128a, when using a single FPA or multiple FPA's as discussed above. FPAs spaced apart from each other in different directions can also be useful. Greater than 2, for example, 3 or 4, or more FPAs can be used to establish parallax for parallax correction. In certain embodiments two central FPAs and one corner FPA are used for parallax correction. These FPA may, in certain embodiments, have substantially similar or the same spectral characteristics, for example, have filters having similar or the same transmission spectrum or have no filter at all.

Another capability of the embodiments described herein is the ability to perform the volumetric estimation of a gas cloud. This can be accomplished by using (instead of compensating or negating) the parallax induced effects described above. In this case, the measured parallax between two or more similar spectral response images (e.g., two or more channels or FPAs) can be used to estimate a distance between the imaging system and the gas cloud or between the imaging system and an object in the field of view of the system. The parallax induced transverse image shift, d, between two images is related to the distance, z, between the cloud or object 110 and the imaging system according to the equation z=−sz'/d. Here, s, is the separation between two similar spectral response images, and z' is the distance to the image plane from the back lens. The value for z' is typically approximately equal to the focal length f of the lens of the imaging system. Once the distance z between the cloud and the imaging system is calculated, the size of the gas cloud can be determined based on the magnification, m=f/z, where each image pixel on the gas cloud, $\Delta x'$, corresponds to a physical size in object space $\Delta x = \Delta x'/m$. To estimate the volume of the gas cloud, a particular symmetry in the thickness of the cloud based on the physical size of the cloud can be assumed. For example, the cloud image can be rotated about a central axis running through the cloud image to create a three dimensional volume estimate of the gas cloud size. It is worth noting that in the embodiments described herein only a single imaging system is required for such volume estimation. Indeed, due to the fact that the information about the angle at which the gas cloud is seen by the system is decoded in the parallax effect, the image data includes the information about the imaged scene viewed by the system in association with at least two angles.

When the temporal differencing algorithm is used for processing the acquired imaging data, a change in the scene that is not caused by the target species can inadvertently be highlighted in the resulting image. In various embodiments, compensation for this error makes use of the temporal differencing between two FPAs that are substantially equally spectrally sensitive to the target species. In this case, the temporal difference image will highlight those pixels the intensity of which have changed in time (and not in wavelength). Therefore, subtracting the data corresponding to these pixels on both FPAs, which are substantially equally spectrally sensitive to the target species, to form the resulting image, excludes the contribution of the target species to the resulting image. The differentiation between (i) changes in the scene due to the presence of target species and (ii) changes in the scene caused by changes in the background not associated with the target species is, therefore, possible. In some embodiments, these two channels having the same or substantially similar spectral response so as be substantially equally spectrally sensitive to the target species may comprise FPAs that operate using visible light. It should also be noted that, the data acquired with a visible light FPA (when present as part of the otherwise IR imaging system) can also be used to facilitate such differentiation and compensation of the motion-caused imaging errors. Visible cameras generally have much lower noise figure than IR cameras (at least during daytime). Consequently, the temporal difference image obtained with the use of image data from the visible light FPA can be quite accurate. The visible FPA can be used to compensate for motion in the system as well as many potential false-alarms in the scene due to motion caused by people, vehicles, birds, and steam, for example, as long as the moving object can be observed in the visible region of the spectra. This has the added benefit of providing an additional level of false alarm suppression without reducing the sensitivity of the system since many targets such as gas clouds cannot be observed in the visible spectral region. In various implementations, an IR camera can be used to compensate for motion artifacts.

Another method for detection of the gases is to use a spectral unmixing approach. A spectral unmixing approach assumes that the spectrum measured at a detector pixel is composed of a sum of component spectra (e.g., methane and other gases). This approach attempts to estimate the relative weights of these components needed to derive the measurement spectrum. The component spectra are generally taken from a predetermined spectral library (for example, from data collection that has been empirically assembled), though sometimes one can use the scene to estimate these as well (often called "endmember determination"). In various embodiments, the image obtained by the detector pixel is a radiance spectrum and provides information about the brightness of the object. To identify the contents of a gas cloud in the scene and/or to estimate the concentration of the various gases in the gas cloud, an absorption/emission spectrum of the various gases of interest can be obtained by comparing the measured brightness with an estimate of the expected brightness. The spectral unmixing methodology can also benefit from temporal, parallax, and motion compensation techniques.

In various embodiments, a method of identifying the presence of a target species in the object includes obtaining the radiance spectrum (or the absorption spectrum) from the object in a spectral region indicative of the presence of the target species and calculating a correlation (e.g., a correlation coefficient) by correlating the obtained radiance spectrum (or the absorption spectrum) with a reference spectrum for the target species. The presence or absence of the target species can be determined based on an amount of correlation (e.g., a value of correlation coefficient). For example, the presence of the target species in the object can be confirmed if the amount of correlation or the value of correlation coefficient is greater than a threshold. In various implementations, the radiance spectrum (or the absorption spectrum) can be obtained by obtaining a spectral difference image between a filtered optical channel and/or another filtered optical channel/unfiltered optical channel or any combinations thereof.

For example, an embodiment of the system configured to detect the presence of methane in a gas cloud comprises optical components such that one or more of the plurality of optical channels is configured to collect IR radiation to provide spectral data corresponding to a discrete spectral band located in the wavelength range between about 7.9 µm and about 8.4 µm corresponding to an absorption peak of methane. The multispectral data obtained in the one or more optical channels can be correlated with a predetermined absorption spectrum of methane in the wavelength range between about 7.9 µm and 8.4 µm. In various implementations, the predetermined absorption spectrum of methane can be saved in a database or a reference library accessible by the system. Based on an amount of correlation (e.g., a value of correlation coefficient), the presence or absence of methane in the gas cloud can be detected.

Examples of Practical Embodiments and Operation

The embodiment 300 of FIG. 3 is configured to employ 12 optical channels and 12 corresponding microbolometer FPAs 336 to capture a video sequence substantially immediately after performing calibration measurements. The video sequence corresponds to images of a standard laboratory scene and the calibration measurements are performed with the use of a reference source including two shutters, as discussed above, one at room temperature and one 5° C. above room temperature. The use of 12 FPAs allows increased chance of simultaneous detection and estimation of the concentrations of about 8 or 9 gases present at the scene. In various embodiments, the number of FPAs 336 can vary, depending on the balance between the operational requirements and consideration of cost.

Due to the specifics of operation in the IR range of the spectrum, the use of the so-called noise-equivalent temperature difference (or NETD) is preferred and is analogous to the SNR commonly used in visible spectrum instruments. The array of microbolometer FPAs 336 is characterized to perform at NETD≤72 mK at an f-number of 1.2. Each measurement was carried out by summing four consecutive frames, and the reduction in the NETD value expected due to such summation would be described by corresponding factor of $\sqrt{4}=2$. Under ideal measurement conditions, therefore, the FPA NETD should be about 36 mK.

It is worth noting that the use of optically-filtered FPAs in various embodiments of the system described herein can provide a system with higher number of pixels. For example, embodiments including a single large format microbolometer FPA array can provide a system with large number of pixels. Various embodiments of the systems described herein can also offer a high optical throughput for a substantially low number of optical channels. For example, the systems described herein can provide a high optical throughput for a number of optical channels between 4 and 50. By having a lower number of optical channels (e.g., between 4 and 50 optical channels), the systems described herein have wider spectral bins which allows the signals acquired within each spectral bin to have a greater integrated intensity.

An advantage of the embodiments described herein over various scanning based hyperspectral systems that are configured for target species detection (for example, gas cloud detection) is that, the entire spectrum can be resolved in a snapshot mode (for example, during one image frame acquisition by the FPA array). This feature enables the embodiments of the imaging systems described herein to take advantage of the compensation algorithms such as the parallax and motion compensation algorithms mentioned above. Indeed, as the imaging data required to implement these algorithms are collected simultaneously with the target-species related data, the compensation algorithms are carried out with respect to target-species related data and not with respect to data acquired at another time interval. This rapid data collection thus improves the accuracy of the data compensation process. In addition, the frame rate of data acquisition is much higher. For example, embodiments of the imaging system described herein can operate at video rates from about 5 Hz and higher. For example, various embodiments described herein can operate at frame rates from about 5 Hz to about 60 Hz or 200 Hz. Thus, the user is able to recognize in the images the wisps and swirls typical of gas mixing without blurring out of these dynamic image features and other artifacts caused by the change of scene (whether spatial or spectral) during the lengthy measurements. In contradistinction, scanning based imaging systems involve image data acquisition over a period of time exceeding a single-snap-shot time and can, therefore, blur the target gas features in the image and inevitably reduce the otherwise achievable sensitivity of the detection. This result is in contrast to embodiments of the imaging system described herein that are capable of detecting the localized concentrations of gas without it being smeared out with the areas of thinner gas concentrations. In addition, the higher frame rate also enables a much faster response rate to a leak of gas (when detecting such leak is the goal). For example, an alarm can trigger within fractions of a second rather than several seconds.

Figure 7:
FIG. 7 is a set of video-frames illustrating operability of an embodiment of the system used for gas detection.

To demonstrate the operation and gas detection capability of the imaging systems described herein, a prototype was constructed in accordance with the embodiment 300 of FIG. 3A and used to detect a hydrocarbon gas cloud of propylene at a distance of approximately 10 feet. FIG. 7 illustrates video frames 1 through 12 representing gas-cloud-detection output 710 (seen as a streak of light) in a sequence from t=1 to t=12. The images 1 through 12 are selected frames taken from a video-data sequence captured at a video-rate of 15 frames/sec. The detected propylene gas is shown as a streak of light 710 (highlighted in red) near the center of each image. The first image is taken just prior to the gas emerging from the nozzle of a gas-contained, while the last image represents the system output shortly after the nozzle has been turned off.

Figure 8A:
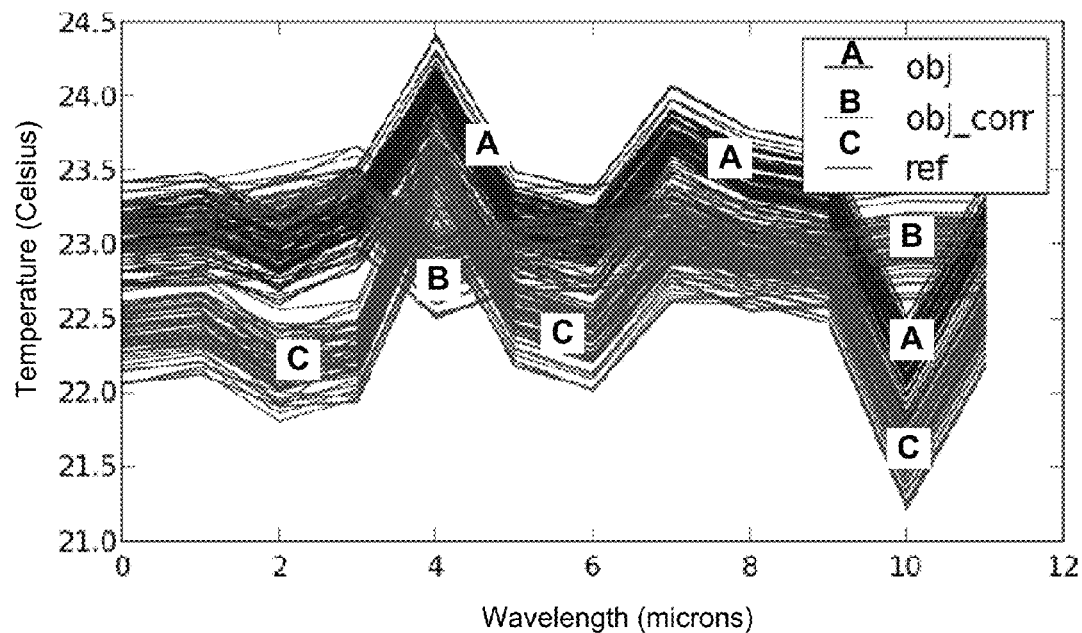
FIGS. 8A and 8B are plots (on axes of wavelength in microns versus the object temperature in Celsius representing effective optical intensity of the object) illustrating results of dynamic calibration of an embodiment of the system.
Figure 8B:
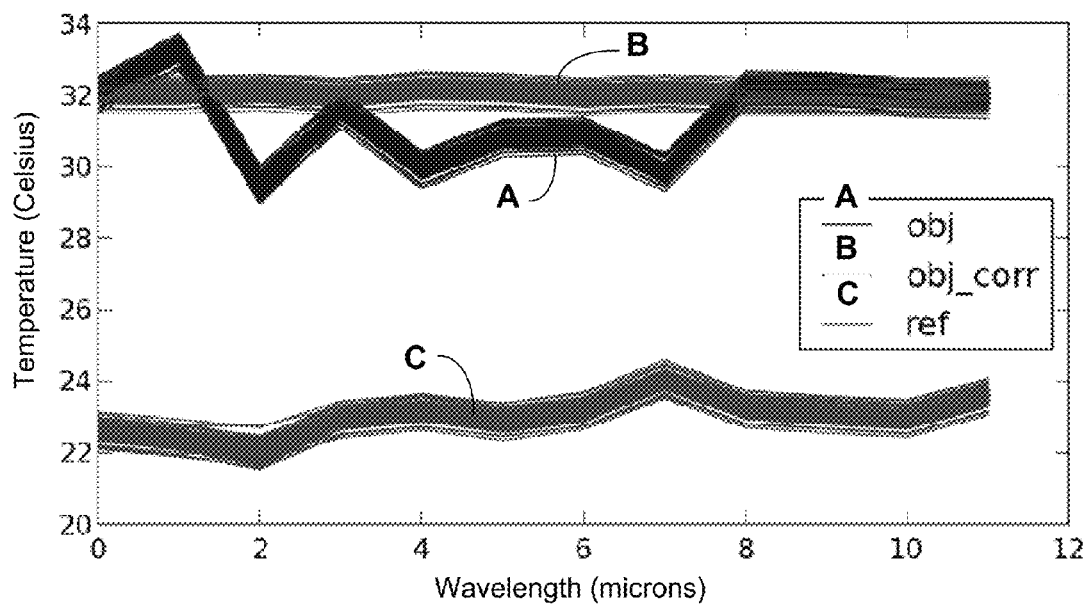

The same prototype of the system can also demonstrate the dynamic calibration improvement described above by imaging the scene surrounding the system (the laboratory) with known temperature differences. The result of implementing the dynamic correction procedure is shown in FIGS. 8A, 8B, where the curves labeled "obj" (or "A") represent temperature estimates of an identified region in the scene. The abscissa in each of the plots of FIGS. 8A, 8B indicates the number of a FPA, while the ordinate corresponds to temperature (in degrees C.). Accordingly, it is expected that when all detector elements receive radiant data that, when interpreted as the object's temperature, indicates that the object's temperature perceived by all detector elements is the same, any given curve would be a substantially flat line. Data corresponding to each of the multiple "obj" curves are taken from a stream of video frames separated from one another by about 0.5 seconds (for a total of 50 frames). The recorded "obj" curves shown in FIG. 8A indicate that the detector elements disagree about the object's temperature, and that difference in object's temperature perceived by different detector elements is as high as about 2.5° C. In addition, all of the temperature estimates are steadily drifting in time, from frame to frame. The curves labeled "ref" (or "C") correspond to the detectors' estimates of the temperature of the aperture 338 of the embodiment 300 of FIG. 3A. The results of detection of radiation carried out after each detector pixel has been subjected to the dynamic calibration procedure described above are expressed with the curved labeled "obj corr" (or "B"). Now, the difference in estimated temperature of the object among the detector elements is reduced to about 0.5° C. (thereby improving the original reading at least by a factor of 5).

FIG. 8B represents the results of similar measurements corresponding to a different location in the scene (a location which is at a temperature about 9° C. above the estimated temperature of the aperture 338 of FIG. 3A). As shown, the correction algorithm discussed above is operable and effective and applicable to objects kept at different temperature. Accordingly, the algorithm is substantially temperature independent.

Dynamic Calibration Elements and References

Figure 9A:
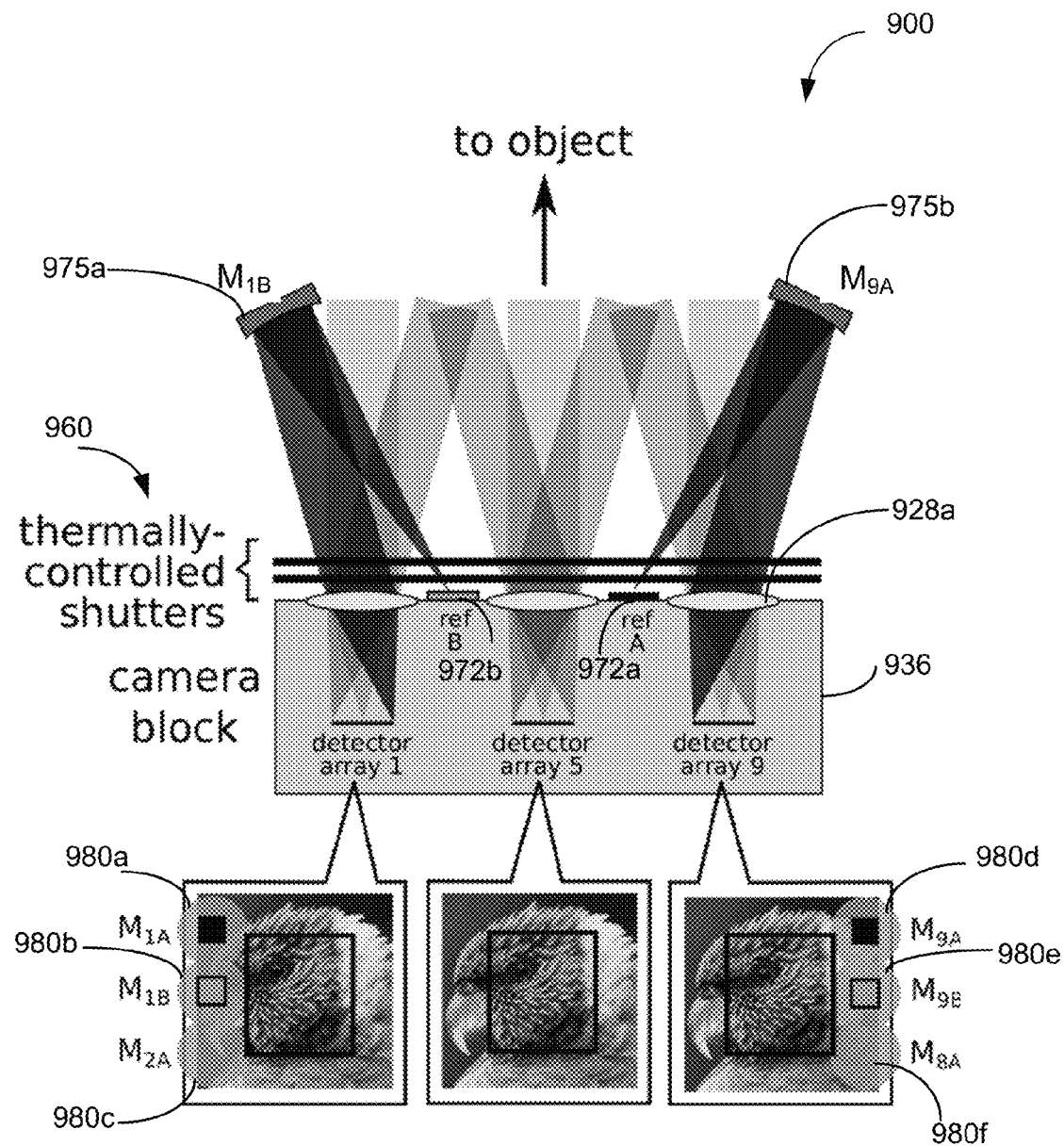
FIGS. 9A and 9B illustrate a cross-sectional view of different embodiments of an imaging system comprising an arrangement of reference sources and mirrors that can be used for dynamic calibration.
Figure 9B:
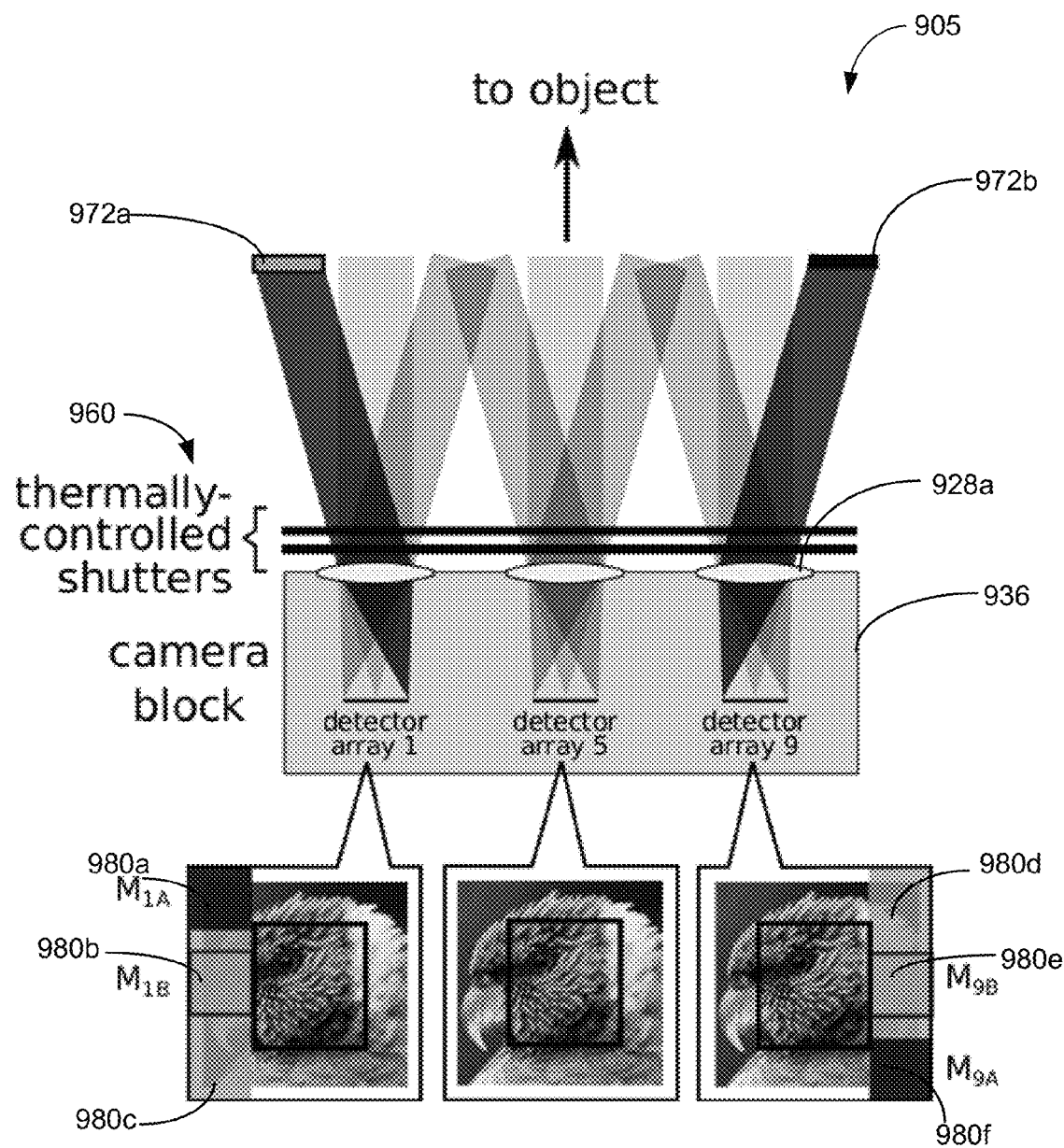

FIGS. 9A and 9B illustrates schematically different implementations 900 and 905 respectively of the imaging system that include a variety of temperature calibration elements to facilitate dynamic calibration of the FPAs. The temperature calibration elements can include mirrors 975a, 975b (represented as $M_{1A}$, $M_{9A}$, etc.) as well as reference sources 972a and 972b. The implementation 900 can be similarly configured as the embodiment 300 and include one or more front objective lens, a divided aperture, one or more spectral filters, an array of imaging lenses 928a and an imaging element 936. In various implementations, the imaging element 936 (e.g., camera block) can include an array of cameras. In various implementations, the array of cameras can comprise an optical FPA unit. The optical FPA unit can comprise a single FPA, an array of FPAs. In various implementations, the array of cameras can include one or more detector arrays represented as detector array 1, detector array 5, detector array 9 in FIGS. 9A and 9B. In various embodiments, the FOV of each of the detector arrays 1, 5, 9 can be divided into a central region and a peripheral region. Without any loss of generality, the central region of the FOV of each of the detector arrays 1, 5, 9 can include the region where the FOV of all the detector arrays 1, 5, 9 overlap. In the embodiment illustrated in FIG. 9A, some temperature-calibration elements, namely, reference sources 972a and 972b are placed at a distance from the detector arrays 1, 5, 9, for example, and mirrors to image them onto the detector arrays are then placed at the location of the scene reference aperture (e.g., 338 of FIG. 3A).

In FIG. 9A, the temperature-calibration elements 975a and 975b comprise mirrors that reflect radiation from the reference sources 972a and 972b (represented as ref A and ref B). The mirrors 975a and 975b can be disposed away from the central FOV of the detector arrays 1, 5, 9 such that the central FOV is not blocked or obscured by the image of the reference source 972a and 972b. In various implementations, the FOV of the detector array 5 could be greater than the FOV of the detector arrays 1 and 9. In such implementations, the mirrors 975a and 975b can be disposed away from the central FOV of the detector array 5 at a location such that the reference source 972a and 972b is imaged by the detector array 5. The mirrors 975a and 975b may comprise imaging optical elements having optical power that image the reference sources 972a and 972b onto the detector arrays 1 and 9. In this example, the reference sources 972a and 972b can be disposed in the same plane as the re-imaging lenses 928a, however, the reference sources 972a and 972b can be disposed in a different plane or in different locations. For example, the reference sources 972a and 972b can be disposed in a plane that is conjugate to the plane in which the detector array 1, detector array 5, and detector array 9 are disposed such that a focused image of the reference sources 972a and 972b is formed by the detector arrays. In some implementations, the reference sources 972a and 972b can be disposed in a plane that is spaced apart from the conjugate plane such that a defocused image of the reference sources 972a and 972b is formed by the detector arrays. In various implementations, the reference sources 972a and 972b need not be disposed in the same plane.

As discussed above, in some embodiments, the reference sources 972a and 972b are imaged onto the detector array 1 and detector array 9, without much blur such that the reference sources 972a and 972b are focused. In contrast, in other embodiments, the image of the formed of reference sources 972a and 972b on the detector array 1, and detector array 9 are blurred such that the reference sources 972a and 972b are defocused, and thereby provide some averaging, smoothing, and/or low pass filtering. The reference sources 972a and 972b may comprise a surface of known temperature and may or may not include a heater or cooler attached thereto or in thermal communication therewith. For example, the reference source 972a and 972b may comprises heaters and coolers respectively or may comprise a surface with a temperature sensor and a heater and sensor respectively in direct thermal communication therewith to control the temperature of the reference surface. In various implementations, the reference sources 972a and 972b can include a temperature controller configured to maintain the reference sources 972a and 972b at a known temperature. In some implementations, the reference sources 972a and 972b can be associated with one or more sensors that measure the temperature of the reference sources 972a and 972b and communicate the measured temperature to the temperature controller. In some implementations, the one or more sensors can communicate the measured temperature to the data-processing unit. In various implementations, the reference sources 972a and 972b may comprise a surface of unknown temperature. For example, the reference sources may comprise a wall of a housing comprising the imaging system. In some implementations, the reference sources 972a and 972b comprising a surface need not be associated with sensors, temperature controllers. However, in other implementations, the reference sources 972a and 972b comprising a surface can be associated with sensors, temperature controllers.

In FIG. 9B, the temperature-calibration elements comprise temperature-controlled elements 972a and 972b (e.g., a thermally controlled emitter, a heating strip, a heater or a cooler) disposed a distance from the detector arrays 1, 5, 9. In various embodiments, the temperature-controlled elements 972a and 972b can be disposed away from the central FOV of the detector arrays 1, 5, 9 such that the central FOV is not blocked or obscured by the image of the reference source 972a and 972b. The radiation emitted from the reference sources 972a and 972b is also imaged by the detector array 936 along with the radiation incident from the object. Depending on the position of the reference sources 972a and 972b the image obtained by the detector array of the reference sources can be blurred (or defocused) or sharp (or focused). The images 980a, 980b, 980c, 980d, 980e and 980f of the temperature-controlled elements 972a and 972b can be used as a reference to dynamically calibrate the one or more cameras in the array of cameras.

In the implementations depicted in FIGS. 9A and 9b, the detector arrays 1, 5 and 9 are configured to view (or image) both the reference sources 972a and 972b. Accordingly, multiple frames (e.g., every or substantially every frame) within a sequence of images contains one or more regions in the image in which the object image has known thermal and spectral properties. This allows multiple (e.g., most or each) cameras within the array of cameras to be calibrated to agree with other (e.g., most or every other) camera imaging the same reference source(s) or surface(s). For example, detector arrays 1 and 9 can be calibrated to agree with each other. As another example, detector arrays 1, 5 and 9 can be calibrated to agree with each other. In various embodiments, the lenses 928a provide blurred (or defocused) images of the reference sources 972a, 972b on the detector arrays 1 and 9 because the location of the reference sources are not exactly in a conjugate planes of the detector arrays 1 and 9. Although the lenses 928a are described as providing blurred or defocused images, in various embodiments, reference sources or surfaces are imaged on the detectors arrays 1, 5, 9 without such blur and defocus and instead are focused images. Additionally optical elements may be used, such as for example, the mirrors shown in FIG. 9A to provide such focused images.

The temperature of the reference sources 972b, 972a can be different. For example, the reference source 972a can be at a temperature $T_A$, and the reference source 972b can be at a temperature $T_B$ lower than the temperature $T_A$. A heater can be provided under the temperature-controlled element 972a to maintain it at a temperature $T_A$, and a cooler can be provided underneath the temperature-controlled element 972b to maintain it at a temperature $T_B$. In various implementations, the embodiments illustrated in FIGS. 9A and 9B can be configured to image a single reference source 972 instead of two references sources 972a and 972b maintained at different temperatures. It is understood that the single reference source need not be thermally controlled. For example, in various implementations, a plurality of detectors in the detector array can be configured to image a same surface of at least one calibration element whose thermal and spectral properties are unknown. In such implementations, one of the plurality of detectors can be configured as a reference detector and the temperature of the surface of the at least one calibration element imaged by the plurality of detectors can be estimated using the radiance spectrum obtained by the reference detector. The remaining plurality of detectors can be calibrated such that their temperature and/or spectral measurements agree with the reference detector. For example, detector arrays 1 and 9 can be calibrated to agree with each other. As another example, detector arrays 1, 5 and 9 can be calibrated to agree with each other.

The reference sources 972a and 972b can be coated with a material to make it behave substantially as a blackbody (for which the emission spectrum is known for any given temperature). If a temperature sensor is used at the location of each reference source, then the temperature can be tracked at these locations. As a result, the regions in the image of each camera (e.g., on the detector arrays 1 and 9) in which the object has such known temperature (and, therefore, spectrum) can be defined. A calibration procedure can thus be used so that most of the cameras (if not every camera) so operated agrees, operationally, with most or every other camera, for objects at the temperatures represented by those two sources. Calibrating infrared cameras using sources at two different temperatures is known as a "two-point" calibration, and assumes that the measured signal at a given pixel is linearly related to the incident irradiance. Since this calibration can be performed during multiple, more, or even every frame of a sequence, it is referred to as a "dynamic calibration".

An example of the dynamic calibration procedure is as follows. If there is a temperature sensor on the reference sources or reference surface, then the temperature measurements obtained by these temperature sensors can be used to determine their expected emission spectra. These temperature measurements are labeled as $T_A[R]$, $T_B[R]$, and $T_C[R]$ for the "reference temperatures" of sources/surfaces A, B, and C. These temperature measurements can be used as scalar correction factors to apply to the entire image of a given camera, forcing it to agree with the reference temperatures. Correcting the temperature estimate of a given pixel from T to T' can use formulae analogous to those discussed below in reference to FIGS. 10A, 10B, 10C. If no direct temperature sensor is used, then one of the cameras can be used instead. This camera can be referred to as the "reference camera". In this case, the same formulae as those provided below can be used, but with $T_A[R]$ and $T_B[R]$ representing the temperatures of the reference sources/surfaces A and B as estimated by the reference camera. By applying the dynamic calibration correction formulae, all of the other cameras are forced to match the temperature estimates of the reference camera.

In the configuration illustrated in FIG. 9B, the reference sources 972*a* and 972*b* are placed such that the images of the sources on the detector arrays are blurred. The configuration illustrated in FIG. 9A is similar to the system 400 illustrated in FIG. 4 where the reference sources are placed at an intermediate image plane (e.g., a conjugate image plane). In this configuration, the array of reference apertures, similar to reference apertures 438*a* in FIG. 4, will have an accompanying array of reference sources or reference surfaces such that the reference sources or surfaces (e.g., each reference source or surface) are imaged onto a camera or a detector array such as FPAs 1, 5, 9. With this approach, the reference source or surface images are at a conjugate image plane and thus are not appreciably blurred, so that their images can be made to block a smaller portion of each camera's field of view.

A "static" calibration (a procedure in which the scene is largely blocked with a reference source such as the moving shutters 960 in FIGS. 9A and 9B, so that imaging of a unknown scene cannot be performed in parallel with calibration) allows a plurality of the cameras (for example, most or each camera) to accurately estimate the temperature of a plurality of elements (for example, most or each element in the scene) immediately after the calibration is complete. It cannot, however, prevent the cameras' estimates from drifting away from one another during the process of imaging an unknown scene. The dynamic calibration can be used to reduce or prevent this drift, so that all cameras imaging a scene can be forced to agree on the temperature estimate of the reference sources/surfaces, and adjust this correction during every frame.

Figure 10A:
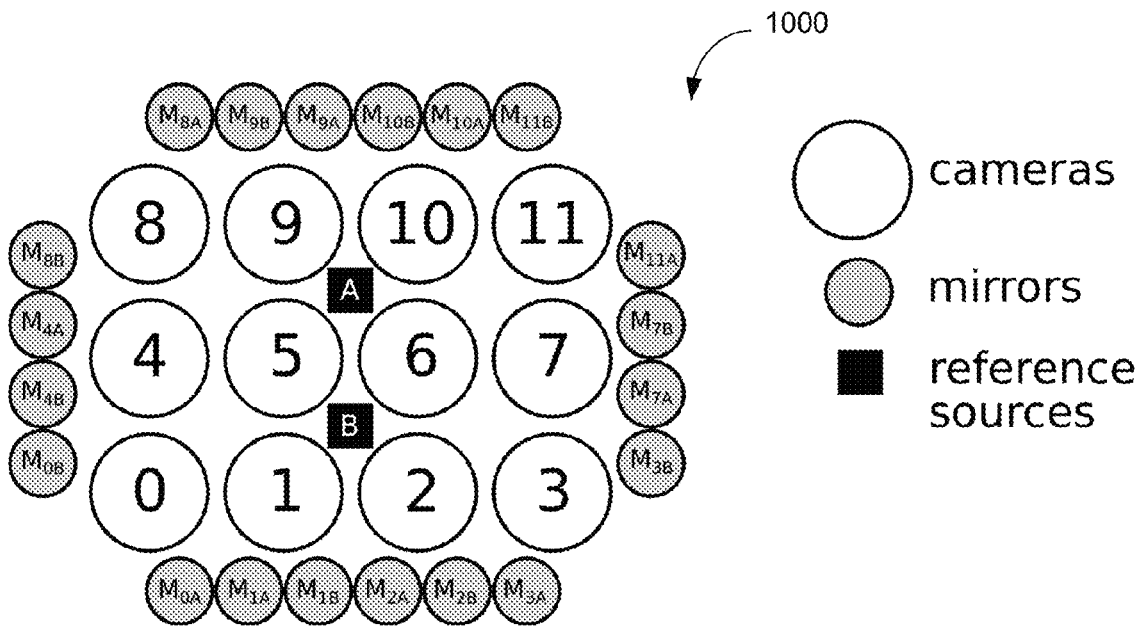
FIGS. 10A-10C illustrate a plan view of different embodiments of an imaging system comprising an arrangement of reference sources and mirrors that can be used for dynamic calibration.

FIG. 10A illustrates schematically a related embodiment 1000 of the imaging system, in which one or more mirrors $M_{OA}$, $M_{11A}$ and $M_{OB}$, ... $M_{11B}$ are placed within the fields of view of one or more cameras 0, ..., 11, partially blocking the field of view. The cameras 0, ..., 11 are arranged to form an outer ring of cameras including cameras 0, 1, 2, 3, 7, 11, 10, 9, 8 and 4 surrounding the central cameras 5 and 6. In various implementations, the FOV of the central cameras 5 and 6 can be less than or equal to the FOV of the outer ring of cameras 0, 1, 2, 3, 7, 11, 10, 9, 8 and 4. In such implementations, the one or more mirrors $M_{OA}$, $M_{11A}$ and $M_{OB}$, ... $M_{11B}$ can be placed outside the central FOV of the cameras 5 and 6 and is placed in a peripheral FOV of the cameras outer ring of cameras 0, 1, 2, 3, 7, 11, 10, 9, 8 and 4 which does not overlap with the central FOV of the cameras 5 and 6 such that the reference sources A and B are not imaged by the cameras 5 and 6. In various implementations, the FOV of the central cameras 5 and 6 can be greater than the FOV of the outer ring of cameras 0, 1, 2, 3, 7, 11, 10, 9, 8 and 4. In such implementations, the one or more mirrors $M_{OA}$, $M_{11A}$ and $M_{OB}$, $M_{11B}$ can be placed in a peripheral FOV of the cameras 5 and 6 which does overlap with the central FOV of the outer ring of cameras 0, 1, 2, 3, 7, 11, 10, 9, 8 and 4 such that the reference sources A and B are imaged by the cameras 5 and 6.

This design is an enhancement to the systems 300 and 400 shown in FIGS. 3A and 4A. In the system 1000 shown in FIG. 10A, an array of two or more imaging elements (curved mirrors, for example) is installed at a distance from the FPAs, for example, in the plane of the reference aperture 160 shown in FIG. 3A. These elements (mirror or imaging elements) are used to image one or more temperature-controlled reference sources A and B onto the detector elements of two or more of the cameras. The primary difference between embodiment 1000 and embodiment 300 or 400 is that now a plurality or most or all of the outer ring of cameras in the array can image both the reference sources A and B instead of imaging one of the two reference source A and B. Accordingly, most or all of the outer ring of cameras image an identical reference source or an identical set of reference sources (e.g., both the reference sources A and B) rather than using different reference sources for different cameras or imaging different portions of the reference sources as shown in FIGS. 3A and 4A. Thus, this approach improves the robustness of the calibration, as it eliminates potential failures and errors due to the having additional thermal sensors estimating each reference source.

Figure 10B:
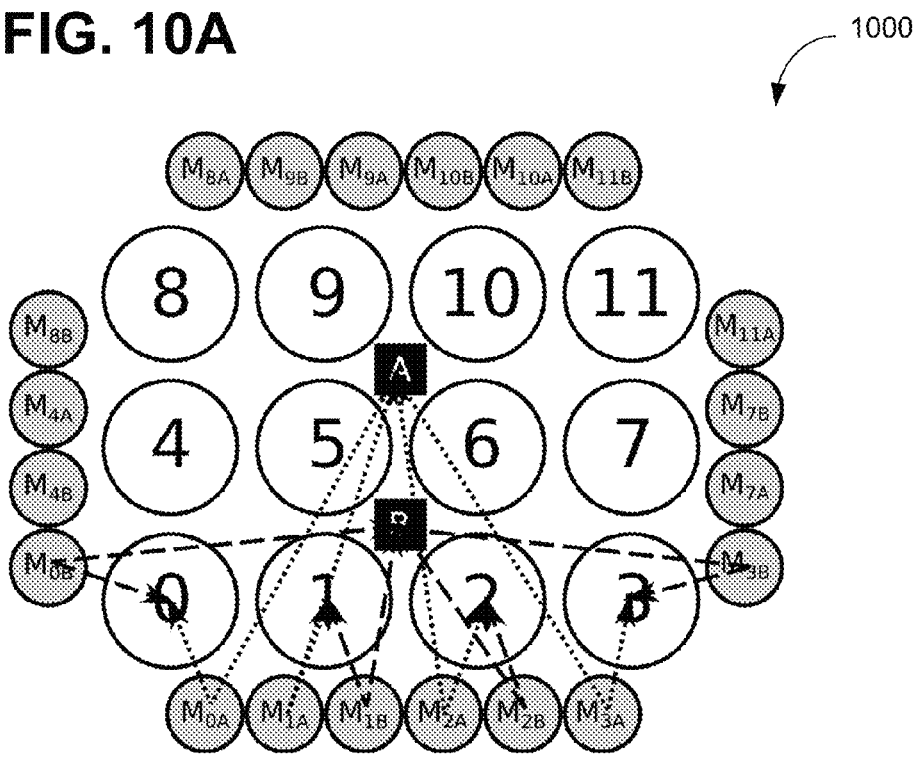

The imaging elements in the system 1000 (shown as mirrors in FIGS. 10A and 10B) image one or more controlled-temperature reference sources or a surface of a calibration element (shown as A and B in FIGS. 10A and 10B) into the blocked region of the cameras' fields of view. FIG. 10B shows an example in which mirror $M_{OA}$ images reference source/surface A onto camera 0, and mirror $M_{OB}$ images reference source/surface B onto camera 0, and likewise for cameras 1, 2, and 3. This way, each of the mirrors is used to image a reference source/surface onto a detector array of a camera, so that many, most, or every frame within a sequence of images contains one or more regions in the image in which the object image has known thermal and spectral properties. This approach allows most of the camera, if not each camera, within the array of cameras to be calibrated to agree with most or every other camera imaging the same reference source or sources. For example, cameras 0, 1, 2, 3, 7, 11, 10, 9, 8 and 4 can be calibrated to agree with each other. As another example, cameras 0, 1, 2 and 3 can be calibrated to agree with each other. As yet another example, cameras 0, 1, 2, 3, 7, 11, 10, 9, 8, 4, 5 and 6 can be calibrated to agree with each other. Accordingly, in various implementations, two, three, four, five, six, seven, eight, nine, ten, eleven or twelve cameras can be calibrated to agree with each other. In certain embodiments, however, not all the cameras are calibrated to agree with each other. For example, one, two, or more cameras may not be calibrated to agree with each other while others may be calibrated to agree with each other. In various embodiments, these mirrors may be configured to image the reference sources/surfaces A and B onto different respective pixels a given FPA. Without any loss of generality, FIGS. 10A and 10B represent a top view of the embodiment shown in FIG. 9A.

Figure 10C:
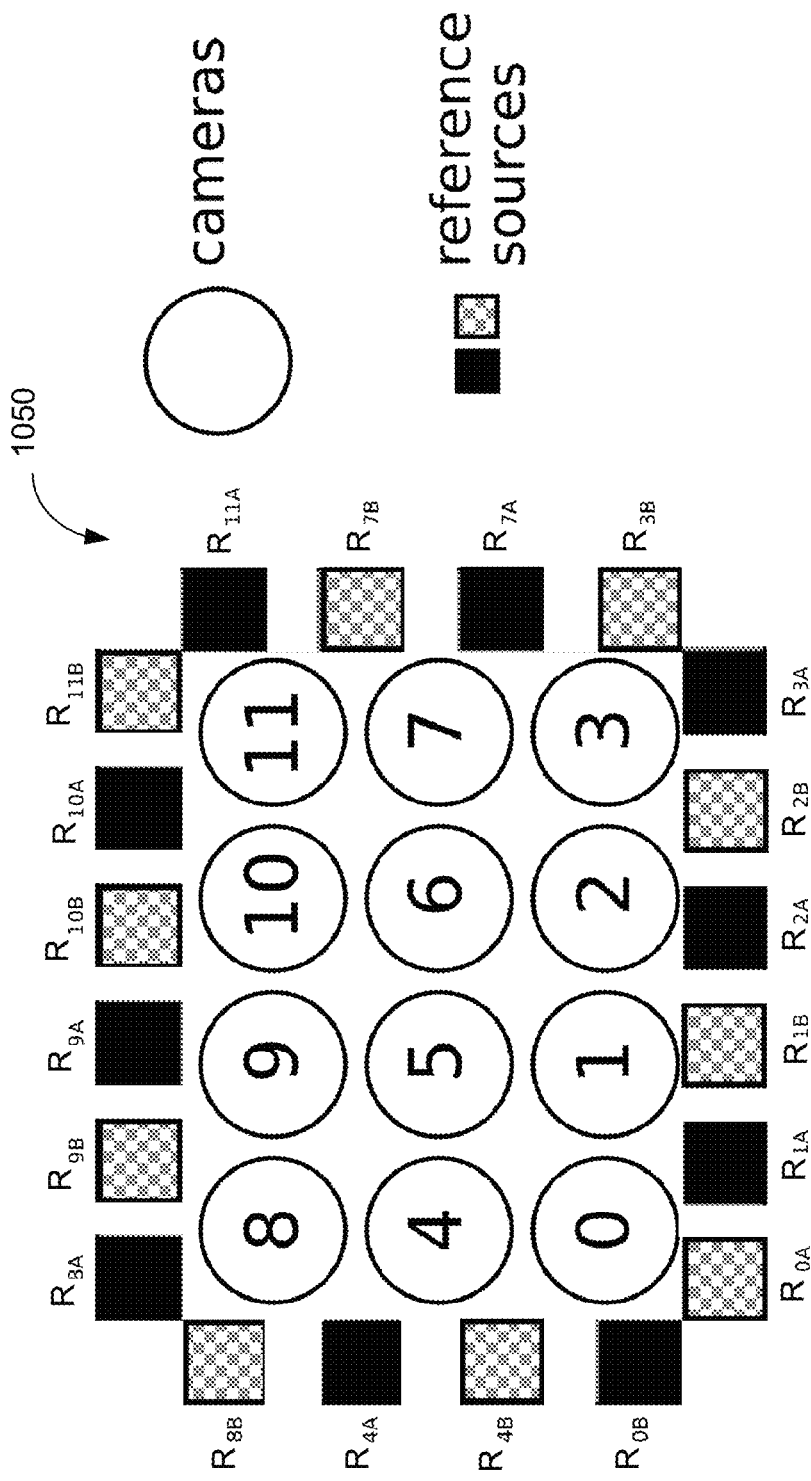

FIG. 10C illustrates schematically a related embodiment 1050 of the imaging system, in which one or more reference sources $R_{OA}$, ..., $R_{11A}$ and $R_{OB}$, ..., $R_{11B}$ are disposed around the array of detectors 0, ..., 11. In various implementations, the one or more reference sources $R_{0A}, \ldots, R_{11A}$ and $R_{0B}, \ldots, R_{11B}$ can be a single reference source that is images by the detectors 0, ..., 11. In various implementations, central detector arrays 5 and 6 can have a FOV that is equal to or lesser than the FOV of the outer ring of the detectors 0, 1, 2, 3, 7, 11, 10, 9, 8 and 4. In such implementations, the reference sources $R_{0A}, \ldots, R_{11A}$ can be disposed away from the central FOV of the detector arrays 5 and 6 such that the radiation from the reference sources $R_{0A}, \ldots, R_{11A}$ is imaged only by the outer ring of detectors 0, 1, 2, 3, 7, 11, 10, 9, 8 and 4. In various implementations, central detector arrays 5 and 6 can have a FOV that is greater than the FOV of the outer ring of the detectors 0, 1, 2, 3, 7, 11, 10, 9, 8 and 4. In such implementations, the reference sources $R_{0A}, \ldots, R_{11A}$ can be disposed in the peripheral FOV of the detector arrays 5 and 6 such that the radiation from the reference sources $R_{0A}, \ldots, R_{11A}$ is imaged only by the outer ring of detectors 0, 1, 2, 3, 7, 11, 10, 9, 8 and 4. The radiation from the reference sources $R_{0A}, \ldots, R_{11A}$ is therefore imaged by the outer ring of detectors 0, 1, 2, 3, 7, 11, 10, 9, 8 and 4 as well as central cameras 5 and 6. Without any loss of generality, FIG. 10C represents a top view of the embodiment shown in FIG. 9B.

In various implementations, one can use a heater underneath, adjacent to, or in thermal communication with reference source/surface A to give it a higher temperature $T_A$, and a cooler underneath, adjacent to, or in thermal communication with reference source B to give it a lower temperature $T_B$. In various implementations, the embodiments illustrated in FIGS. 10A, 10B and 10C can be configured to image a single reference source A instead of two references sources A and B maintained at different temperatures. As discussed above, the embodiments illustrated in FIGS. 10A, 10B and 10C can be configured to image a same surface of a calibration element. In such implementations, the temperature of the surface of the calibration element need not be known. Many, most or each reference source/surface can be coated with a material to make it behave approximately as a blackbody, for which the emission spectrum is known for any given temperature. If many, most, or each camera in the array of cameras images both of references A and B, so that there are known regions in the image of these cameras in which the object has a known temperature (and therefore spectrum). Then one can perform a calibration procedure. This procedure can provide that many, most or every camera so operated agrees with various, most, or every other camera, for objects at the temperatures represented by those two sources. For example, two, three, four, five, six, seven, eight, nine, ten, eleven or twelve cameras can be calibrated to agree with each other. In certain embodiments, however, not all the cameras are calibrated to agree with each other. For example, one, two, or more cameras may not be calibrated to agree with each other while others may be calibrated to agree with each other. As discussed above, calibration of infrared cameras using sources at two different temperatures is known as a "two-point" calibration, and assumes that the measured signal at a given pixel is linearly related to the incident irradiance.

The dynamic calibration is used to obtain a corrected temperature T' from the initial temperature T estimated at each pixel in a camera using the following formulae:

$$T'[x,y,c]=(T[x,y,c]-T_A[R])G[c]+T_A[R]$$

where is $T_A[R]$ is a dynamic offset correction factor, and, $$G[c] = \frac{T_B[R] - T_A[R]}{T_B[c] - T_A[c]},$$

is a dynamic gain correction factor. The term c discussed above is a camera index that identifies the camera whose data is being corrected.

References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and in possible connection with a figure, is intended to provide a complete description of all features of the invention.

In the drawings like numbers are used to represent the same or similar elements wherever possible. The depicted structural elements are generally not to scale, and certain components are enlarged relative to the other components for purposes of emphasis and understanding. It is to be understood that no single drawing is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented is this view, for purposes of simplifying the given drawing and discussion, and to direct the discussion to particular elements that are featured in this drawing. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed. Furthermore, the described single features, structures, or characteristics of the invention may be combined in any suitable manner in one or more further embodiments.

The features recited in claims appended to this disclosure are intended to be assessed in light of the disclosure as a whole, including features disclosed in prior art to which reference is made.

At least some elements of a device of the invention can be controlled—and at least some steps of a method of the invention can be effectuated, in operation—with a programmable processor governed by instructions stored in a memory. The memory may be random access memory (RAM), read-only memory (ROM), flash memory or any other memory, or combination thereof, suitable for storing control software or other instructions and data. Those skilled in the art should also readily appreciate that instructions or programs defining the functions of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer networks. In addition, while the invention may be embodied in software, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

While examples of embodiments of the system and method of the invention have been discussed in reference to the gas-cloud detection, monitoring, and quantification (including but not limited to greenhouse gases such as Carbon Dioxide, Carbon Monoxide, Nitrogen Oxide as well as hydrocarbon gases such as Methane, Ethane, Propane, n-Butane, iso-Butane, n-Pentane, iso-Pentane, neo-Pentane, Hydrogen Sulfide, Sulfur Hexafluoride, Ammonia, Benzene, p- and m-Xylene, Vinyl chloride, Toluene, Propylene oxide, Propylene, Methanol, Hydrazine, Ethanol, 1,2-dichloroethane, 1,1-dichloroethane, Dichlorobenzene, Chlorobenzene, to name just a few), embodiments of the invention can be readily adapted for other chemical detection applications. For example, detection of liquid and solid chemical spills, biological weapons, tracking targets based on their chemical composition, identification of satellites and space debris, ophthalmological imaging, microscopy and cellular imaging, endoscopy, mold detection, fire and flame detection, and pesticide detection are within the scope of the invention.

As used herein, a phrase referring to "at least one of" a list of items refers to any combination of those items, including single members. As an example, "at least one of: a, b, or c" is intended to cover: a, b, c, a-b, a-c, b-c, and a-b-c.

If implemented in software, the functions may be stored on or transmitted over as one or more instructions or code on a computer-readable medium. The steps of a method or algorithm disclosed herein may be implemented in a processor-executable software module which may reside on a computer-readable medium. Computer-readable media includes both computer storage media and communication media including any medium that can be enabled to transfer a computer program from one place to another. A storage media may be any available media that may be accessed by a computer. By way of example, and not limitation, such computer-readable media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection can be properly termed a computer-readable medium. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above also may be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

Certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

What is claimed is:

1. An infrared (IR) imaging system, the imaging system comprising:
   a plurality of cameras;
   at least one thermal reference source having a known temperature;
   a plurality of mirrors configured to reflect radiation from the at least one thermal reference source towards the plurality of cameras; and
   a data-processing unit comprising a processor, the imaging system configured to:
      acquire with the plurality of cameras one or more image frames of an object, a plurality of the one or more image frames having regions with the known temperature that corresponds to the at least one reference source; and
      apply a dynamic calibration correction to the plurality of cameras based on the plurality of the one or more image frames having regions with the known temperature to allow every camera in the plurality of cameras to be calibrated to agree with every other camera in the plurality of cameras.

2. The system of claim 1, wherein the plurality of cameras comprises an FPA unit and a plurality of lenses.

3. The system of claim 2, wherein the FPA unit comprises one FPA or a plurality of FPAs.

4. The system of claim 1, wherein the at least one thermal reference source has a known spectrum.

5. The system of claim 4, further comprising an additional thermal reference source disposed such that radiation from the additional thermal reference source is reflected by the plurality of mirrors towards the plurality of cameras.

6. The system of claim 5, wherein the additional reference source has a temperature and a spectrum different from the known temperature and the known spectrum of the at least one reference source.

7. The system of claim 6, wherein the temperature of the additional thermal reference source is less than the known temperature.

8. The system of claim 6, wherein the temperature of the additional thermal reference source is greater than the known temperature.

9. The system of claim 1, wherein the at least one reference source is displaced away from a conjugate image plane of the plurality of cameras such that an image of the at least one reference source captured by the plurality of cameras is blurred.

10. The system of claim 1, wherein the at least one reference source is positioned at a conjugate image plane of the plurality of cameras.

11. The system of claim 1, wherein the plurality of mirrors is disposed outside a central field of view of the plurality of cameras.

12. The system of claim 1, further comprising a first and a second temperature-controlled shutter removably positioned to block IR radiation incident on the system from reaching the plurality of cameras.

13. The system of claim 1, wherein the system includes at least two spatially and spectrally different optical channels.

14. The system of claim 13, wherein the system includes at least three optical channels.

15. The system of claim 13, wherein the system includes at least four optical channels.

16. The system of claim 13, wherein the system includes at least five optical channels.

17. The system of claim 13, wherein the system includes at least six optical channels.

18. The system of claim 13, wherein the system includes at least seven spatially and spectrally different optical channels.

19. The system of claim 13, wherein the system includes at least eight spatially and spectrally different optical channels.

20. The system of claim 13, wherein the system includes at least nine spatially and spectrally different optical channels.

21. The system of claim 13, wherein the system includes at least ten spatially and spectrally different optical channels.

22. The system of claim 13, wherein the system includes at least twelve spatially and spectrally different optical channels.

23. The system of claim 1, further comprising one or more sensors configured to measure a temperature of the at least one reference source.

24. The system of claim 23, wherein the one or more sensors are configured to communicate the measured temperature of the at least one reference source to a temperature controller.

25. The system of claim 23, wherein the one or more sensors are configured to communicate the measured temperature of the at least one reference source to the data-processing unit.

26. The system of claim 1, wherein the plurality of cameras is configured to image a same portion of the at least one reference source.

27. The system of claim 1, wherein the plurality of cameras is configured to acquire multispectral image data from the object continuously for a duration of time.

28. The system of claim 1, comprising at least two spectrally and spatially distinct optical channels configured to capture two-dimensional image data of the object.

29. An infrared (IR) imaging system, the imaging system comprising:
 a plurality of cameras;
 a first temperature-controlled reference source imaged by the plurality of cameras;
 a second temperature-controlled reference source;
 a first and a second temperature-controlled shutter removably positioned to block IR radiation incident on the system from reaching the plurality of cameras; and
 a data-processing unit comprising a processor, said data-processing unit configured to:
  acquire with the plurality of cameras one or more image frames of an object, a plurality of the one or more image frames having regions that correspond to radiation from the first and the second temperature-controlled reference sources; and
  dynamically calibrate the plurality of cameras so that various cameras imaging a scene agree on a temperature estimate of the first and second reference sources.

30. The imaging system of claim 29, wherein the data-processing unit is configured to calculate a dynamic calibration correction and apply the correction to the plurality of cameras for each of the plurality of frames.

31. The system of claim 29, wherein the first reference source is maintained at a first temperature.

32. The system of claim 31, wherein the second reference source is maintained at a second temperature.

33. The system of claim 32, wherein the first temperature is greater than the second temperature.

34. The system of claim 32, wherein the first temperature is less than the second temperature.

35. The system of claim 29, wherein the first and the second reference sources are displaced away from a conjugate image plane of the plurality of cameras such that the image of the first and the second reference sources captured by the plurality of cameras is blurred.

36. The system of claim 29, wherein the first and the second reference sources are positioned at a conjugate image plane of the plurality of cameras.

37. The system of claim 29, further comprising:
 a first mirror configured to image the first reference source onto the plurality of cameras; and
 a second mirror configured to image the second reference source onto the plurality of cameras.

38. The system of claim 29, wherein the system includes at least two spatially and spectrally different optical channels.

39. The system of claim 38, wherein the system includes at least four spatially and spectrally different optical channels.

40. The system of claim 39, wherein the system includes at least six spatially and spectrally different optical channels.

41. The system of claim 39, wherein the system includes at least eight spatially and spectrally different optical channels.

42. The system of claim 39, wherein the system includes at least ten spatially and spectrally different optical channels.

43. The system of claim 39, wherein the system includes at least twelve spatially and spectrally different optical channels.

44. The system of claim 29, further comprising one or more sensors configured to measure a temperature of the first or the second reference source.

45. The system of claim 44, wherein the one or more sensors are configured to communicate the measured temperature of the first or the second reference source to a temperature controller.

46. The system of claim 44, wherein the one or more sensors are configured to communicate the measured temperature of the first or the second reference source to the data-processing unit.

47. The system of claim 29, wherein the plurality of cameras is configured to image a same portion of the first reference source and wherein the plurality of cameras is configured to image a same portion of the second reference source.

48. The system of claim 29, wherein the plurality of cameras are configured to acquire multispectral image data from the object continuously for a duration of time.

49. The system of claim 29, comprising at least two spectrally and spatially distinct optical channels configured to capture two-dimensional image data of the object.

50. An infrared (IR) imaging system, the imaging system comprising:
 a plurality of cameras;
 a reference having an unknown temperature;
 a plurality of mirrors configured to reflect radiation from the reference towards the plurality of cameras; and
 a data-processing unit comprising a processor, the imaging system configured to:
  acquire with the plurality of cameras one or more image frames of an object, a plurality of the one or more image frames having regions with the unknown temperature that corresponds to the reference;
  calculate a dynamic calibration correction using a temperature measured by one of the cameras in the plurality of cameras based on the plurality of the one or more image frames having regions with the unknown temperature as a reference temperature; and
  apply the calibration correction to the other cameras in the plurality of cameras to match the temperature estimate of the other cameras in the plurality of cameras with the reference temperature.

51. The system of claim 50, wherein the reference is displaced away from a conjugate image plane of the plurality of cameras such that the image of the reference captured by the plurality of cameras is blurred.

52. The system of claim 50, wherein the reference is positioned at a conjugate image plane of the plurality of cameras.

53. The system of claim 50, further comprising a first and a second temperature-controlled shutter removably positioned to block IR radiation incident on the system from reaching the plurality of cameras.

54. The system of claim 50, wherein the system includes at least two spatially and spectrally different optical channels.

55. The system of claim 54, wherein the system includes at least three spatially and spectrally different optical channels.

56. The system of claim 54, wherein the system includes at least four spatially and spectrally different optical channels.

57. The system of claim 54, wherein the system includes at least five spatially and spectrally different optical channels.

58. The system of claim 54, wherein the system includes at least six spatially and spectrally different optical channels.

59. The system of claim 54, wherein the system includes at least seven spatially and spectrally different optical channels.

60. The system of claim 54, wherein the system includes at least eight spatially and spectrally different optical channels.

61. The system of claim 54, wherein the system includes at least nine spatially and spectrally different optical channels.

62. The system of claim 54, wherein the system includes at least ten spatially and spectrally different optical channels.

63. The system of claim 54, wherein the system includes at least twelve spatially and spectrally different optical channels.

64. The system of claim 50, wherein the plurality of cameras is configured to image a same portion of the reference.

65. The system of claim 50, wherein the plurality of cameras are configured to acquire multispectral image data from the object continuously for a duration of time.

66. The system of claim 50, comprising at least two spectrally and spatially distinct optical channels configured to capture two-dimensional image data of the object.

* * * * *